US010865253B2

(12) United States Patent
Labrijn et al.

(10) Patent No.: US 10,865,253 B2
(45) Date of Patent: Dec. 15, 2020

(54) RODENT BISPECIFIC HETERODIMERIC PROTEINS

(71) Applicant: GENMAB A/S, Copenhagen V (DK)

(72) Inventors: Aran F. Labrijn, Utrecht (NL); Joyce I. Meesters, Utrecht (NL); Janine Schuurman, Utrecht (NL); Paul Parren, Utrecht (NL); Anthony Armstrong, Spring House, PA (US); Matthew Bunce, Spring House, PA (US); Mark Chiu, Spring House, PA (US); Thomas Nesspor, Spring House, PA (US); Adam Zwolak, Spring House, PA (US)

(73) Assignee: GENMAB A/S, Copenhagen V (DK)

( * ) Notice: Subject to any disclaimer, the term of this patent is extended or adjusted under 35 U.S.C. 154(b) by 0 days.

(21) Appl. No.: 15/536,143

(22) PCT Filed: Dec. 18, 2015

(86) PCT No.: PCT/EP2015/080509
§ 371 (c)(1),
(2) Date: Jun. 15, 2017

(87) PCT Pub. No.: WO2016/097300
PCT Pub. Date: Jun. 23, 2016

(65) Prior Publication Data
US 2017/0327597 A1 Nov. 16, 2017

(30) Foreign Application Priority Data
Dec. 19, 2014 (DK) .................. 2014 00744

(51) Int. Cl.
| C07K 16/00 | (2006.01) |
| A61K 47/68 | (2017.01) |
| C07K 16/28 | (2006.01) |
| C07K 16/46 | (2006.01) |
| C07K 16/32 | (2006.01) |
| A61K 49/00 | (2006.01) |
| C07K 16/40 | (2006.01) |

(52) U.S. Cl.
CPC ........ *C07K 16/462* (2013.01); *A61K 49/0008* (2013.01); *C07K 16/00* (2013.01); *C07K 16/2809* (2013.01); *C07K 16/32* (2013.01); *C07K 16/40* (2013.01); *C07K 2317/21* (2013.01); *C07K 2317/24* (2013.01); *C07K 2317/31* (2013.01); *C07K 2317/526* (2013.01); *C07K 2317/64* (2013.01); *C07K 2317/73* (2013.01)

(58) Field of Classification Search
CPC ...... C07K 16/462; C07K 16/32; C07K 16/00; C07K 16/40; C07K 16/2809; C07K 2317/526; C07K 2317/73; C07K 2317/21; C07K 2317/64; C07K 2317/31; C07K 2317/24; A61K 49/0008; A61K 47/68
See application file for complete search history.

(56) References Cited

U.S. PATENT DOCUMENTS

| 5,292,668 | A | 3/1994 | Paulus |
| 5,807,706 | A | 9/1998 | Carter et al. |
| 6,737,056 | B1 | 5/2004 | Presta |
| 7,960,512 | B2 * | 6/2011 | Stavenhagen .......... C07K 16/00 530/387.1 |
| 8,911,726 | B2 | 12/2014 | Takahashi et al. |
| 9,150,663 | B2 | 10/2015 | Labrijn et al. |
| 9,212,230 | B2 | 12/2015 | Schuurman et al. |
| 10,344,050 | B2 | 7/2019 | Gramer et al. |
| 2004/0038894 | A1 | 2/2004 | Daeron et al. |
| 2008/0051469 | A1 | 2/2008 | Brahmbhatt et al. |
| 2010/0015133 | A1 | 1/2010 | Igawa et al. |
| 2010/0105874 | A1 | 4/2010 | Schuurman et al. |
| 2013/0177555 | A1 * | 7/2013 | Wilkinson ............. C07K 16/00 424/133.1 |
| 2014/0141000 | A1 | 5/2014 | Chiu et al. |
| 2014/0170148 | A1 | 6/2014 | De Goeij et al. |
| 2014/0170149 | A1 | 6/2014 | Neijssen et al. |
| 2014/0242075 | A1 * | 8/2014 | Parren ................ C07K 16/2863 424/136.1 |
| 2014/0303356 | A1 | 10/2014 | Gramer et al. |
| 2016/0046727 | A1 | 2/2016 | Labrijn et al. |
| 2016/0159930 | A1 | 6/2016 | Schuurman et al. |
| 2017/0233497 | A1 | 8/2017 | Labrijn et al. |

FOREIGN PATENT DOCUMENTS

| DE | 19859115 A1 | 3/2000 |
| EP | 1693386 A1 | 8/2006 |
| EP | 1870459 A1 | 12/2007 |
| WO | 96/27011 A1 | 9/1996 |
| WO | 98/04592 A1 | 2/1998 |
| WO | 98/50431 A2 | 11/1998 |

(Continued)

OTHER PUBLICATIONS

Rudikoff et al., Proc Natl Acad Sci USA vol. 79 pp. 1979-1983 (Year: 1982).*
Yu et al., Investigative Ophthalmology & Visual Science 49(2): 522-527 (Year: 2008).*
Wu et al., J Mol Biol 294: 151-162 (Year: 1999).*
Lund et al., The Journal of Immunology 157:4963-4969 (Year: 1996).*
Hay et al., Nature Biotechnology 32(1): 40-51 (Year: 2014).*
Aalberse, Rob C. et al., "IgG4 breaking the rules," Immunology, vol. 105:9-19 (2002).
Aalberse, Rob C. et al., "Serologic Aspects of IgG4 Antibodies. I. Prolonged Immunization Results in an IgG4-Restricted Response," The Journal of Immunology, vol. 130(2):722-726 (1983).

(Continued)

*Primary Examiner* — Phuong Huynh
(74) *Attorney, Agent, or Firm* — Nelson Mullins Riley & Scarborough LLP; Jane E. Remillard, Esq.; Cynthia L. Kanik

(57) ABSTRACT

Novel rodent bispecific heterodimeric proteins, such as rodent bispecific antibodies, in vitro method for producing such, and uses thereof.

14 Claims, 12 Drawing Sheets
Specification includes a Sequence Listing.

(56) References Cited

FOREIGN PATENT DOCUMENTS

| | | |
|---|---|---|
| WO | 9955369 A1 | 11/1999 |
| WO | 02/100348 A2 | 12/2002 |
| WO | 2004/035607 A2 | 4/2004 |
| WO | 2005/000899 A2 | 1/2005 |
| WO | 2005/062916 A2 | 7/2005 |
| WO | 2006/047340 A2 | 5/2006 |
| WO | 2006106905 A1 | 10/2006 |
| WO | 2007/059782 A1 | 5/2007 |
| WO | 2007/103112 A2 | 9/2007 |
| WO | 2007/110205 A2 | 10/2007 |
| WO | 2008/119353 A1 | 10/2008 |
| WO | 2008/145140 A2 | 12/2008 |
| WO | 2008/145142 A1 | 12/2008 |
| WO | 2009/089004 A1 | 7/2009 |
| WO | 2010/063785 A2 | 6/2010 |
| WO | 2010/129304 A2 | 11/2010 |
| WO | 2011/131746 A2 | 10/2011 |
| WO | WO-2011131746 A2 * | 10/2011 ......... C07K 16/1063 |
| WO | 2011/143545 A1 | 11/2011 |
| WO | 2012/058768 A1 | 5/2012 |
| WO | 2012/116453 A1 | 9/2012 |
| WO | 2012143524 A2 | 10/2012 |
| WO | WO2012/143524 * | 10/2012 |

OTHER PUBLICATIONS

Aalberse, Rob C. et al., "The Apparent Monovalency of Human IgG4 Is Due to Bispecificity," International Archives of Allergy and Immunology, vol. 118:187-189 (1999).

Aalberse, Rob C., "Physiological Fab arm exchange of IgG4 generates an anti-inflammatory antibody," Genmab, European Antibody Congress, 36 pages (2008).

Angal, S. et al., "A Single Amino Acid Substitution Abolishes the Heterogeneity of Chimeric Mouse/Human (IgG4) Antibody," Molecular Immunology, vol. 30(1):105-108 (1993).

Bloom, James W. et al., "Interchain disulfide bond in the core hinge region of human IgG4," Protein Science, vol. 6:407-415 (1997).

Brusco et al., "Molecular characterization of immunoglobulin G4 gene isoallotypes," Eur J Immnogene, 25:349-355 (1998).

Ciccimarra, F. et al., "Localization of the IgG effector site for monocyte receptors," PNAS, 72:2081-2083(1975).

Dall'Acqua, William et al., "Contribution of Domain Interface Residues to the Stability of Antibody CH3 Domain Homodimers," Biochemistry, vol. 37:9266-9273 (1998).

Deng, Liang et al., "Detection and quantification of the human IgG4 half-molecule, HL, from unpurified cell-culture supernatants," Biotechnol. Appl. Biochem., vol. 40:261-269 (2004).

Genmab, "Better Antibodies by Design," www.genmab.com, 2 pages (2011).

Genmab, "Building for a Commercial Future: Research, Development and Business Update," slideshow, 65 pages (2006).

Genmab, "DuoBody platform, Genmab's proprietary bispecific antibody platform," slideshow, 15 pages, (2011).

Genmab, "DuoBody, Genmab's proprietary bispecifiic antibody platform," slideshow, 13 pages (2011).

Genmab, "DuoBody, The next generation of therapeutic antibodies," www.genmab.com, 2 pages (2011).

Genmab, "DuoBody: Innovative Bispecific Antibody Platform," Poster for R&D Day, 1 page (2011).

Genmab, "Genmab, Beter Antibodies by Design," slideshow, 18 pages (2011).

Genmab, "The physiological generation of bispecific IgG4 antibodies," Sanquin Spring Symposium, slideshow, 54 pages (2007).

Genmab, "Therapeutic IgG4 antibodies engage in Fab-arm exchange with patients' IgG4 in vivo," Antibodies as Drugs, Poster #214, 14 pages (2009).

Gunasekaran, K. et al., "Enhancing Antibody Fc Heterodimer Formation through Electrostatic Steering Effects: Applications to Bispecific Molecules and Monovalent IgG," Journal of Biological Chemistry, vol. 285 (25):19637-19646 (2010).

International Preliminary Report on Patentabilty, PCT/EP2015/080509, dated Jun. 20, 2017, 9 pages.

International Search Report and Written Opinion, PCT/EP2015/080509, dated Mar. 30, 2016, 13 pages.

Klein, C. et al., "Progress in overcoming the chain association issue in bispecific heterodimeric IgG antibodies," mAbs, vol. 4(6):653-663 (2012).

Labrijn et al, "Controlled fab-arm exchange for the generation of stable bispecific IgG1," Nature Protocols, vol. 9 (10): 2450-2463 (2014).

Labrijn et al., "Efficient generation of stable bispecific IgG1 by controlled Fab-arm exchange," Proc Natl Acad Sci., vol. 110(13):5145-5150 (2013).

Labrijn, Aran F. et al., "Species-Specific Determinants in the IgG CH3 Comain Enable Fab-Arm Exchange by Affecting the Noncovalent CH3-CH3 Interaction Strength," The Journal of Immunology, vol. 187, 9 pages (2011).

Labrijn, Aran F. et al., "Species-specific determinants in the immunoglobulin CH3 domain enable Fab-arm exchange by affecting the non-covalent CH3-CH3 interaction strength," Keystone Symposium, Antibodies as Drugs Poster Presentation, 1 page (2011).

Labrijn, Aran F. et al., "Therapeutic IgG4 antibodies engage in Fab-arm exchange with endogenous human IgG4 in vivo," Nature Biotechnology, vol. 27(8):767-771 (2009).

Lewis, Kenneth B. et al., "Comparison of the ability of wild type and stabilized human IgG4 to undergo Fab arm exchange with endogenous IgG4 in vitro and in vivo," Molecular Immunology, vol. 46:3488-3494 (2009).

Lindhofer, H, et al., "Preferential species-restricted heavy/light chain pairing in rat/mouse quadromas. Implications for a single-step purification of bispecific antibodies," J Immunol., vol. 155(1):219-225 (1995).

Marvin, Jonathan S. et al., "Recombinant approaches to IgG-like bispecific antibodies," Acta Pharmacologica Sinica, vol. 26(6):649-658 (2005).

Merchant, A. Margaret et al., "An efficient route to human bispecific IgG," Nature Biotechnology, vol. 16:677-681 (1998).

Milstein C. et al., "Hybrid hybridomas and their use in immunohistochemistry," Nature, vol. 305(5934):537-540 (1983).

Mori, K. et al.,"Non-fucosylated therapeutic antibodies: the next generation of therapeutic antibodies," Cytotechnol., vol. 55:109-114 (2007).

Ooijevaar-De Heer, Pleuni G. et al., "Fc binding activity of IgG4 is a confounding factor in the measurement of IgG4 bispecificity," Sanquin Spring Symposium, 1 page (2007).

Parren, Paul, "UniBody, a novel nonactivating antibody format," Beyond Antibodies, slideshow, 35 pages (2009).

Rispens, Theo et al., "Human IgG4 Binds to IgG4 and Conformationally Altered IgG1 via Fc-Fc Interactions," The Journal of Immunology, vol. 182:4275-4281 (2009).

Rispens, Theo, "IgG4: an odd antibody, Fc interactions and the relation to half-molecule exchange," Sanquin, slideshow, 41 pages (2009).

Schuurman, J. et al., "Normal human immunoglobulin G4 is bispecific: it has two different antigen-combining sites," Immunology, vol. 97:693-698 (1999).

Schuurman, Janine et al., "Anti-Inflammatory Activity of Human IgG4 Antibodies by Dynamic Fab Arm Exchange," World BioPharm Forum, Poster, 1 page (2009).

Schuurman, Janine et al., "The inter-heavy chain disulfide bonds of IgG4 are in equilibrium with intra-chain disulfide bonds," Molecular Immunology, vol. 38:1-8 (2001).

Schuurman, Janine, "IgG4 therapeutic antibodies," World BioPharm Forum, slideshow, 26 pages (2009).

Schuurman, Janine, "Post-Transcriptional Modifications," Genmab, slideshow, 43 pages (2008).

Schuurman, Janine, "The impact of Fab-arm exchange on the development of antibody therapeutics," Antibody Discovery & Development Forum, slideshow, 30 pages (2011).

(56) References Cited

OTHER PUBLICATIONS

Schuurman, Janine, "The impact of Fab-arm exchange on the development of antibody therapeutics," Antibody Engineering and Design, slideshow, 29 pages (2011).
Schuurman, Janine, "The impact of Fab-arm exchange on the development of antibody therapeutics," Genmab, slideshow, 26 pages (2010).
Scinicariello, F. et al.,., "Rhesus macaque antibody molecules: sequences and heterogeneity of alpha and gamma constant regions," Immunol., vol. 111:66-74 (2004).
Stubenrauch, Kay et al., "Impact of Molecular Processing in the Hinge Region of Therapeutic IgG4 Antibodies on Disposition Profiles in Cynomolgus Monkeys," Drug Metabolism and Disposition, vol. 38(1):84-91 (2010).
Van Berkel, Patrick H.C., "Development of a production process for DuoBody: a novel human bispecific platform," Informa/IBC Life Sciences' Bioproduction Conference, Poster, 1 page (2011).
Van De Winkel, Jan et al., "Better Antibodies by Design, 2011 R&D Day," slideshow, 109 pages (2011).
Van Der Neut Kolfschoten, Marijn et al., "Anti-Inflammatory Activity of Human IgG4 Antibodies by Dynamic Fab Arm Exchange," Science, vol. 317:1554-1557 (2007).
Van Der Zee, J.S. et al., "Inhibition of complement activation by IgG4 antibodies," Clin. exp. Immunol., vol. 64:415-422 (1986).
Zuckier et al., "Chimeric human-mouse IgG antibodies with shuffled constant region exons demonstrate that multiple domains contribute to in vivo half-life," Cancer Research, 58:3905-3908 (1998).
Junttila, T. et al., "Antitumor Efficacy of a Bispecic Antibody That Targets HER2 and Activates T Cells," American Association for Cancer Research, vol. 74(19): 5561-5571 (2014).

* cited by examiner

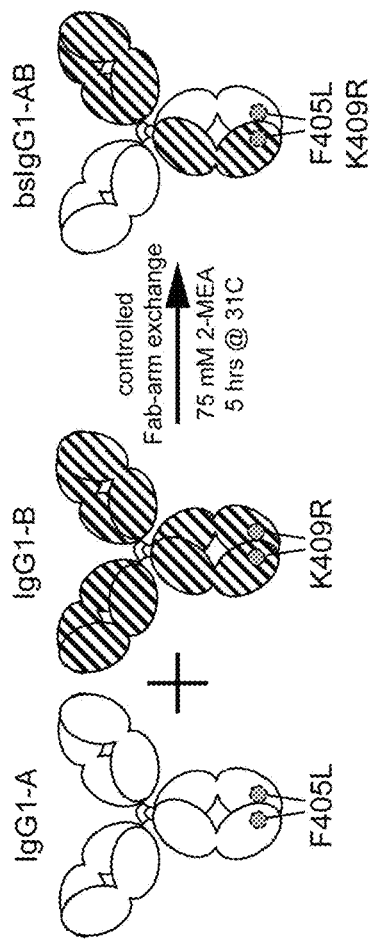
FIG. 1A
FIG. 1B
FIG. 1C

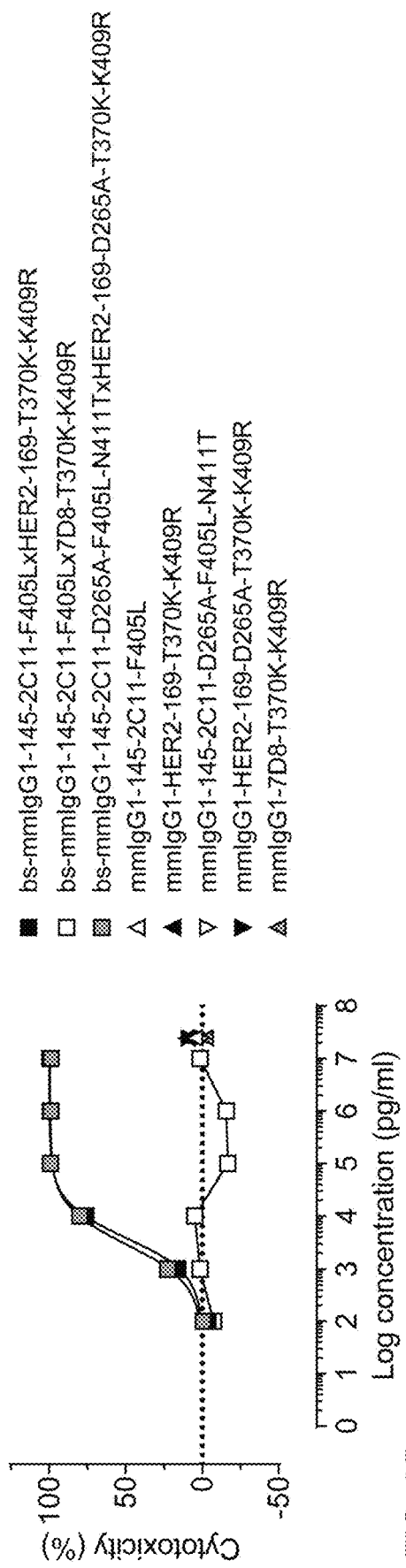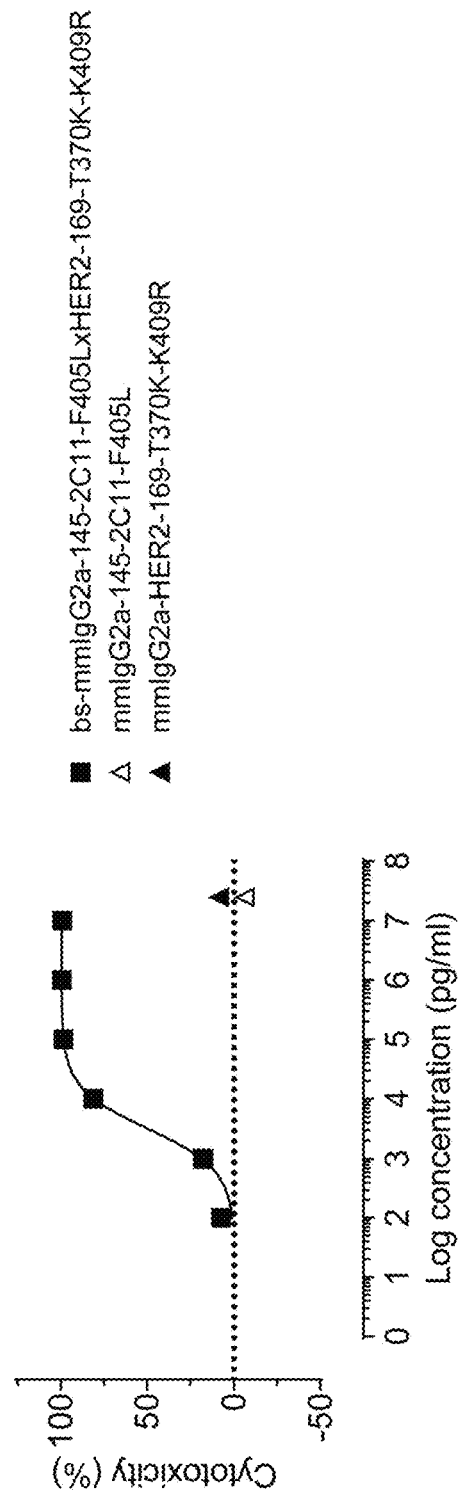

RODENT BISPECIFIC HETERODIMERIC PROTEINS

REFERENCE TO RELATED APPLICATIONS

This application is a 35 U.S.C. 371 national stage filing of International Application No. PCT/EP2015/080509, filed Dec. 18, 2015, which claims priority to Danish Patent Application No. PA 2014 00744, filed Dec. 19, 2014. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Jun. 15, 2017, is named GMI_164US_Sequence_Listing.txt and is 76,731 bytes in size.

FIELD OF THE INVENTION

The present invention relates to novel heterodimeric proteins such as bispecific antibodies of primarily rodent origin.

BACKGROUND OF THE INVENTION

Monoclonal antibodies have in recent years become successful therapeutic molecules, in particular for the treatment of cancer. Unfortunately, however, monoclonal antibodies are often unable to cure diseases when used as monotherapy. Bispecific antibodies can potentially overcome some of the limitations of monoclonal antibody therapy, e.g. they could be used as mediators to target a drug or toxic compound to target cells, as mediators to retarget effector mechanisms to disease-associated sites or as mediators to increase specificity for tumor cells, for example by binding to a combination of targets molecules that is exclusively found on tumor cells. Different formats and uses of bispecific antibodies have been reviewed by Chames and Baty ((2009) Curr Opin Drug Disc Dev 12: 276) and by Kontermann and Brinkman ((2015) Drug Discovery Today 20: 838).

An in vitro method for producing bispecific antibodies is described in WO 2008119353 (Genmab). Herein is described that a bispecific antibody is formed by "Fab-arm" or "half-molecule" exchange (swapping of a heavy chain and attached light chain) between two monospecific antibodies having IgG4-like CH3 regions upon incubation under reducing conditions. This Fab-arm exchange reaction is the result of a disulfide-bond isomerization reaction and dissociation-association of CH3 domains wherein heavy-chain disulfide bonds in the hinge regions of the parent (originally monospecific) antibodies are reduced and the resulting free cysteines form an inter heavy-chain disulfide bond with cysteine residues of another parent antibody molecule (originally with a different specificity), and simultaneously CH3 domains of the parent antibodies dissociate and re-associate with the CH3 domains of the other parent antibody. The resulting product is a bispecific antibody having two Fab arms which potentially are composed of different sequences. WO2011131746 (Genmab) describes that by introducing asymmetrical, matching mutations in the CH3 regions of the two monospecific starting proteins, the Fab-arm exchange reaction can be forced to become directional and thereby yield highly stable heterodimeric proteins. This so-called controlled Fab-arm exchange (cFAE) involves the mixing of two separately expressed parental IgGs under controlled reducing conditions to allow the recombination of antibody half-molecules. The recombination is driven by two matching point-mutations, such as F405L and K409R (EU-numbering index), one in either parental IgG, which weaken the non-covalent CH3-CH3 interaction in the parental Abs enough to allow dissociation of half-molecules, but at the same time, strongly favour heterodimerization, thus promoting bispecific IgG endproduct yield and post-exchange stability upon re-oxidation of the hinge disulfides.

Except for their dual specificity, it was found that bispecific antibodies generated from human IgGs using cFAE behaved as regular, monospecific human IgGs. Thus, Fc-effector functions of these bispecific human IgGs were preserved and the pharmacokinetics were similar as regular IgG (Labrijn et al. 2013. Proc Natl Acad Sci USA 110(13): 5145-50).

To predict the efficacy and safety of bispecific IgGs for further development in the clinic, extensive preclinical research is required. The use of animal models is essential for the understanding of the mechanisms of action of therapeutic bispecific human IgGs. Proof-of-concepts for therapeutic antibodies are often established in pre-clinical xenograft models using immunodeficient mice. For many therapeutic concepts, however, the use of surrogate antibodies in rodent disease models such as a mouse model is warranted. The use of mouse or other rodent antibodies enables optimal cross-talk with mouse or other rodent effector cells and proteins, it allows the bispecific antibodies to be assessed in rodent disease models and in addition limits potential immunogenicity which is likely to be a problem for human antibodies applied in rodents, thus allowing long-term treatment of the rodent.

In the early 1980s it has been shown that fusion of two mouse hybridomas (quadroma) allows for the production of murine hybrid immunoglobulin molecules containing two different binding sites (Milstein C, Cuello A C. Nature. 1983 Oct. 6-12; 305(5934):537-40). Because the various H and L chains expressed by the quadroma will randomly pair, the yield of the desired bispecific pair of H/L chains was very low. Therefore, another bispecific antibody format involving cross-rodent species IgGs has been developed by Lindhofer et al. (1995 J Immunol 155:219). Using this method, rat and mouse hybridomas producing different antibodies are fused, leading to enrichment of functional bispecific antibodies, because of preferential species-restricted heavy/light chain pairing. The bispecific antibodies are then purified from the mixture that also contains monospecific antibodies. Thus, half of the resulting bispecific antibody is derived from mouse IgG and the other half is derived from rat IgG. Such bispecific antibodies will most likely be immunogenic in mouse or rat as half of the molecule will be foreign.

Thus, there is a need for surrogate bispecific rodent antibodies for facilitating studies in immunocompetent mouse or other rodent models, in which antibodies will have optimal cross-talk with mouse or other rodent effector cells and proteins, which can be used in rodent disease models and will have limited immunogenicity.

It is thus an object of the present invention to provide heterodimeric proteins such as bispecific antibodies which can be used in rodent disease models as surrogate for human bispecific antibodies e.g. for investigating mechanisms of action, effector functions, toxicity, unwanted mechanisms and side effects, anti-tumor efficacy, treatment efficacy, T-cell mediated anti-tumor efficacy, immune modulation, pharmacodynamics and/or pharmacokinetics of the heterodimeric protein, which antibodies have limited immunogenicity in the rodent compared to fully human or humanized antibodies. It is a further object of the present invention to provide rodent heterodimeric proteins which can be used as research tools.

SUMMARY OF THE INVENTION

The present inventors surprisingly found, that the two matching point mutations of the prior art bispecifics were less optimal in driving rodent homodimeric proteins in the direction that favours heterodimerization.

The inventors found that at least one further amino acid modification on the first homodimer was needed for providing at least 85% of the desired rodent heterodimeric proteins.

Accordingly, the present invention relates in one aspect to heterodimeric proteins comprising a first polypeptide of a first homodimeric protein, said first polypeptide comprising a first variable region having a first binding specificity and a first Fc region, said first Fc region comprising a first CH3 domain; and a second polypeptide of a second homodimeric protein, said second polypeptide comprising a second variable region having a second binding specificity and a second Fc region, said second Fc region comprising a second CH3 domain, wherein the variable regions may origin from any species and the Fc regions origin from a rodent species, and wherein the first CH3 domain comprises an amino acid selected from Gly, Ala, Val, Leu, Ile, Ser, Lys, Arg, His, Asp, Asn, Glu, Gln, Trp, Phe, Tyr, and Met at position 370 and a substitution of the amino acid residue at position 409 selected from Gly, Ala, Val, Ile, Ser, Arg, His, Asp, Asn, Glu, Gln, Trp, Phe, Tyr and Thr and the second CH3 domain comprises a substitution of the amino acid residue at position 405 selected from Ala, Val, Leu, Ile, Ser, Lys, His, Asp, Asn, Glu, Gln, Trp, Tyr and Thr, relative to the wild type IgG isotype from said rodent species when using EU numbering index.

The invention further relates to the use of such heterodimeric proteins and to the method of production of such proteins.

BRIEF DESCRIPTION OF THE DRAWINGS

FIGS. 1A-1C: FIG. 1A) Principle of controlled Fab-arm exchange for the generation of human IgG1-based bispecific antibodies. Alignment of human (*Homo sapiens*; hs) and rodent (*Mus musculus*; mm, *Rattus norvegicus*; rn) sequences of (FIG. 1B) hinge regions and (FIG. 1C) CH3 regions. EU-numbering convention is used to annotate amino acid residues.

FIG. 3A) Overlay of HIC profiles of 2F8 and 7D8-derived parental antibodies (black dotted and gray dashed lines, respectively) and the bispecific antibody product (black solid line) generated by controlled Fab-arm exchange. FIG. 3B) Exemplary HIC profiles of bispecific antibodies generated by controlled Fab-arm exchange using the indicated (above and left of panels) combination of parental antibodies. Numbers indicate percentages of bispecific antibody product (middle peaks) and residual 2F8 and 7D8-derived parental antibodies (left and right peaks, respectively). Vertical lines correspond with the retention times of the HIC analyses of the individual parental antibodies.

FIG. 4A) Schematic representation of chimeric IgG1 molecules containing mouse-derived constant regions having the F405L and K409R matching mutations alone or in combination with additional N/R411T and V/T370K mutations, respectively. FIG. 4B) and FIG. 4C) Efficiency of controlled Fab-arm exchange as measured by dual-binding ELISA (solid bars) or HIC (open bars) of mixtures of 2F8-derived and 7D8-derived mmIgG1, mmIgG2a, mmIgG2b or mmIgG3 parental antibodies without mutations (WT) (FIG. 4B; left panel), with the F405L or K409R mutation, respectively, (FIG. 4B; right panel), with the F405L or T/V370K-K409R mutations, respectively, (FIG. 4C; left panel), or with the F405L-N/R411T or T/V370K-K409R mutations, respectively, (FIG. 4C; right panel). Data represent mean±SEM. nd=not done.

FIG. 6A) Isothermal titration calorimetry (ITC) analysis of the binding of mmIgG2b variants to the Z-domain. Isotherms resulting from the binding of Z-domain to mmIgG2b variants. Top panels show the isotherms representing power input over time. In the bottom panels total energy required for equilibration as a function of the molar ratio of injectant (Z-domain) to titrant (IgG). FIG. 6B) MAbSelect Sure separation of mmIgG2b variants and the corresponding bispecific antibody product by 3-step pH gradient elution. Chromatograms show the absorption at 280 nm (solid line; left y-axis) and the pH profile (dashed grey line; right y-axis) during the purification. FIG. 6C) Fractions from each elution step: pH 7.2, 4.0, and 3.4 for the mixed sample containing both parental Abs and the bispecific Ab (dotted hashed trace in panel B) were analyzed by hydrophobic interaction chromatography (HIC). Dashed lines indicate the elution volume of the two parental Abs and the bispecific Ab. Note that the elution volume of the bispecific Ab is intermediate between that of the parental Abs.

FIG. 7A) Schematic representation of chimeric IgG1 molecules containing rat-derived constant regions having the F405L and K409R matching mutations alone or in combination with additional N/S411T and S/T370K mutations, respectively. FIG. 7B) and FIG. 7C) Efficiency of controlled Fab-arm exchange as measured by dual-binding ELISA (solid bars) or HIC (open bars) of mixtures of 2F8-derived and 7D8-derived rnIgG1, rnIgG2a, rnIgG2b or rnIgG2c parental antibodies without mutations (WT) (FIG. 7B; left panel), with the F405L or K409R mutation, respectively, (FIG. 7B; right panel), with the F405L or S/T370K-K409R mutations, respectively, (FIG. 7C; left panel), or with the F405L-N/S411T or S/T370K-K409R mutations, respectively, (FIG. 7C; right panel). Data represent mean±SEM. nd=not done. na=not applicable.

FIGS. 9A and 9B: T-cell mediated cytotoxicity of AU565 cells (target cells; T) cocultured for 3 days at 37° C. with mouse splenocytes (effector cells; E) in the presence of serial diluted (FIG. 9A) mmIgG1-derived or (FIG. 9B) mmIgG2a-derived bispecific antibodies and parental control antibodies (as indicated), with a E:T ratio of 2:1. Data represents mean of a representative experiment (n=2).

DETAILED DESCRIPTION OF THE INVENTION

Definitions

Figure 2A:
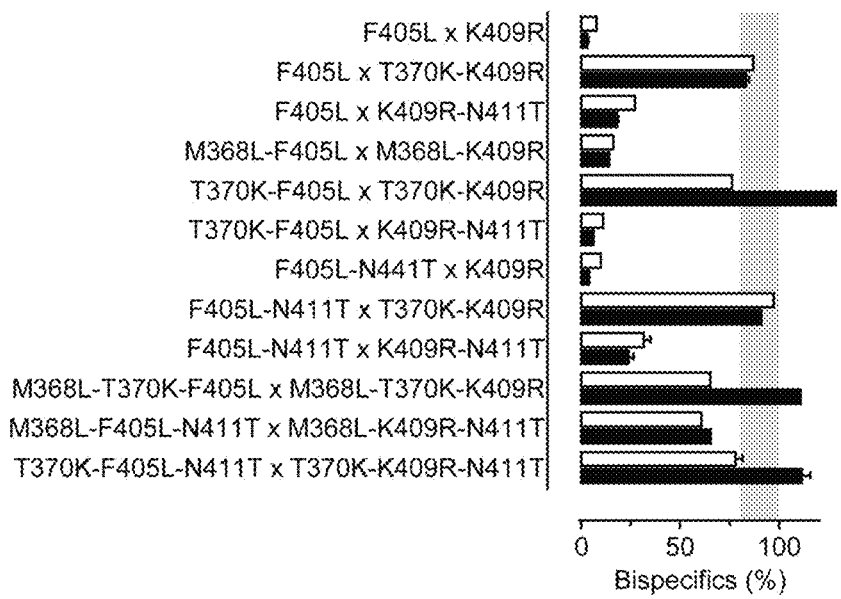
FIGS. 2A-2C: Efficiency of controlled Fab-arm exchange (cFAE) as measured by dual-binding ELISA (solid bars) or Hydrophobic Interaction Chromatography (HIC) (open bars) of mixtures of 2F8-derived and 7D8-derived (FIG. 2A) hsIgG1-CH3 (mmG1), (FIG. 2B) hsIgG1-CH3 (mmG2a) or (FIG. 2C) hsIgG1-CH3 (mmG2b) parental antibodies. The 2F8-derived and 7D8-derived parental antibodies contained the indicated mutations, respectively. Data represent mean±SEM. nd=not done. As the presence of aggregates can influence quantification by ELISA (overestimation), the HIC values are considered more accurate.

The term "immunoglobulin" refers to a class of structurally related glycoproteins consisting of two pairs of polypeptide chains, one pair of light (L) chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain "constant region" typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)).

Herein, the numbering of amino acid residues in the constant region is performed according to the "EU numbering index" as described in Kabat et al., Sequences of Proteins of Immunological Interest, 5th Ed. Public Health Service, National Institutes of Health, Bethesda, Md. (1991). The variable regions are numbered according to the IMGT numbering system as described in "IMGT unique numbering for immunoglobulin and T cell receptor variable domains and Ig superfamily V-like domains": Lefranc, M.-P. et al., Dev. Comp. Immunol., 27, 55-77 (2003)

When used herein, the term "Fab-arm" is used interchangeably with the term "half molecule" and refers to one heavy chain-light chain pair.

When used herein, the term "Fc region" refers to an antibody region comprising at least the hinge region, the CH2 domains and the CH3 domains. Thus, the Fc region is part of the constant region.

When used herein, the term "constant region" refers to constant regions of an immunoglobulin, i.e. the regions CH1, hinge, CH2 and CH3.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 min, at least about 45 min, at least about one hour, at least about two hours, at least about four hours, at least about 8 hours, at least about 12 hours (h), about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as Clq, the first component in the classical pathway of complement activation. An antibody may also be a bispecific antibody, diabody, or similar molecule. The term "bispecific antibody" refers to antibodies having specificities for at least two different epitopes, typically non-overlapping epitopes. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody, e.g. a F(ab')2 fragment. It also should be understood that the term antibody, unless specified otherwise, also includes polyclonal antibodies, monoclonal antibodies (mAbs), antibody-like polypeptides, such as chimeric antibodies and humanized antibodies. An antibody as generated can possess any isotype.

The term "full-length antibody" when used herein, refers to an antibody which contains all heavy and light chain constant and variable domains that are normally found in an antibody of that isotype.

As used herein, "isotype" refers to the immunoglobulin class (for humans for instance IgG1, IgG2, IgG3, IgG4, IgD, IgA, IgE, or IgM) that is encoded by heavy chain constant region genes, including all allotypes. Isotypes of Mus musculus (mm) include for instance IgG1, IgG2a, IgG2b, IgG2c and IgG3. Isotypes of *Rattus norvegicus* (rn) include for instance IgG1, IgG2a, IgG2b, and IgG2c.

The term "allotype" when used herein, refers to variations in the amino acid sequences which are found naturally within a population.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "rodent" as used herein is intended to include all members of the order of Rodentia (Carleton, M. D.; Musser, G. G. (2005). "Order Rodentia", In Wilson, Don E.; Reeder, DeeAnn M. Mammal Species of the World: A Taxonomic and Geographic Reference, Volume 12. JHU Press. pp. 745-752. ISBN 978-0-8018-8221-0.)

The term "rodent antibody" or "rodent heterodimeric protein" as used herein, is intended to include antibodies or heterodimeric proteins having variable and constant regions derived from a rodent species immunoglobulin sequences, such as e.g. a mouse or a rat. The rodent antibodies or heterodimeric proteins of the invention may include amino acid residues not encoded by rodent immunoglobulin sequences (e.g., mutations introduced by random or site-specific mutagenesis in vitro or by somatic mutation in vivo). The term "rodent antibody" or "rodent heterodimeric protein", as used herein, is also intended to include antibodies or heterodimeric proteins in which CDR sequences or the variable region sequences are derived from another species such as e.g. a human or another mammalian species.

When used herein, the term "heavy chain antibody" or "heavy-chain antibody" refers to an antibody which consists only of two heavy chains and lacks the two light chains usually found in antibodies. Heavy chain antibodies, which naturally occur in e.g. camelids, can bind antigens despite having only VH domains.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specific antigen binding peptide (in other words, the amino acid residue is within the footprint of the specific antigen binding peptide).

As used herein, the term "binding" in the context of the binding of an antibody to a predetermined antigen typically is a binding with an affinity corresponding to a KD of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold. The term "KD" (M), as used herein, refers to the dissociation equilibrium constant of a particular antibody-antigen interaction.

When used herein the term "heterodimeric interaction between the first and second CH3 regions" refers to the interaction between the first CH3 region and the second CH3 region in a first-CH3/second-CH3 heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

An "isolated antibody," as used herein, denotes that the material has been removed from its original environment (e.g., the natural environment if it is naturally occurring or the host cell if it is recombinantly expressed). It is also advantageous that the antibodies be in purified form. The term "purified" does not require absolute purity; rather, it is intended as a relative definition, indicating an increase of the antibody concentration relative to the concentration of contaminants in a composition as compared to the starting material.

The term "host cell", as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

When used herein, the term "co-expression" of two or more nucleic acid constructs, refers to expression of the two constructs in a single host cell.

The term "tumor cell protein" refers to a protein located on the cell surface of a tumor cell.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. In some embodiments, an effector cell may phagocytose a target antigen or target cell.

The term "reducing conditions" or "reducing environment" refers to a condition or an environment in which a substrate, here a cysteine residue in the hinge region of an antibody, is more likely to become reduced than oxidized.

The term "disulfide bond isomerization" refers to an exchange of disulfide bonds between different cysteines, i.e., the shuffling of disulfide bonds.

Embodiments of the Invention

In a first aspect the invention relates to a heterodimeric protein comprising:
a first polypeptide of a first homodimeric protein, said first polypeptide comprising a first variable region having a first binding specificity and a first Fc region, said first Fc region comprising a first CH3 domain; and
a second polypeptide of a second homodimeric protein, said second polypeptide comprising a second variable region having a second binding specificity and a second Fc region, said second Fc region comprising a second CH3 domain,
wherein the variable regions may originate from any species and the Fc regions originate from a rodent species, and wherein the first CH3 domain comprises an amino acid selected from Gly, Ala, Val, Leu, Ile, Ser, Lys, Arg, His, Asp, Asn, Glu, Gln, Trp, Phe, Tyr and Met at position 370 and a substitution of the amino acid residue at position 409 selected from Gly, Ala, Val, Ile, Ser, Arg, His, Asp, Asn, Glu, Gln, Trp, Phe, Tyr and Thr and the second CH3 domain comprises a substitution of the amino acid residue at position 405 selected from Ala, Val, Leu, Ile, Ser, Lys, His, Asp, Asn, Glu, Gln, Trp, Tyr and Thr, relative to the wild type IgG isotype from said rodent species when using EU numbering index for position numbering.

In one aspect of the invention the heterodimeric protein is a bispecific antibody.

In one embodiment the Fc regions of the heterodimeric protein are from mouse, rat, hamster, cotton rat or guinea pig origin.

In one embodiment the Fc regions of the heterodimeric protein are from mouse origin.

In one embodiment the Fc regions of the heterodimeric protein are from rat origin.

In one embodiment the Fc regions of the heterodimeric protein are from hamster origin.

In one embodiment the Fc regions of the heterodimeric protein are from cotton rat origin.

In one embodiment the Fc regions of the heterodimeric protein are from guinea pig origin.

In a preferred embodiment the Fc regions of the heterodimeric protein are of mouse or rat origin. In one embodiment they are of *Mus musculus* (mm) origin. In another embodiment they are of *Rattus norvegicus* (rn) origin. The first and second Fc regions may be obtained from the same species but they may also be of two different species, so that the first Fc region is of one species and the second Fc region is of another species. It is preferred that they are of the same species. In another embodiment the Fc regions are chimeric so that e.g. the first Fc region may be of two different species. In one embodiment the first and second Fc regions both origin from *Mus Musculus*. In another embodiment the first and second Fc regions both origin from *Rattus Norvegicus*.

In one aspect of the invention, the variable regions of the heterodimeric protein are of rodent origin. In one embodiment the variable regions are of the same origin as the Fc regions so that the heterodimeric protein is e.g. fully mouse protein, such as fully mouse bispecific antibody. In another embodiment it is a fully rat bispecific antibody. Such bispecific fully mouse or rat antibodies may be useful as surrogate antibodies for use in a mouse or rat model for predicting e.g. the efficacy and safety of human or humanized bispecific antibodies binding the same targets. These bispecific antibodies may also be useful for further preclinical research where the use of animal models is essential for the understanding of the mechanisms of action of therapeutic bispecific human IgGs. Proof-of-concepts for therapeutic antibodies are often established in pre-clinical xenograft models using immune deficient mice. For many therapeutic concepts, however, the use of surrogate antibodies in rodent disease models such as a mouse model is warranted. The use of mouse or other rodent antibodies enables optimal crosstalk with mouse or other rodent effector cells and proteins, and in addition limits potential immunogenicity which is likely to be a problem for human antibodies applied in rodents, thus allowing long-term treatment of the rodent. Thus, in certain applications it is an advantage that the bispecific antibody is fully rodent.

For other applications it may be an advantage that the variable regions originate from a human antibody. Accordingly, in one embodiment the variable regions of the heterodimeric protein are of human origin. In another embodiment they are humanized rodent variable regions. In yet another embodiment the first and second polypeptides of the heterodimeric protein comprise human variable regions and rodent Fc regions. In yet another embodiment the first and second polypeptides of the heterodimeric protein comprise human variable regions and mouse Fc regions, such as *Mus musculus* derived Fc regions.

Hereby chimeric heterodimeric proteins are provided which at least recognize human targets but which preferably have no or very limited immunogenicity in rodents. In this way, mechanisms of human heterodimeric protein clinical candidates, such as bispecific antibody clinical candidates may be tested in a mouse or other rodent model. Accordingly, the present invention provides chimeric bispecific antibodies that may comprise human variable regions and rodent constant regions. Using human variable regions which are identical to variable regions of a lead clinical candidate and the rest of the molecule being of rodent origin, the present invention provides a format by which e.g. mechanisms of action, effector functions, toxicity, unwanted mechanisms and/or side effects, anti-tumor efficacy, treatment efficacy, T-cell mediated anti-tumor efficacy, immune modulation, pharmacodynamics and/or pharmacokinetics of said heterodimeric protein may be investigated in a rodent model. This information may be very useful and predictive of the corresponding functions and effects in humans of the fully human antibody counterpart having identical variable regions but human constant regions.

In some embodiments, the stable heterodimeric protein can be obtained at high yield using the method of the invention on the basis of two homodimeric starting proteins containing only a few, fairly conservative, asymmetrical mutations in the CH3 regions.

Thus, in one embodiment, the sequences of said first and second CH3 regions contain amino acid substitutions at non-identical positions.

In one embodiment, said first homodimeric protein has no more than two amino acid substitutions in the CH3 region, and the second homodimeric protein has no more than one amino acid substitution in the CH3 region relative to the relevant wild-type CH3 regions.

In certain embodiments of the invention the first CH3 domain of the heterodimeric protein comprise a Lysine (K) at amino acid position 370 and a substitution of the amino acid residue at position 409 selected from Gly, Ala, Val, Ile, Ser, Arg, His, Asp, Asn, Glu, Gln, Trp, Phe, Tyr, and Thr and the second CH3 domain comprises a substitution of the amino acid residue at position 405 selected from Ala, Val, Leu, Ile, Ser, Lys, His, Asp, Asn, Glu, Gln, Trp, Tyr and Thr, relative to wild type mmIgG1 when using EU numbering index. In a preferred embodiment the first CH3 domain of the heterodimeric protein comprise a Lysine (K) at amino acid position 370 and a substitution of the amino acid residue at position 409 with an Arginine (R) and the second CH3 domain comprises a substitution of the amino acid residue at position 405 selected from Ala, Val, Leu, Ile, Ser, Lys, His, Asp, Asn, Glu, Gln, Trp, Tyr and Thr.

In a more preferred embodiment the first CH3 domain of the heterodimeric protein comprise a Lysine (K) at amino acid position 370 and a substitution of the amino acid residue at position 409 with an Arginine (R) and the second CH3 domain comprises a substitution of the amino acid residue at position 405 with a Leucine (L). In one embodiment these mutations are the only mutations compared to the relevant wild type CH3 domain.

In another embodiment the second CH3 domain further comprises an amino acid selected from the group comprising: Gly, Ala, Val, Ile, Ser, His, Asp, Glu, Gln, Trp, Phe, Tyr, Met and Thr at position 411.

In certain embodiments the second CH3 domain further comprises a Threonine (T) at position 411 so that the second CH3 domain contains a Leucine at position 405 and a Threonine at position 411.

According to the present invention, the amino acid sequences of the first and second CH3 regions of the homodimeric starting proteins are different from each other and are such that the heterodimeric interaction between said first and second CH3 regions is stronger than each of the homodimeric interactions of said first and second CH3 regions.

In one embodiment, the increased strength of the heterodimeric interaction as compared to each of the homodimeric interactions is due to CH3 modifications other than the introduction of covalent bonds, cysteine residues or charged residues.

In certain embodiments of the invention the Fc regions of the first and second polypeptides are from the same species. In other embodiments they are of the same species and isotype. In another embodiment they are of different species and/or different isotypes.

In an embodiment of the invention the Fc regions of the first and second polypeptides are both of mouse IgG1 isotype, preferably *Mus musculus* IgG1.

In another embodiment of the invention the Fc regions of the first and second polypeptides are both of mouse IgG2a isotype, preferably *Mus musculus* IgG2a.

In another embodiment of the invention the Fc regions of the first and second polypeptides are both of mouse IgG2b isotype, preferably *Mus musculus* IgG2b.

In another embodiment of the invention the Fc regions of the first and second polypeptides are both of mouse IgG2c isotype, preferably *Mus musculus* IgG2c.

In another embodiment of the invention the Fc regions of the first and second polypeptides are both of mouse IgG3 isotype, preferably *Mus musculus* IgG3.

In an embodiment of the invention the Fc regions of the first and second polypeptides are both of rat IgG1 isotype, preferably *Rattus norvegicus* IgG1.

In another embodiment of the invention the Fc regions of the first and second polypeptides are both of rat IgG2a isotype, preferably *Rattus norvegicus* IgG2a.

In another embodiment of the invention the Fc regions of the first and second polypeptides are both of rat IgG2b isotype, preferably *Rattus norvegicus* IgG2b.

In another embodiment of the invention the Fc regions of the first and second polypeptides are both of rat IgG2c isotype, preferably *Rattus norvegicus* IgG2c.

In further embodiments, the invention relates to heterodimeric protein wherein the first homodimeric protein and the second homodimeric protein are selected from the group consisting of (i) an antibody (ii) a fusion protein comprising an Fc region, such as an Fc region fused to a receptor, cytokine or hormone, (iii) an antibody conjugated to a prodrug, peptide, drug or a toxin, and (iv) a fusion protein comprising an Fc region conjugated to a prodrug, peptide, drug or a toxin.

In one embodiment the invention relates to heterodimeric protein wherein the first homodimeric protein and the second homodimeric protein are fusion proteins each comprising an Fc region which further comprises an antigen binding region, such as a Fragment antigen-binding (Fab) region or a single-chain variable fragment (scFv).

In some embodiments, said first and/or second homodimeric protein comprise, in addition to the Fc region, one or more or all of the other regions of an antibody, i.e. a CH1 region, a VH region, a CL region and/or a VL region. Thus, in one embodiment, said first homodimeric protein is a full-length antibody. In another embodiment, said second homodimeric protein is a full-length antibody.

In other embodiments, however, only one of the homodimeric proteins is a full-length antibody and the other homodimeric protein is not a full-length antibody, e.g. an Fc region without a variable region, expressed in conjunction to another protein or peptide sequence like a receptor, cytokine or hormone, or conjugated to a prodrug, peptide, a drug or a toxin. In a further embodiment, neither of the homodimeric proteins is a full-length antibody. For example, both homodimeric proteins may be Fc regions that are fused to another protein or peptide sequence like a receptor, cytokine or hormone, or conjugated to a prodrug, peptide, a drug or a toxin.

In preferred embodiments both the first and second homodimeric proteins are antibodies, preferably full-length antibodies. Preferably the first and second homodimeric proteins bind different epitopes. The epitopes may be on the same or different antigens. Preferably the epitopes are not overlapping so that the heterodimeric protein may bind both epitopes at the same time. In such embodiments, the heterodimeric proteins that are generated are bispecific antibodies. Thus, the bispecific format may be used in many ways to generate desired combinations of bispecific antibodies. In addition to being able of combining antibodies targeting different antigens in a very selective way it can be used to change a desired property, e.g. to increase CDC, by combining two different antibodies targeting the same antigen. Furthermore, it can be used to remove partial agonistic activity of an antagonistic antibody or convert an agonistic antibody into an antagonistic antibody by making a bispecific antibody thereof with an irrelevant (inactive) antibody.

In a further embodiment, one or both of the homodimeric proteins is glyco-engineered to reduce fucose and thus enhance ADCC, e.g. by addition of compounds to the culture media during antibody production as described in US2009317869 or as described in van Berkel et al. (2010) Biotechnol. Bioeng. 105:350 or by using FUT8 knockout cells, e.g. as described in Yamane-Ohnuki et al (2004) Biotechnol. Bioeng 87:614. ADCC may alternatively be optimized using the method described by Umaña et al. (1999) Nature Biotech 17:176.

In a further embodiment, one or both of the homodimeric proteins has been engineered to enhance complement activation, e.g. as described in Natsume et al. (2009) Cancer Sci. 100:2411 or Diebolder et al. (2014) Science 343:1260.

In a further embodiment, one or both of the homodimeric proteins has been engineered to reduce or increase the binding to the neonatal Fc receptor (FcRn) in order to manipulate the serum half-life of the heterodimeric protein. In one embodiment, the homodimer starting proteins are engineered by substitutions at positions corresponding to P257A or L225Q, T256N and P257A or P307H and M309Q in mmIgG1 which substitution decreases FcRn binding of those homodimers. In another embodiment, the homodimer starting proteins are engineered by substitutions at positions corresponding to T252L, T254S and T256F in mmIgG1 which substitution increases FcRn binding and serum half-life of those homodimers.

In a further embodiment, one of the homodimeric starting proteins has been engineered to not bind Protein A, thus allowing the separation of the heterodimeric protein from said homodimeric starting protein by passing the product over a protein A column. This may in particular be useful for embodiments wherein an excess of one homodimeric protein is used relative to the other homodimeric protein as starting material. In such embodiments, it may be useful to engineer the homodimeric protein that is in excess so that it loses its ability to bind protein A. Following the heterodimerization reaction, the heterodimeric protein may then be separated from a surplus of unexchanged homodimeric protein by passage over a protein A column. In one embodiment, the one homodimer starting protein is engineered by a substitution at a position corresponding to I253D in mmIgG2b which substitution decreases Protein A binding of that homodimer. In another embodiment the other homodimer is engineered by substituting the amino acid positions corresponding to P307T and Q309L of mmIgG2b which substitutions increases Protein A binding of that other homodimer. In a preferred embodiment, the first homodimer comprises the substitution I253D and the second homodimer comprises the substitutions P307T and Q309L. These substitutions may be made in any homodimeric starting protein such as for example mmIgG2a or mmIgG2b at corresponding amino acid positions. In another embodiment the other homodimer is engineered by substituting the amino acid positions corresponding to T252M and/or T254S of mmIgG1 which substitutions increases Protein A binding of those homodimers.

In a further embodiment, one of the homodimeric proteins is an Fc region or a full-length antibody recognizing a non-relevant epitope or a full-length antibody containing germline-derived sequences that have not undergone somatic hypermutation and do not bind self-antigens. In such an embodiment the heterodimeric protein functions as a monovalent antibody. In another embodiment, both homodimeric proteins comprises the same heavy chain, but only one of the homodimeric proteins contains a light chain which forms a functional antigen-binding site with said heavy chain, whereas the other homodimeric protein contains a non-functional light chain, which does not bind any antigen in combination with said heavy chain. In such an embodiment, the heterodimeric protein functions as a monovalent antibody. Such a non-functional light chain can e.g. be a germline-derived sequence that has not undergone somatic hypermutation and does not bind self-antigens.

In a further embodiment, one or both of the homodimeric proteins has been engineered to inhibit or abolish the interaction of the proteins according to the invention with Fc Receptors (FcRs) present on a wide range of effector cells, such as monocytes, or with C1q to activate the complement pathway in order to reduce unwanted effects. In one embodiment the homodimer starting proteins are engineered by substitutions at positions corresponding to D265A in mmIgG1, mmIgG2a or mmIgG2b which substitution decrease FcR and C1q binding of those homodimers In another embodiment, the homodimer starting proteins are engineered by a substitution at a position corresponding to L235E in mmIgG2a which substitution decreases FcR binding of those homodimers. In a further embodiment, the homodimer starting proteins are engineered by substitutions at positions corresponding to L234A and L235A in mmIgG2a which substitutions decrease FcR binding in those homodimers. In another embodiment, the homodimer starting proteins are engineered by a substitution at a position corresponding to N324D in mmIgG2a which substitution decreases C1q binding of those homodimers. In a further embodiment, the homodimer starting proteins are engineered by substitutions at positions corresponding to N297A or E318A in mmIgG2b which substitutions decrease FcR binding and C1q binding in those homodimers. In another embodiment, the homodimer starting proteins are engineered by substitutions at positions corresponding to E318V, K320A, K320Q, K322A, K322Q or E318A in mmIgG2b which substitutions decrease C1q binding in those homodimers. In a further embodiment, the homodimer starting proteins are engineered by deletion of amino acids at positions corresponding to 233, 234 and 235 in mmIgG2b which deletion decreases FcR binding and C1q binding in those homodimers.

In one embodiment, the first and/or second homodimeric protein is conjugated to a drug, a prodrug or a toxin or contains an acceptor group for the same. Such acceptor group may e.g. be an unnatural amino acid.

In another aspect, the invention relates to the use of a heterodimeric protein according to the invention as a research tool for exploring functions of corresponding fully human heterodimeric proteins having similar or identical binding specificity in a rodent model. Thus, the invention in one aspect relates to use of rodent, such as mouse or rat, bispecific antibodies for use in a rodent model wherein the binding part (the variable region or the CDR regions) of the molecule is obtained from a human antibody such as a human bispecific antibody for which further characterization in an animal model is of interest. In other embodiments, the binding part of the molecule may be obtained from another species or may be humanized rodent variable regions or CDR regions.

In another aspect, the invention relates to the use of a heterodimeric protein according to the invention for exploring functions such as mechanisms of action, effector functions, toxicity, unwanted mechanisms and side effects, anti-tumor efficacy, treatment efficacy, T-cell mediated anti-tumor efficacy, immune modulation, pharmacodynamics and/or pharmacokinetics of said heterodimeric protein. When the heterodimeric protein is a rodent model of a human bispecific antibody this information may be valuable for the characterization of the antibodies and for selection of clinical candidates.

In yet another aspect, the invention relates to an in vitro method for generating a heterodimeric protein of the invention, said method comprising the following steps:

a) providing a first homodimeric protein comprising a first variable region having a first binding specificity, a hinge region, and a first Fc region, said first Fc region comprising a first CH3 domain; and b) providing a second homodimeric protein comprising a second variable region having a second binding specificity, a hinge region, and a second Fc region, said second Fc region comprising a second CH3 domain, wherein the variable regions may origin from any species and the Fc regions origin from a rodent species, and wherein the first CH3 domain comprises an amino acid selected from Gly, Ala, Val, Leu, Ile, Ser, Lys, Arg, His, Asp, Asn, Glu, Gln, Trp, Phe, Tyr and Met at position 370 and a substitution of the amino acid residue at position 409 selected from Gly, Ala, Val, Ile, Ser, Arg, His, Asp, Asn, Glu, Gln, Trp, Phe, Tyr and Thrs, and the second CH3 domain comprises a substitution of the amino acid residue at position 405 selected from Ala, Val, Leu, Ile, Ser, Lys, His, Asp, Asn, Glu, Gln, Trp, Tyr and Thr, relative to the wild type IgG1 isotype from said rodent when using EU-index numbering and wherein the sequences of said first and second CH3 regions are different and are such that a heterodimeric interaction between said first and second CH3 regions is stronger than each of the homodimeric interactions of said first and second CH3 regions, c) incubating said first homodimeric protein together with said second homodimeric protein under reducing conditions sufficient to allow the cysteines in the hinge region to undergo disulfide-bond isomerization, and d) obtaining said heterodimeric protein.

The sequence of the hinge region of the homodimeric starting proteins may vary. In one embodiment both hinge regions are wild type hinge regions of the same isotype and species as the rest of the Fc regions. Thus, where the Fc region is obtained from mmIgG1, the hinge region is likewise obtained from mmIgG1.

In many embodiments wherein the first and said second homodimeric proteins are antibodies, said antibodies further comprise light chains. Said light chains may be different, i.e. differ in sequence and each form a functional antigen-binding domain with only one of the heavy chains. In another embodiment, however, said first and second homodimeric proteins are heavy-chain antibodies, which do not need a light chain for antigen binding, see e.g. Hamers-Casterman (1993) Nature 363:446.

As described above, step c) of the method of the invention comprises incubating said first protein together with said second protein under reducing conditions sufficient to allow the cysteines in the hinge region to undergo disulfide-bond isomerisation. Examples of suitable conditions are given herein. The minimal requirements for the cysteines in the hinge region for undergoing disulfide-bond isomerisation may differ depending on the homodimeric starting proteins, in particular depending on the exact sequence in the hinge region. It is important that the respective homodimeric interactions of said first and second CH3 regions are sufficiently weak to allow cysteines in the hinge region to undergo disulfide-bond isomerisation under the given conditions.

In one embodiment, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione (GSH), tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl) phosphine.

In a further embodiment, step c) comprises incubation for at least 90 min at a temperature of at least 20° C. in the presence of at least 25 mM 2-mercaptoethylamine or in the presence of at least 0.5 mM dithiothreitol. The incubation may be performed at a pH of from 5 to 8, such as at pH 7.0 or at pH 7.4.

In a further embodiment, step d) comprises restoring the conditions to become non-reducing or less reducing, for example by removal of a reducing agent, e.g. by desalting.

In some embodiments, the method of the invention yields an antibody product wherein more than 80%, such as more than 90%, e.g. more than 95%, such as more than 99% of the antibody molecules are the desired bispecific antibodies, when measured by HIC analysis. HIC analysis may be performed as described in example 8.

EXAMPLES

TABLE 1

Sequences

| SEQ ID | SEQ Desc. | SEQ. |
|---|---|---|
| SEQ ID NO: 1 | Human IgG1 (Accession number P01857) CH1 | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRV |
| SEQ ID NO: 2 | Human IgG1 CH2 | ELLGGPSVFLFPPKPKDTLMISRTPEVTCVVVDVSHEDPEVK FNWYVDGVEVHNAKTKPREEQYNSTYRVVSVLTVLHQDWLNG KEYKCKVSNKALPAPIEKTISKAK |
| SEQ ID NO: 3 | Human kappa (Accession number J00241) CL | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC |
| SEQ ID NO: 4 | Mouse IgG1 (Accession number J00453) CH1 | AKTTPPSVYPLAPGSAAQTNSMVTLGCLVKGYFPEPVTVTWN SGSLSSGVHTFPAVLESDLYTLSSSVTVPSSPRPSETVTCNV AHPASSTKVDKKI |
| SEQ ID NO: 5 | Mouse IgG2a (Accession number V00825) CH1 | AKTTAPSVYPLAPVCGDTTGSSVTLGCLVKGYFPEPVTLTWN SGSLSSGVHTFPAVLQSDLYTLSSSVTVTSSTWPSQSITCNV AHPASSTKVDKKI |
| SEQ ID NO: 6 | Mouse IgG2b (Accession number V00763) CH1 | AKTTPPSVYPLAPGCGDTTGSSVTSGCLVKGYFPEPVTVTWN SGSLSSSVHTFPALLQSGLYTMSSSVTVPSSTWPSQTVTCSV AHPASSTTVDKKL |

TABLE 1-continued

Sequences

| SEQ ID | SEQ Desc. | SEQ. |
|---|---|---|
| SEQ ID NO: 7 | Mouse IgG3 (Accession number X00915) CH1 | ATTTAPSVYPLVPGCSDTSGSSVTLGCLVKGYFPEPVTVKWN YGALSSGVRTVSSVLQSGFYSLSSLVTVPSSTWPSQTVICNV AHPASKTELIKRI |
| SEQ ID NO: 8 | Mouse IgG1 CH2 | VPEVSSVFIFPPKPKDVLTITLTPKVTCVVVDISKDDPEVQF SWFVDDVEVHTAQTQPREEQFNSTFRSVSELPIMHQDWLNGK EFKCRVNSAAFPAPIEKTISKTK |
| SEQ ID NO: 9 | Mouse IgG2a CH2 | APNLLGGPSVFIFPPKIKDVLMISLSPIVTCVVVDVSEDDPD VQISWFVNNVEVHTAQTQTHREDYNSTLRVVSALPIQHQDWM SGKEFKCKVNNKDLPAPIERTISKPK |
| SEQ ID NO: 10 | Mouse IgG2b CH2 | APNLEGGPSVFIFPPNIKDVLMISLTPKVTCVVVDVSEDDPD VQISWFVNNVEVHTAQTQTHREDYNSTIRVVSTLPIQHQDWM SGKEFKCKVNNKDLPSPIERTISKIK |
| SEQ ID NO: 11 | Mouse IgG3 CH2 | PGNILGGPSVFIFPPKPKDALMISLTPKVTCVVVDVSEDDPD VHVSWFVDNKEVHTAWTQPREAQYNSTFRVVSALPIQHQDWM RGKEFKCKVNNKALPAPIERTISKPK |
| SEQ ID NO: 12 | Mouse kappa (Accession number V00807) CL | RADAAPTVSIFPPSSEQLTSGGASVVCFLNNFYPKDINVKWK IDGSERQNGVLNSWTDQDSKDSTYSMSSTLTLTKDEYERHNS YTCEATHKTSTSPIVKSFNRNEC |
| SEQ ID NO: 13 | Rat IgG1 (Accession number AABR03048905) CH1 | AETTAPSVYPLAPGTALKSNSMVTLGCLVKGYFPEPVTVTWN SGALSSGVHTFPAVLQSGLYTLTSSVTVPSSTWPSQTVTCNV AHPASSTKVDKKI |
| SEQ ID NO: 14 | Rat IgG2a (Accession number AABR03049560) CH1 | AETTAPSVYPLAPGTALKSNSMVTLGCLVKGYFPEPVTVTWN SGALSSGVHTFPAVLQSGLYTLTSSVTVPSSTWSSQAVTCNV AHPASSTKVDKKI |
| SEQ ID NO: 15 | Rat IgG2b (Accession number AABR03048905) CH1 | AQTTAPSVYPLAPGCGDTTSSTVTLGCLVKGYFPEPVTVTWN SGALSSDVHTFPAVLQSGLYTLTSSVTSSTWPSQTVTCNVAH PASSTKVDKKV |
| SEQ ID NO: 16 | Rat IgG2c (Accession number AABR03049912) CH1 | ARTTAPSVYPLVPGCSGTSGSLVTLGCLVKGYFPEPVTVKWN SGALSSGVHTFPAVLQSGLYTLSSSVTVPSSTWSSQTVTCSV AHPATKSNLIKRI |
| SEQ ID NO: 17 | Rat IgG1 CH2 | GSEVSSVFIFPPKPKDVLTITLTPKVTCVVVDISQDDPEVHF SWFVDDVEVHTAQTRPPEEQFNSTFRSVSELPILHQDWLNGR TFRCKVTSAAFPSPIEKTISKPE |
| SEQ ID NO: 18 | Rat IgG2a CH2 | GSEVSSVFIFPPKTKDVLTITLTPKVTCVVVDISQNDPEVRF SWFIDDVEVHTAQTHAPEKQSNSTLRSVSELPIVHRDWLNGK TFKCKVNSGAFPAPIEKSISKPE |
| SEQ ID NO: 19 | Rat IgG2b CH2 | VPELLGGPSVFIFPPKPKDILLISQNAKVTCVVVDVSEEEPD VQFSWFVNNVEVHTAQTQPREEQYNSTFRVVSALPIQHQDWM SGKEFKCKVNNKALPSPIEKTISKPK |
| SEQ ID NO: 20 | Rat IgG2c CH2 | CDDNLGRPSVFIFPPKPKDILMITLTPKVTCVVVDVSEEEPD VQFSWFVDNVRVFTAQTQPHEEQLNGTFRVVSTLHIQHQDWM SGKEFKCKVNNKDLPSPIEKTISKPR |
| SEQ ID NO: 21 | Rat kappa (Accession number V01241) CL | RADAAPTVSIFPPSTEQLATGGASVVCLMNNFYPRDISVKWK IDGTERRDGVLDSVTDQDSKDSTYSMSSTLSLTKADYESHNL YTCEVVHKTSSSPVVKSFNRNEC |
| SEQ ID NO: 22 | Mouse IGHG1 | KTTPPSVYPLAPGSAAQTNSMVTLGCLVKGYFPEPVTVTWNS GSLSSGVHTFPAVLESDLYTLSSSVTVPSSPRPSETVTCNVA HPASSTKVDKKIVPRDCGCKPCICTVPEVSSVFIFPPKPKDV LTITLTPKVTCVVVDISKDDPEVQFSWFVDDVEVHTAQTQPR EEQFNSTFRSVSELPIMHQDWLNGKEFKCRVNSAAFPAPIEK TISKTKGRPKAPQVYTIPPPKEQMAKDKVSLTCMITDFFPED ITVEWQWNGQPAENYKNTQPIMNTNGSYFVYSKLNVQKSNWE AGNTFTCSVLHEGLHNHHTEKSLSHSPGK |

TABLE 1-continued

Sequences

| SEQ ID | SEQ Desc. | SEQ. |
|---|---|---|
| SEQ ID NO: 23 | Mouse IGHG2A | AKTTAPSVYPLAPVCGDTTGSSVTLGCLVKGYFPEPVTLTWN SGSLSSGVHTFPAVLQSDLYTLSSSVTVTSSTWPSQSITCNV AHPASSTKVDKKIEPRGPTIKPCPPCKCPAPNLLGGPSVFIF PPKIKDVLMISLSPIVTCVVVDVSEDDPDVQISWFVNNVEVH TAQTQTHREDYNSTLRVVSALPIQHQDWMSGKEFKCKVNNKD LPAPIERTISKPKGSVRAPQVYVLPPPEEEMTKKQVTLTCMV TDFMPEDIYVEWTNNGKTELNYKNTEPVLDSDGSYFMYSKLR VEKKNWVERNSYSCSVVHEGLHNHHTTKSFSRTPGK |
| SEQ ID NO: 24 | Mouse IGHG2B | AKTTPPSVYPLAPGCGDTTGSSVTSGCLVKGYFPEPVTVTWN SGSLSSSVHTFPALLQSGLYTMSSSVTVPSSTWPSQTVTCSV AHPASSTTVDKKLEPSGPISTINPCPPCKECHKCPAPNLEGG PSVFIFPPNIKDVLMISLTPKVTCVVVDVSEDDPDVQISWFV NNVEVHTAQTQTHREDYNSTIRVVSTLPIQHQDWMSGKEFKC KVNNKDLPSPIERTISKIKGLVRAPQVYTLPPPAEQLSRKDV SLTCLVVGFNPGDISVEWTSNGHTEENYKDTAPVLDSDGSYF IYSKLNMKTSKWEKTDSFSCNVRHEGLKNYYLKKTISRSPGK |
| SEQ ID NO: 25 | Mouse IGHG2C | KTTAPSVYPLAPVCGGTTGSSVTLGCLVKGYFPEPVTLTWNS GSLSSGVHTFPALLQSGLYTLSSSVTVTSNTWPSQTITCNVA HPASSTKVDKKIEPRVPITQNPCPPLKECPPCAAPDLLGGPS VFIFPPKIKDVLMISLSPMVTCVVVDVSEDDPDVQISWFVNN VEVHTAQTQTHREDYNSTLRVVSALPIQHQDWMSGKEFKCKV NNRALPSPIEKTISKPRGPVRAPQVYVLPPPAEEMTKKEFSL TCMITGFLPAEIAVDWTSNGRTEQNYKNTATVLDSDGSYFMY SKLRVQKSTWERGSLFACSVVHEVLHNHLTTKTISRSLGK |
| SEQ ID NO: 26 | Mouse IGHG3 | ATTTAPSVYPLVPGCSDTSGSSVTLGCLVKGYFPEPVTVKWN YGALSSGVRTVSSVLQSGFYSLSSLVTVPSSTWPSQTVICNV AHPASKTELIKRIEPRIPKPSTPPGSSCPPGNILGGPSVFIF PPKPKDALMISLTPKVTCVVVDVSEDDPDVHVSWFVDNKEVH TAWTQPREAQYNSTFRVVSALPIQHQDWMRGKEFKCKVNNKA LPAPIERTISKPKGRAQTPQVYTIPPPREQMSKKKVSLTCLV TNFFSEAISVEWERNGELEQDYKNTPPILDSDGTYFLYSKLT VDTDSWLQGEIFTCSVVHEALHNHHTQKNLSRSPGK |
| SEQ ID NO: 27 | Mouse IGKC | ADAAPTVSIFPPSSEQLTSGGASVVCFLNNFYPKDINVKWKI DGSERQNGVLNSWTDQDSKDSTYSMSSTLTLTKDEYERHNSY TCEATHKTSTSPIVKSFNRNEC |
| SEQ ID NO: 28 | Rat IGHG1 | AETTAPSVYPLAPGTALKSNSMVTLGCLVKGYFPEPVTVTWN SGALSSGVHTFPAVLQSGLYTLTSSVTVPSSTWPSQTVTCNV AHPASSTKVDKKIVPRNCGGDCKPCICTGSEVSSVFIFPPKP KDVLTITLTPKVTCVVVDISQDDPEVHFSWFVDDVEVHTAQT RPPEEQFNSTFRSVSELPILHQDWLNGRTFRCKVTSAAFPSP IEKTISKPEGRTQVPHVYTMSPTKEEMTQNEVSITCMVKGFY PPDIYVEWQMNGQPENYKNTPPTMDTDGSYFLYSKLNVKKE KWQQGNTFTCSVLHEGLHNHHTEKSLSHSPGK |
| SEQ ID NO: 29 | Rat IGHG2A | AETTAPSVYPLAPGTALKSNSMVTLGCLVKGYFPEPVTVTWN SGALSSGVHTFPAVLQSGLYTLTSSVTVPSSTWSSQAVTCNV AHPASSTKVDKKIVPRECNPCGCTGSEVSSVFIFPPPKTKDVL TITLTPKVTCVVVDISQNDPEVRFSWFIDDVEVHTAQTHAPE KQSNSTLRSVSELPIVHRDWLNGKTFKCKVNSGAFPAPIEKS ISKPEGTPRGPQVYTMAPPKEEMTQSQVSITCMVKGFYPPDI YTEWKMNGQPQENYKNTPPTMDTDGSYFLYSKLNVKKETWQQ GNTFTCSVLHEGLHNHHTEKSLSHSPGK |
| SEQ ID NO: 30 | Rat IGHG2B | AQTTAPSVYPLAPGCGDTTSSTVTLGCLVKGYFPEPVTVTWN SGALSSDVHTFPAVLQSGLYTLTSSVTSSTWPSQTVTCNVAH PASSTKVDKKVERRNGGIGHKCPTCPTCHKCPVPELLGGPSV FIFPPKPKDILLISQNAKVTCVVVDVSEEEPDVQFSWFVNNV EVHTAQTQPREEQYNSTFRVVSALPIQHQDWMSGKEFKCKVN NKALPSPIEKTISKPKGLVRKPQVYVMGPPTEQLTEQTVSLT CLTSGFLPNDIGVEWTSNGHIEKNYKNTEPVMDSDGSFFMYS KLNVERSRWDSRAPFVCSVVHEGLHNHHVEKSISRPPGK |
| SEQ ID NO: 31 | Rat IGHG2C | ARTTAPSVYPLVPGCSGTSGSLVTLGCLVKGYFPEPVTVKWN SGALSSGVHTFPAVLQSGLYTLSSSVTVPSSTWSSQTVTCSV AHPATKSNLIKRIEPRRPKPRPPTDICSCDDNLGRPSVFIFP PKPKDILMITLTPKVTCVVVDVSEEEPDVQFSWFVDNRVFT AQTQPHEEQLNGTFRVVSTLHIQHQDWMSGKEFKCKVNNKDL PSPIEKTISKPRGKARTPQVYTIPPPREQMSKNKVSLTCMVT SFYPASISVEWERNGELEQDYKNTLPVLDSDESYFLYSKLSV DTDSWMRGDIYTCSVVHEALHNHHTQKNLSRSPGK |

TABLE 1-continued

Sequences

| SEQ ID | SEQ Desc. | SEQ. |
|---|---|---|
| SEQ ID NO: 32 | Rat IGKC | RADAAPTVSIFPPSTEQLATGGASVVCLMNNFYPRDISVKWK<br>IDGTERRDGVLDSVTDQDSKDSTYSMSSTLSLTKADYESHNL<br>YTCEVVHKTSSSPVVKSFNRNEC |
| SEQ ID NO: 33 | Mouse IGHG1 CH1 | AKTTPPSVYPLAPGSAAQTNSMVTLGCLVKGYFPEPVTVTWN<br>SGSLSSGVHTFPAVLESDLYTLSSSVTVPSSPRPSETVTCNV<br>AHPASSTKVDKKI |
| SEQ ID NO: 34 | Mouse IGHG2A CH1 | AKTTAPSVYPLAPVCGDTTGSSVTLGCLVKGYFPEPVTLTWN<br>SGSLSSGVHTFPAVLQSDLYTLSSSVTVTSSTWPSQSITCNV<br>AHPASSTKVDKKI |
| SEQ ID NO: 35 | Mouse IGHG2B CH1 | AKTTPPSVYPLAPGCGDTTGSSVTSGCLVKGYFPEPVTVTWN<br>SGSLSSSVHTFPALLQSGLYTMSSSVTVPSSTWPSQTVTCSV<br>AHPASSTTVDKKL |
| SEQ ID NO: 36 | Mouse IGHG2c CH1 | AKTTAPSVYPLAPVCGGTTGSSVTLGCLVKGYFPEPVTLTWN<br>SGSLSSGVHTFPALLQSGLYTLSSSVTVTSNTWPSQTITCNV<br>AHPASSTKVDKKI |
| SEQ ID NO: 37 | Mouse IGHG3 CH1 | ATTTAPSVYPLVPGCSDTSGSSVTLGCLVKGYFPEPVTVKWN<br>YGALSSGVRTVSSVLQSGFYSLSSLVTVPSSTWPSQTVICNV<br>AHPASKTELIKRI |
| SEQ ID NO: 38 | Mouse IGHG1 HINGE | VPRDCGCKPCICT |
| SEQ ID NO: 39 | Mouse IGHG2A HINGE | EPRGPTIKPCPPCKCP |
| SEQ ID NO: 40 | Mouse IGHG2B HINGE | EPSGPISTINPCPPCKECHKCP |
| SEQ ID NO: 41 | Mouse IGHG2C HINGE | EPRVPITQNPCPPLKECPPCA |
| SEQ ID NO: 42 | Mouse IGHG3 HINGE | EPRIPKPSTPPGSSCP |
| SEQ ID NO: 43 | Mouse IGHG2c CH2 | APDLLGGPSVFIFPPKIKDVLMISLSPMVTCVVVDVSEDDPD<br>VQISWFVNNVEVHTAQTQTHREDYNSTLRVVSALPIQHQDWM<br>SGKEFKCKVNNRALPSPIEKTISKPR |
| SEQ ID NO: 44 | Mouse IGHG1 CH3 | GRPKAPQVYTIPPPKEQMAKDKVSLTCMITDFFPEDITVEWQ<br>WNGQPAENYKNTQPIMNTNGSYFVYSKLNVQKSNWEAGNTFT<br>CSVLHEGLHNHHTEKSLSHSPGK |
| SEQ ID NO: 45 | Mouse IGHG2A CH3 | GSVRAPQVYVLPPPEEEMTKKQVTLTCMVTDFMPEDIYVEWT<br>NNGKTELNYKNTEPVLDSDGSYFMYSKLRVEKKNWVERNSYS<br>CSVVHEGLHNHHTTKSFSRTPGK |
| SEQ ID NO: 46 | Mouse IGHG2B CH3 | GLVRAPQVYTLPPPAEQLSRKDVSLTCLVVGFNPGDISVEWT<br>SNGHTEENYKDTAPVLDSDGSYFIYSKLNMKTSKWEKTDSFS<br>CNVRHEGLKNYYLKKTISRSPGK |
| SEQ ID NO: 47 | Mouse IGHG2c CH3 | GPVRAPQVYVLPPPAEEMTKKEFSLTCMITGFLPAEIAVDWT<br>SNGRTEQNYKNTATVLDSDGSYFMYSKLRVQKSTWERGSLFA<br>CSVVHEVLHNHLTTKTISRSLGK |
| SEQ ID NO: 48 | Mouse IGHG3 CH3 | GRAQTPQVYTIPPPREQMSKKKVSLTCLVTNFFSEAISVEWE<br>RNGELEQDYKNTPPILDSDGTYFLYSKLTVDTSWLQGEIFT<br>CSVVHEALHNHHTQKNLSRSPGK |
| SEQ ID NO: 49 | Rat IGHG1 CH1 | AETTAPSVYPLAPGTALKSNSMVTLGCLVKGYFPEPVTVTWN<br>SGALSSGVHTFPAVLQSGLYTLTSSVTVPSSTWPSQTVTCNV<br>AHPASSTKVDKKI |
| SEQ ID NO: 50 | Rat IGHG2A CH1 | AETTAPSVYPLAPGTALKSNSMVTLGCLVKGYFPEPVTVTWN<br>SGALSSGVHTFPAVLQSGLYTLTSSVTVPSSTWSSQAVTCNV<br>AHPASSTKVDKKI |
| SEQ ID NO: 51 | Rat IGHG2B CH1 | AQTTAPSVYPLAPGCGDTTSSTVTLGCLVKGYFPEPVTVTWN<br>SGALSSDVHTFPAVLQSGLYTLTSSVTSSTWPSQTVTCNVAH<br>PASSTKVDKKV |
| SEQ ID NO: 52 | Rat IGHG2c CH1 | ARTTAPSVYPLVPGCSGTSGSLVTLGCLVKGYFPEPVTVKWN<br>SGALSSGVHTFPAVLQSGLYTLSSSVTVPSSTWSSQTVTCSV<br>AHPATKSNLIKRI |

TABLE 1-continued

Sequences

| SEQ ID | SEQ Desc. | SEQ. |
|---|---|---|
| SEQ ID NO: 53 | Rat IGHG1 HINGE | VPRNCGGDCKPCICT |
| SEQ ID NO: 54 | Rat IGHG2A HINGE | VPRECNPCGCT |
| SEQ ID NO: 55 | Rat IGHG2B HINGE | ERRNGGIGHKCPTCPTCHKCP |
| SEQ ID NO: 56 | Rat IGHG2c HINGE | EPRRPKPRPPTDICS |
| SEQ ID NO: 57 | Rat IGHG1 CH3 | GRTQVPHVYTMSPTKEEMTQNEVSITCMVKGFYPPDIYVEWQ<br>MNGQPQENYKNTPPTMDTDGSYFLYSKLNVKKEKWQQGNTFT<br>CSVLHEGLHNHHTEKSLSHSPGK |
| SEQ ID NO: 58 | Rat IGHG2A CH3 | GTPRGPQVYTMAPPKEEMTQSQVSITCMVKGFYPPDIYTEWK<br>MNGQPQENYKNTPPTMDTDGSYFLYSKLNVKKETWQQGNTFT<br>CSVLHEGLHNHHTEKSLSHSPGK |
| SEQ ID NO: 59 | Rat IGHG2B CH3 | GLVRKPQVYVMGPPTEQLTEQTVSLTCLTSGFLPNDIGVEWT<br>SNGHIEKNYKNTEPVMDSDGSFFMYSKLNVERSRWDSRAPFV<br>CSVVHEGLHNHHVEKSISRPP |
| SEQ ID NO: 60 | Rat IGHG2c CH3 | GKARTPQVYTIPPPREQMSKNKVSLTCMVTSFYPASISVEWE<br>RNGELEQDYKNTLPVLDSDESYFLYSKLSVDTDSWMRGDIYT<br>CSVVHEALHNHHTQKNLSRSPGK |
| SEQ ID NO: 61 | Human IgG1 Hinge | EPKSCDKTHTCPPCP |
| SEQ ID NO: 62 | VH HER2-169 | QVQLVQSGAEVKKPGASVKVSCKASGYTFTNYGISWVRQAPG<br>QGLEWMGWLSAYSGNTIYAQKLQGRVTMTTDTSTTTAYMELR<br>SLRSDDTAVYYCARDRIVVRPDYFDYWGQGTLVTVSS |
| SEQ ID NO: 63 | VL HER2-169 | EIVLTQSPATLSLSPGERATLSCRASQSVSSYLAWYQQKPGQ<br>APRLLIYDASNRATGIPARFSGSGSGTDFTLTISSLEPEDFA<br>VYYCQQRSNWPRTFGQGTKVEIK |
| SEQ ID NO: 64 | VH 145-2C11 | EVQLVESGGGLVQPGKSLKLSCEASGFTFSGYGMHWVRQAPG<br>RGLESVAYITSSSINIKYADAVKGRFTVSRDNAKNLLFLQMN<br>ILKSEDTAMYYCARFDWDKNYWGQGTMVTVSS |
| SEQ ID NO: 65 | VL 145-2C11 | DIQMTQSPSSLPASLGDRVTINCQASQDISNYLNWYQQKPGK<br>APKLLIYYTNKLADGVPSRFSGSGSGRDSSFTISSLESEDIG<br>SYYCQQYYNYPWTFGPGTKLEIK |
| SEQ ID NO: 66 | VH CTA99 | EVQLQQSGAELVRPGALVKLSCKTSGFNIKDYFLHWVRQRPD<br>QGLEWIGWINPDNGNTVYDPKFQGTASLTADTSSNTVYLQLS<br>GLTSEDTAVYFCTRRDYTYEKAALDYWGQGASVIVSS |
| SEQ ID NO: 67 | VL CTA99 | AIQMSQSPASLSASVGETVTITCRASGNIYNYLAWYQQKQGK<br>SPHLLVYDAKTLADGVPSRFSGSGSGTQYSLKISSLQTEDSG<br>NYYCQHFWSLPFTFGSGTKLEIK |
| SEQ ID NO: 68 | VH b12 | QVQLVQSGAEVKKPGASVKVSCQASGYRFSNFVIHWVRQAPG<br>QRFEWMGWINPYNGNKEFSAKFQDRVTFTADTSANTAYMELR<br>SLRSADTAVYYCARVGPYSWDDSPQDNYYMDVWGKGTTVIVS<br>S |
| SEQ ID NO: 69 | VL b12 | EIVLTQSPGTLSLSPGERATFSCRSSHSIRSRRVAWYQHKPG<br>QAPRLVHGVSNRASGISDRFSGSGSGTDFTLTITRVEPEDF<br>ALYYCQVYGASSYTFGQGTKLERK |

Example 1: Expression Vectors for the Expression of Human IgG1-2F8, IgG1-7D8 and Variants Thereof The VH and VL coding regions of HuMab 2F8 (WO 02/100348) and HuMab 7D8 (WO 04/035607) were cloned in the expression vector pConG1f (containing the genomic sequence of the human IgG1f allotype constant region (Lonza Biologics)) for the production of the human IgG1 heavy chain and pConKappa (containing the human kappa light chain constant region, Lonza Biologics) for the production of the kappa light chain. Alternatively, in follow-up constructs, vectors were used containing the fully codon-optimized coding regions of the heavy chain in the pcDNA3.3 vector (Invitrogen) or the human kappa light chain of HuMab 2F8 or HuMab 7D8 in the pcDNA3.3 vector. The heavy chain constant region amino acid sequences as used were the following:

```
Human IgG1 (Accession number P01857) CH1,
SEQ ID NO: 1:
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRV
```

Human IgG1 Hinge sequence is described in Table 1 (SEQ ID NO: 61) and FIG. 1B.

```
Human IgG1 CH2, SEQ ID NO: 2:
ELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPA
PIEKTISKAK
```

Human IgG1 CH3 sequences are described in FIG. 1C.

```
Human kappa (Accession number J00241) CL,
                                              SEQ ID NO: 3
RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSS
PVTKSFNRGEC
```

To introduce mutations in the CH3 regions of the antibody heavy chains, i.e. F405L or K409R (EU-numbering convention as described in Kabat et al., Sequences of Proteins of Immunological Interest, 5th Ed. Public Health Service, National Institutes of Health, Bethesda, Md. (1991) is used throughout), Quickchange site-directed mutagenesis kit (Stratagene, La Jolla, Calif.) was used according to the manufacturer's recommendations. Alternatively the constructs were fully synthesized or VH regions were cloned in a vector already containing the specific amino acid encoding substitutions.

Example 2: Expression Vectors for the Expression of Chimeric IgG1-2F8-CH3 (mmG1), IgG1-2F8-CH3 (mmG2a), IgG1-2F8-CH3 (mmG2b), IgG1-2F8-CH3 (mmG3), IgG1-7D8-CH3 (mmG1), IgG1-7D8-CH3 (mmG2a), IgG1-7D8-CH3 (mmG2b) and IgG1-7D8-CH3 (mmG3) Constructs and Variants Thereof Vectors containing the coding regions for the human IgG1 CH1-hinge-CH2 regions, mouse CH3 (IgG1, IgG2a, IgG2b or IgG3) regions and human kappa light chains constant regions and the human VH and VL regions of Humab 2F8 and 7D8 were synthesized, fully codon-optimized and inserted in separate (heavy chain and light chain) pcDNA3.3 vectors. The heavy chain constant region sequences as used were the following:

Human IgG1 CH1-Hinge-CH2 sequences (SEQ ID Nos: 1, 61 and 2).

Mouse IgG1, IgG2a, IgG2b and IgG3 CH3 sequences (SEQ ID NOs: 44, 45, 46 and 48).

To introduce mutations in the CH3 regions of the antibody heavy chains, i.e. F405L, K409R, V370K, T370K, N411T or R411T, Quickchange site-directed mutagenesis kit (Stratagene, La Jolla, Calif.) was used according to the manufacturer's recommendations. Alternatively the constructs were fully synthesized or VH regions were cloned in a vector already containing the specific amino acid encoding substitutions.

Example 3: Expression Vectors for the Expression of Chimeric mmIgG1-2F8, mmIgG2a-2F8 mmIgG2b-2F8, mmIgG3-2F8, mmIgG1-7D8, mmIgG2a-7D8 mmIgG2b-7D8 and mmIgG3-7D8 Constructs and Variants Thereof Vectors containing the coding regions for the mouse (*Mus musculus*) IgG1, mouse IgG2a, mouse IgG2b, mouse IgG3 heavy and kappa light chains constant regions and the human VH and VL regions of Humab 2F8 and 7D8 were synthesized, fully codon-optimized and inserted in separate (heavy chain and light chain) pcDNA3.3 vectors. The heavy chain constant region amino acid sequences as used were the following:

```
Mouse IgG1 (Accession number J00453) CH1,
                                              SEQ ID NO: 4
AKTTPPSVYPLAPGSAAQTNSMVTLGCLVKGYFPEPVTVTWNSGSLSSGV
HTFPAVLESDLYTLSSSVTVPSSPRPSETVTCNVAHPASSTKVDKKI Mouse IgG2a (Accession number V00825) CH1,
                                              SEQ ID NO: 5
AKTTAPSVYPLAPVCGDTTGSSVTLGCLVKGYFPEPVTLTWNSGSLSSGV
HTFPAVLQSDLYTLSSSVTVTSSTWPSQSITCNVAHPASSTKVDKKI Mouse IgG2b (Accession number V00763) CH1
                                              SEQ ID NO: 6
AKTTPPSVYPLAPGCGDTTGSSVTSGCLVKGYFPEPVTVTWNSGSLSSSV
HTFPALLQSGLYTMSSSVTVPSSTWPSQTVTCSVAHPASSTTVDKKL Mouse IgG3 (Accession number X00915) CH1,
                                              SEQ ID NO: 7
ATTTAPSVYPLVPGCSDTSGSSVTLGCLVKGYFPEPVTVKWNYGALSSGV
RTVSSVLQSGFYSLSSLVTVPSSTWPSQTVICNVAHPASKTELIKRI
```

Mouse IgG1, IgG2a, IgG2b and IgG3 Hinge sequences are described in Table 1 and FIG. 1B.

```
Mouse IgG1 CH2,
                                              SEQ ID NO: 8
VPEVSSVFIFPPKPKDVLTITLTPKVTCVVVDISKDDPEVQFSWFVDDV
EVHTAQTQPREEQFNSTFRSVSELPIMHQDWLNGKEFKCRVNSAAFPAP
IEKTISKTK Mouse IgG2a CH2,
                                              SEQ ID NO: 9
APNLLGGPSVFIFPPKIKDVLMISLSPIVTCVVVDVSEDDPDVQISWFV
NNVEVHTAQTQTHREDYNSTLRVVSALPIQHQDWMSGKEFKCKVNNKDL
PAPIERTISKPK Mouse IgG2b CH2,
                                              SEQ ID NO: 10
APNLEGGPSVFIFPPNIKDVLMISLTPKVTCVVVDVSEDDPDVQISWFV
NNVEVHTAQTQTHREDYNSTIRVVSTLPIQHQDWMSGKEFKCKVNNKDL
PSPIERTISKIK
```

Mouse IgG3 CH2,

SEQ ID NO: 11
PGNILGGPSVFIFPPKPKDALMISLTPKVTCVVVDVSEDDPDVHVSWFV
DNKEVHTAWTQPREAQYNSTFRVVSALPIQHQDWMRGKEFKCKVNNKAL
PAPIERTISKPK

Mouse IgG1, IgG2a, IgG2b and IgG3 CH3 sequences are described in FIG. 1C.

Mouse kappa (Accession number V00807) CL,
SEQ ID NO: 12
RADAAPTVSIFPPSSEQLTSGGASVVCFLNNFYPKDINVKWKIDGSE
RQNGVLNSWTDQDSKDSTYSMSSTLTLTKDEYERHNSYTCEATHKTST
SPIVKSFNRNEC To introduce mutations in the CH3 regions of the antibody heavy chains, i.e. F405L, K409R, V370K, T370K, N411T or R411T, Quickchange site-directed mutagenesis kit (Stratagene, La Jolla, Calif.) was used according to the manufacturer's recommendations. Alternatively the constructs were fully synthesized or VH regions were cloned in a vector already containing the specific amino acid encoding substitutions. Likewise, mutations were introduced in the CH2 regions of the heavy chains, i.e. L234A-L235A, L235E, D265A, N324D, in order to inactivate the antibodies effector functions (Nimmerjahn et al, Immunity 2005, 23:41, Clynes et al, Nature Med 2000, 6:443, Duncan et al, Nature 1988, 332:563, Baudino et al, J Immunol 2008, 180:1948, Li et al, Int Immunopharm 2006, 6:880, Baudino et al, J Immunol 2008, 181: 6664, Nose et al, Eur J Immunol 1989, 19:2179).

Example 4: Expression Vectors for the Expression of Chimeric rnIgG1-2F8, rnIgG2a-2F8, rnIgG2b-2F8, rnIgG2c-2F8, rnIgG1-7D8, rnIgG2a-7D8, rnIgG2b-7D8 and rnIgG2c-7D8 Constructs and Variants Thereof Vectors containing the coding regions for the rat (*Rattus norvegicus*) IgG1, rat IgG2a, rat IgG2b, rat IgG2c heavy and kappa light chains constant regions and the VH and VL regions of Humab 2F8 and 7D8 were synthesized, fully codon-optimized and inserted in separate (heavy chain and light chain) pcDNA3.3 vectors. The heavy chain constant region amino acid sequences as used were the following:

Rat IgG1 (Accession number AABR03048905) CH1,
SEQ ID NO: 13
AETTAPSVYPLAPGTALKSNSMVTLGCLVKGYFPEPVTVTWNSGALSSG
VHTFPAVLQSGLYTLTSSVTVPSSTWPSQTVTCNVAHPASSTKVDKKI Rat IgG2a (Accession number AABR03049560) CH1,
SEQ ID NO: 14
AETTAPSVYPLAPGTALKSNSMVTLGCLVKGYFPEPVTVTWNSGALSSG
VHTFPAVLQSGLYTLTSSVTVPSSTWSSQAVTCNVAHPASSTKVDKKI Rat IgG2b (Accession number AABR03048905) CH1,
SEQ ID NO: 15
AQTTAPSVYPLAPGCGDTTSSTVTLGCLVKGYFPEPVTVTWNSGALSSD
VHTFPAVLQSGLYTLTSSVTSSTWPSQTVTCNVAHPASSTKVDKKV Rat IgG2c (Accession number AABR03049912) CH1,
SEQ ID NO: 16
ARTTAPSVYPLVPGCSGTSGSLVTLGCLVKGYFPEPVTVKWNSGALSSG
VHTFPAVLQSGLYTLSSSVTVPSSTWSSQTVTCSVAHPATKSNLIKRI Rat IgG1, IgG2a, IgG2b and IgG2c Hinge sequences are described in Table 1 and FIG. 1B.

Rat IgG1 CH2,
SEQ ID NO: 17
GSEVSSVFIFPPKPKDVLTITLTPKVTCVVVDISQDDPEVHFSWFVDDVE
VHTAQTRPPEEQFNSTFRSVSELPILHQDWLNGRTFRCKVTSAAFPSPIE
KTISKPE

Rat IgG2a CH2,
SEQ ID NO: 18
GSEVSSVFIFPPKTKDVLTITLTPKVTCVVVDISQNDPEVRFSWFIDDVE
VHTAQTHAPEKQSNSTLRSVSELPIVHRDWLNGKTFKCKVNSGAFPAPIE
KSISKPE

Rat IgG2b CH2,
SEQ ID NO: 19
VPELLGGPSVFIFPPKPKDILLISQNAKVTCVVVDVSEEEPDVQFSWFVN
NVEVHTAQTQPREEQYNSTFRVVSALPIQHQDWMSGKEFKCKVNNKALPS
PIEKTISKPK

Rat IgG2c CH2,
SEQ ID NO: 20
CDDNLGRPSVFIFPPKPKDILMITLTPKVTCVVVDVSEEEPDVQFSWFVD
NVRVFTAQTQPHEEQLNGTFRVVSTLHIQHQDWMSGKEFKCKVNNKDLPS
PIEKTISKPR

Rat IgG1, IgG2a, IgG2b and IgG2c CH3 sequences are described in table 1 (SEQ ID NOs 57-60).

Rat kappa (Accession number V01241) CL,
SEQ ID NO: 21
RADAAPTVSIFPPSTEQLATGGASVVCLMNNFYPRDISVKWKIDGTERR
DGVLDSVTDQDSKDSTYSMSSTLSLTKADYESHNLYTCEVVHKTSSSPV
VKSFNRNEC To introduce mutations in the CH3 regions of the antibody heavy chains, i.e. F405L, K409R, S370K, T370K, N411T or S411T, Quickchange site-directed mutagenesis kit (Stratagene, La Jolla, Calif.) was used according to the manufacturer's recommendations. Alternatively the constructs were fully synthesized or VH regions were cloned in a vector already containing the specific amino acid encoding substitutions.

Example 5: Antibody Production by Transient Expression in FreeStyle™ 293-F or Expi293F™ Cells Antibodies were produced, under serum-free conditions, by co-transfecting relevant heavy and light chain expression vectors in FreeStyle™ 293-F cells (LifeTechnologies), using 293Fectin™ (LifeTechnologies), according to the manufacturer's instructions. Alternatively, antibodies were produced, under serum-free conditions, by co-transfecting relevant heavy and light chain expression vectors in Expi293F™ cells (LifeTechnologies), using ExpiFectamine™ 293 (LifeTechnologies), according to the manufacturer's instructions.

Example 6: Purification of Antibodies

Antibodies were purified by protein A affinity chromatography. In short, culture supernatant was filtered over 0.2 µm dead-end filters, loaded on 5 mL MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH$_2$PO$_4$, 140 mM NaCl, pH 7.4 (B. Braun). Alternatively, subsequent to purification, the eluate was loaded on a HiPrep Desalting column and the antibody was exchanged into 12.6 mM NaH$_2$PO$_4$, 140 mM NaCl, pH 7.4 (B. Braun) buffer. After dialysis or exchange of buffer, samples were sterile filtered over 0.2 µm dead-end filters. Alternatively, antibodies were purified by protein G affinity chromatography.

Purity was determined by SDS-PAGE/CE-SDS and concentration was measured by absorbance at 280 nm. Batches of purified antibody were tested by high-performance size-exclusion chromatography (HP-SEC) for aggregates or degradation products. Purified antibodies were stored at 2-8° C.

Example 7: Dual-Binding ELISA to Determine Efficiency of Bispecific Antibodies Generation The presence of bispecific antibodies was tested by determination of bispecific antigen binding using a sandwich enzyme-linked immunosorbent assay (ELISA). ELISA plates (Greiner bio-one, Frickenhausen, Germany) were coated overnight with 2 µg/mL (100 µL/well) of recombinant extracellular domain of EGFR in PBS at 4° C. The plates were washed once with PBST. Dilution series of the antibody samples (0-1 µg/mL in 3-fold dilutions) in PBST/0.2% BSA (PBSTB) were transferred to the coated ELISA plates (100 µL/well) and incubated on a plate shaker (300 rpm) for 60 min at room temperature (RT). Samples were discarded and the plates were washed once with PBS/0.05% Tween 20 (PBST). Next, the plates were incubated on a plate shaker (300 rpm) with 2 µg/mL mouse anti-idiotypic monoclonal antibody 2F2 SAB1.1 (directed against 7D8; Genmab) in PBTB (100 µL/well) for 60 min. The plates were washed once with PBS/0.05% Tween 20 (PBST). Next, the plates were incubated on a plate shaker (300 rpm) with an HRP-conjugated goat anti-mouse IgG (15G; Jackson ImmunoResearch Laboratories, Westgrove, Pa., USA; 1:5.000) in PBSTB (100 µL/well) for 60 min at RT. The plates were washed once with PBS/0.05% Tween 20 (PBST). ABTS (50 mg/mL; Roche Diagnostics GmbH, Mannheim, Germany) was added (100 µL/well) and incubated protected from light for 30 min at RT. The reaction was stopped with 2% oxalic acid (100 µL/well; Riedel de Haen, Seelze, Germany). After 10 min at RT, absorbance at 405 nm was measured in an ELISA plate reader. Percentage (%) Bispecifics is defined as ((absorbance at 405 nm of the sample)-(absorbance at 405 nm of assay diluent only)/(absorbance at 405 nm of reference bsIgG1-7D8×2F8)-(absorbance at 405 nm of assay diluent only))×100.

Example 8: Hydrophobic Interaction Chromatography to Determine Efficiency of Bispecific Antibody Generation Hydrophobic interaction chromatography (HIC) can be used to separate both parental antibodies from the bispecific antibody product, based on the inherent hydrophobic properties of the different proteins. Here, High Pressure Liquid Chromatography (HPLC)-HIC was applied to quantify the efficiency of the cFAE reaction. For this, samples of the parental antibodies and the bispecific antibody product, generated by cFAE, were diluted twofold with HIC eluent A (15.4 mM K$_2$HPO$_4$, 9.6 mM KH$_2$PO$_4$, 1.5 M (NH$_4$)$_2$SO$_4$; pH 7.0) to a final concentration of 1 mg/mL for injection into the HPLC. The IgG molecules with different hydrophobic properties were separated by using a Butyl-NPR, 2.5 µm, 4.6×35 mm HIC-HPLC column (Tosoh Bioscience) with a flow rate of 1 mL/min. 50 µL was injected and elution was performed with a 12-min gradient of HIC eluent A to HIC eluent B (15.4 mM K$_2$HPO$_4$, 9.6 mM KH$_2$PO$_4$; pH 7.0) and detection occurred at 280 nm. Empower 3 software (Waters) was used to assign and integrate peak areas. Chromatograms of the parental antibodies were used as reference to identify their position in the end-product. The relative peak areas of the bispecific antibody and residual parental antibodies were used to calculate the efficiency of the cFAE reaction.

Example 9: Generation of Bispecific Chimeric Antibodies, Containing Mouse-Derived CH3 Domains that Include Matching Mutations F405L and K409R in Combination with Additional CH3 Mutations by Controlled Fab-Arm Exchange Bispecific antibodies were generated in vitro using the DuoBody® platform technology, i.e. controlled Fab-arm exchange (cFAE) or 2-MEA-induced Fab-arm exchange as described in WO 2011/131746; Labrijn et al., PNAS 2013, 110: 5145-50; Gramer et al., MAbs 2013, 5: 962-973 and Labrijn et al., Nat Biotechnol 2014, 9: 2450-63 (summarized in FIG. 1A). Mixtures of constructs were subjected to controlled Fab-arm exchange (cFAE): To generate bispecific antibodies, 100 µg of each parental antibody was mixed and incubated with 75 mM 2-mercaptoethylamine-HCl (2-MEA) in a total volume of 400 µL PBS (B. Braun, product #3623140) at 31° C. for 5 hours. The reduction reaction was stopped when the reducing agent 2-MEA was removed by using Amicon Ultra 0.5 ml centrifugal units (10 kD MWCO, Millipore, product # UFC501096) and washing 4× with 400 µl PBS by centrifuging 10 min at 13000×g. Samples were collected in a new tube by inverting the filter and centrifuging 2 min at 1000×g. Volumes were adjusted to 200 µL (when needed) with PBS. The absorbance of 280 nm (A280) of bispecific products was measured to determine the final concentration. Samples were stored at 2-8° C. until further analysis. Dual-binding ELISA (as described in Example 7) and HIC analysis (as described in Example 8) was performed to determine the amount of bispecific product.

FIG. 2 shows that introduction of the matching mutations F405L and K409R in the chimeric constructs containing mouse IgG1 and mouse IgG2a CH3 regions, i.e. hsIgG1-CH3 (mmG1) and hsIgG1-CH3 (mmG2a), had no effect, whereas their introduction in chimeric constructs containing the mouse IgG2b CH3 region, i.e. hsIgG1-CH3 (mmG2b) enabled cFAE. To find additional CH3 domain mutations for increasing the efficiency of heterodimerization of parental rodent homodimers into the bispecific product, the following constructs were generated:

TABLE 2

| Chimeric constructs containing mouse-derived CH3 domains | |
|---|---|
| hsIgG1-CH3(mmG1)-7D8-K409R | hsIgG1-CH3(mmG1)-2F8-F405L |
| hsIgG1-CH3(mmG1)-7D8-M368L-K409R | hsIgG1-CH3(mmG1)-2F8-M368L-F405L |
| hsIgG1-CH3(mmG1)-7D8-T370K-K409R | hsIgG1-CH3(mmG1)-2F8-T370K-F405L |
| hsIgG1-CH3(mmG1)-7D8-K409R-N411T | hsIgG1-CH3(mmG1)-2F8-F405L-N411T |
| hsIgG1-CH3(mmG1)-7D8-M368L-T370K- | hsIgG1-CH3(mmG1)-2F8-M368L-T370K- |

TABLE 2-continued

| Chimeric constructs containing mouse-derived CH3 domains | |
|---|---|
| K409R | F405L |
| hsIgG1-CH3(mmG1)-7D8-M368L-K409R-N411T | hsIgG1-CH3(mmG1)-2F8-M368L-F405L-N411T |
| hsIgG1-CH3(mmG1)-7D8-T370K-K409R-N411T | hsIgG1-CH3(mmG1)-2F8-T370K-F405L-N411T |
| hsIgG1-CH3(mmG2a)-7D8-K409R | hsIgG1-CH3(mmG2a)-2F8-F405L |
| hsIgG1-CH3(mmG2a)-7D8-M368L-K409R | hsIgG1-CH3(mmG2a)-2F8-M368L-F405L |
| hsIgG1-CH3(mmG2a)-7D8-T370K-K409R | hsIgG1-CH3(mmG2a)-2F8-T370K-F405L |
| hsIgG1-CH3(mmG2a)-7D8-K409R-R411T | hsIgG1-CH3(mmG2a)-2F8-F405L-R411T |
| hsIgG1-CH3(mmG2a)-7D8-M368L-T370K-K409R | hsIgG1-CH3(mmG2a)-2F8-M368L-T370K-F405L |
| hsIgG1-CH3(mmG2a)-7D8-M368L-K409R-R411T | hsIgG1-CH3(mmG2a)-2F8-M368L-F405L-R411T |
| hsIgG1-CH3(mmG2a)-7D8-T370K-K409R-R411T | hsIgG1-CH3(mmG2a)-2F8-T370K-F405L-R411T |
| hsIgG1-CH3(mmG2b)-7D8-K409R | hsIgG1-CH3(mmG2b)-2F8-F405L |
| hsIgG1-CH3(mmG2b)-7D8-V370K-K409R | hsIgG1-CH3(mmG2b)-2F8-V370K-F405L |
| hsIgG1-CH3(mmG2b)-7D8-K409R-N411T | hsIgG1-CH3(mmG2b)-2F8-F405L-N411T |
| hsIgG1-CH3(mmG2b)-7D8-V370K-K409R-N411T | hsIgG1-CH3(mmG2b)-2F8-V370K-F405L-N411T |

Mixtures of constructs were subjected to cFAE (as described above) and dual-binding ELISA (as described in Example 7) and HIC analysis (as described in Example 8) was performed to determine the amount of bispecific product.

Figure 2B:
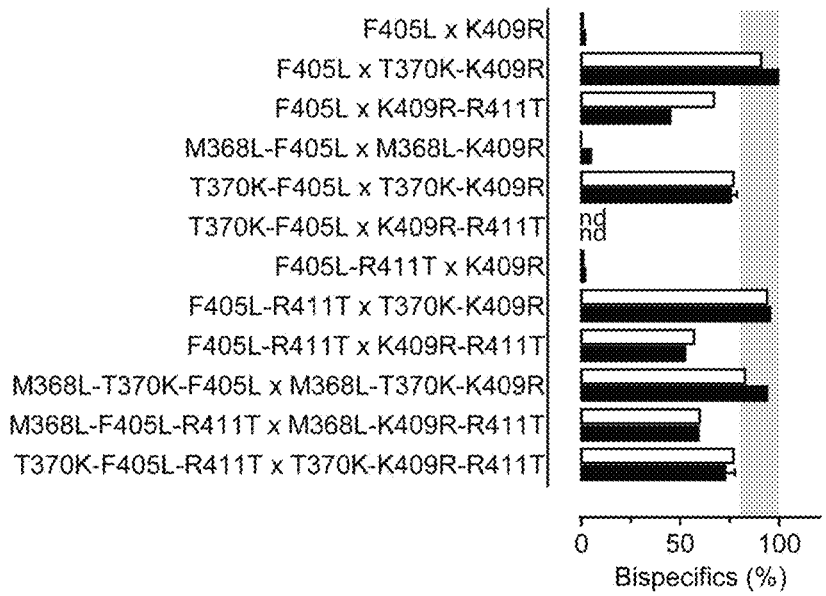
Figure 3A:
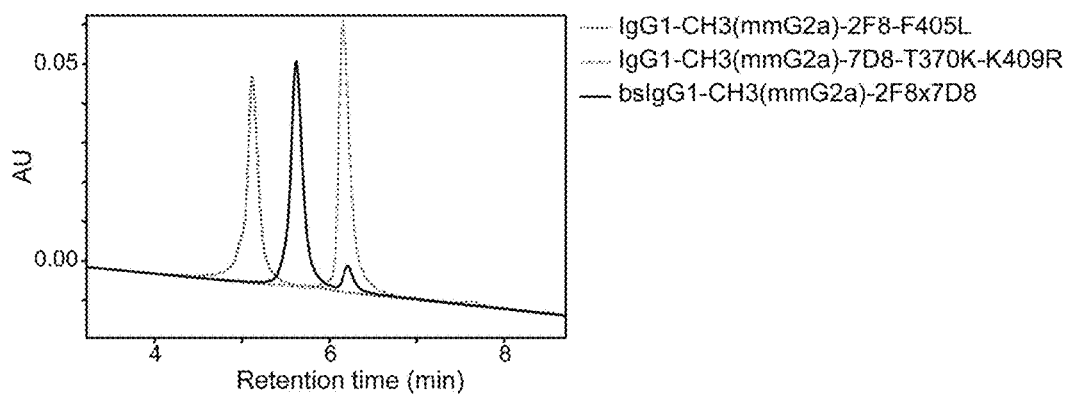
FIGS. 3A and 3B: Exemplary Hydrophobic Interaction Chromatography (HIC) characterization of bispecific antibodies (containing mouse-derived CH3 domains).

FIGS. 2A and 2B show that, whereas introduction of the M368L mutation alone had no significant effect, introducing mutations T370K and N/R411T, either alone or together, in both parental antibodies, increased the cFAE efficiency in IgG1-CH3 (mmG1) (A) and IgG1-CH3 (mmG2a) (B) backbones as measured by Dual-binding ELISA and HIC. Introducing M368L together with T370K or N/R411T had no additional effect compared to the introduction of T370K or N/R411T alone. The T370K-F405L×T370K-K409R, T370K-F405L-N/R411T×T370K-K409R-N/R411T, M368L-T370K-F405L×M368L-T370K-K409R and M368L-F405L-N/R411T×M368L-K409R-N/R411 mixtures in the IgG1-CH3 (mmG1) (A) and IgG1-CH3 (mmG2a) (B) backbones reached higher cFAE efficiencies. Surprisingly, the highest cFAE efficiencies in IgG1-CH3 (mmG1) and IgG1-CH3 (mmG2a) backbones, as measured by both dual-binding ELISA and HIC (see also FIG. 3 for exemplary chromatograms), were obtained when the T370K mutation alone was introduced in the K409R parental antibody only, and mixed with parental antibodies containing the F405L mutation only or the combination of F405L with the N/R411T mutation, i.e. F405L×T370K-K409R or F405L-N/R411T×T370K-K409R.

Figure 2C:
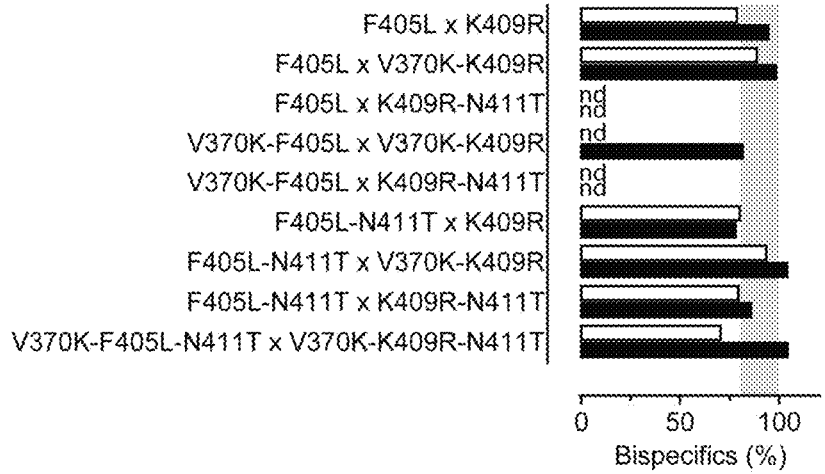
Figure 3B:
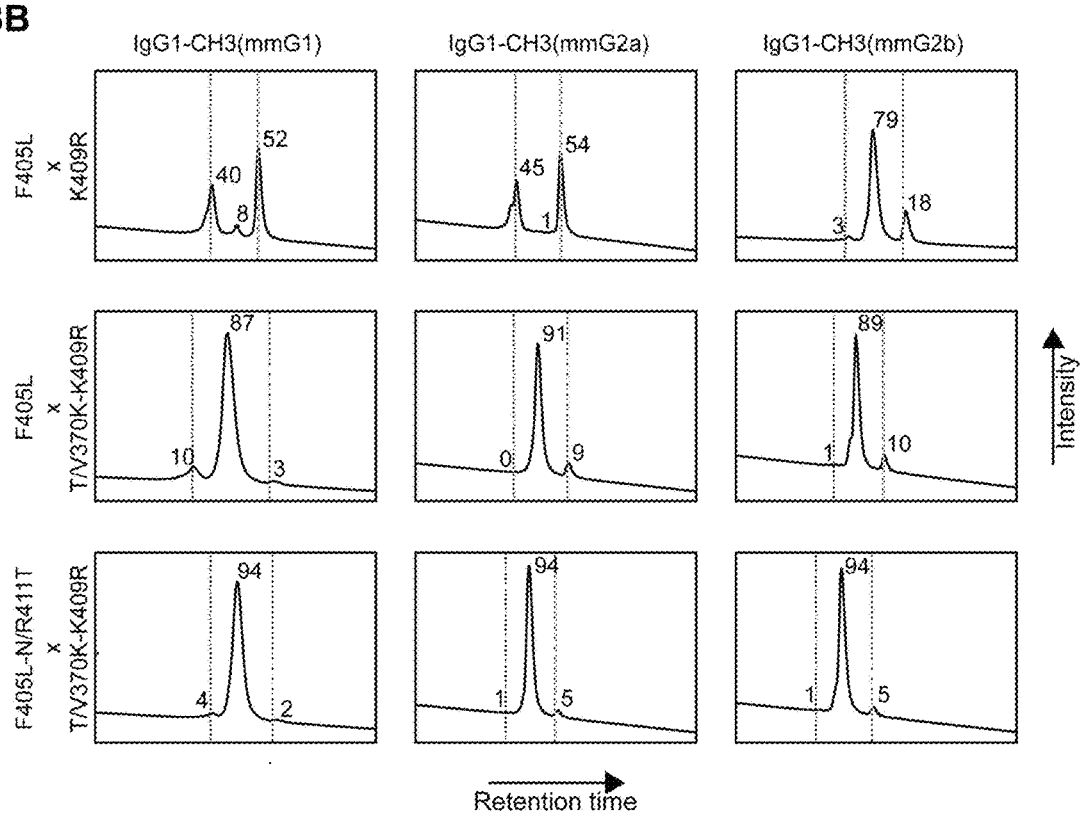

FIG. 2C and FIG. 3B show that although the combination of F405L×K409R in a IgG1-CH3 (mmG2b) backbone was already able to undergo cFAE, the introduction of mutations in the equivalent positions could still increase the cFAE efficiency. F405L×V370K-K409R or F405L-N411T×T370K-K409R were the most efficient combinations.

Figure 4A:
FIGS. 4A-4C.

Example 10: Generation of Bispecific Mouse Antibodies, Containing Mouse-Derived Constant Regions that Include Matching Mutations F405L and K409R Alone or in Combination with Additional CH3 Mutations, N/R411T and T/V370K, Respectively, by Controlled Fab-Arm Exchange To verify that the identified combinations also supported efficient cFAE in the context of an entire mouse constant domain, they were introduced in chimeric constructs containing mouse-derived constant regions (FIG. 4A). This resulted in the following constructs:

TABLE 3

| Chimeric constructs containing mouse-derived constant regions | |
|---|---|
| mmIgG1-7D8 | mmIgG1-2F8 |
| mmIgG1-7D8-K409R | mmIgG1-2F8-F405L |
| mmIgG1-7D8-T370K-K409R | mmIgG1-2F8-F405L-N411T |
| mmIgG2a-7D8 | mmIgG2a-2F8 |
| mmIgG2a-7D8-K409R | mmIgG2a-2F8-F405L |
| mmIgG2a-7D8-T370K-K409R | mmIgG2a-2F8-F405L-R411T |
| mmIgG2b-7D8 | mmIgG2b-2F8 |
| mmIgG2b-7D8-K409R | mmIgG2b-2F8-F405L |
| mmIgG2b-7D8-T370K-K409R | mmIgG2b-2F8-F405L-N411T |
| mmIgG3-7D8 | mmIgG3-2F8 |
| mmIgG3-7D8-K409R | |

Mixtures of constructs were subjected to cFAE (as described in Example 9) and dual-binding ELISA (as described in Example 7) and HIC analysis (as described in Example 8) was performed to determine the amount of bispecific product.

Figure 4B:
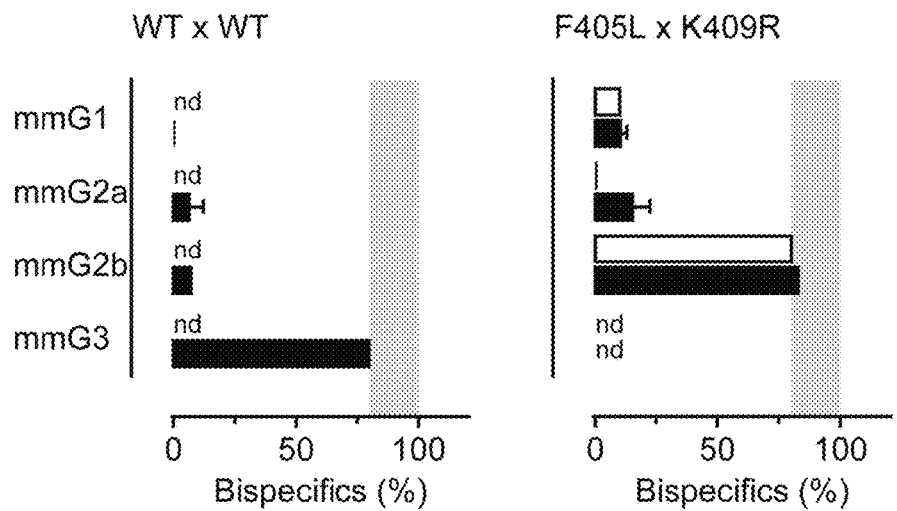

FIG. 4 shows that, like for the chimeric constructs containing mouse CH3 domains, introduction of the matching mutations F405L and K409R in the chimeric constructs containing the entire mouse constant regions, only resulted in sub-efficient cFAE (approx. 80%) in a mmIgG2b backbone (FIG. 4B) and almost no cFAE in mmIgG1 and mmIgG2a backbones. Surprisingly, the constructs containing the entire constant region of mmIgG3 enabled sub-efficient cFAE (approx. 80%) (FIG. 4A).

Figure 4C:
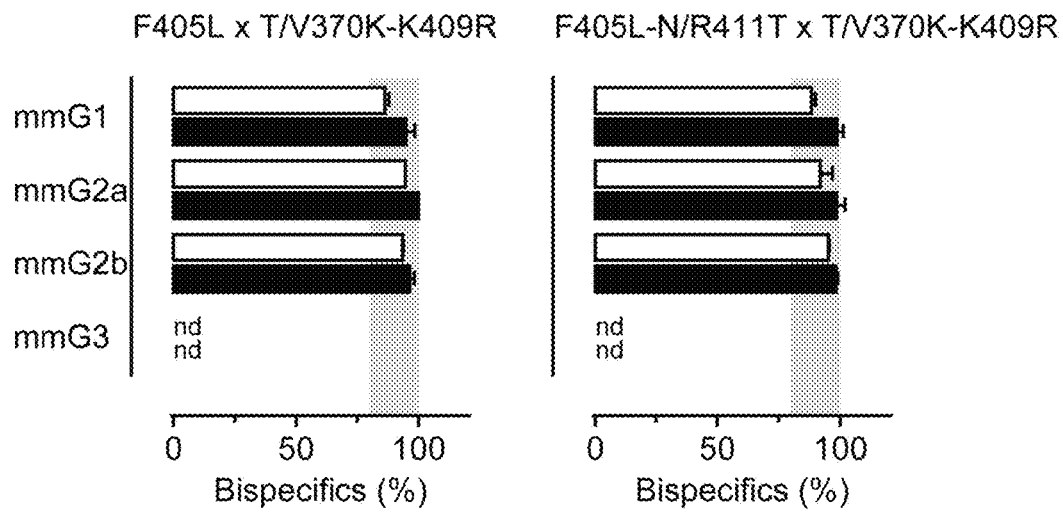
Figure 5:
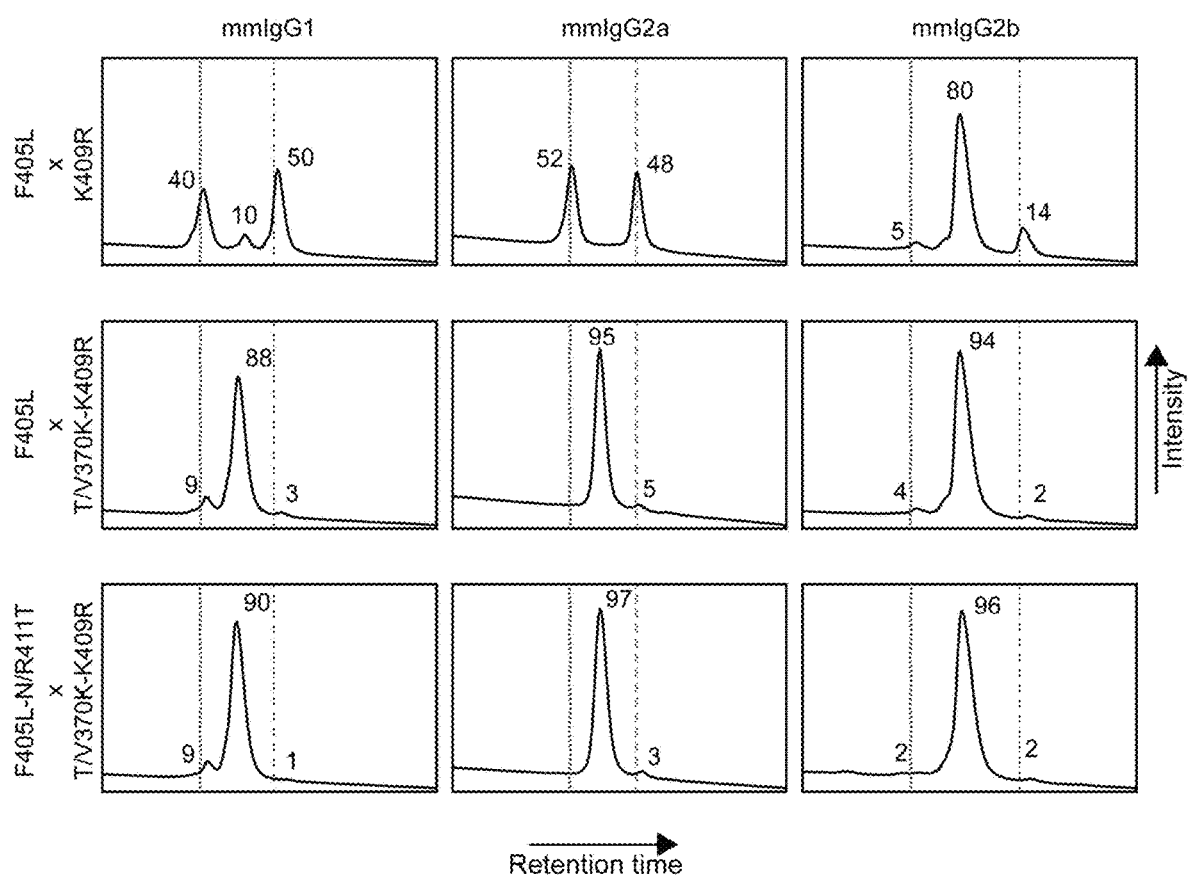
FIG. 5: Exemplary Hydrophobic Interaction Chromatography (HIC) characterization of bispecific antibodies (containing mouse-derived constant regions) generated by controlled Fab-arm exchange using the indicated (above and left of panels) combination of parental antibodies. Numbers indicate percentages of bispecific antibody product (middle peaks) and residual 2F8 and 7D8-derived parental antibodies (left and right peaks, respectively). Vertical lines correspond with the retention times of the HIC analyses of the individual parental antibodies.

High cFAE efficiencies such as 95-100% and 86-95%, as measured by both dual-binding ELISA and HIC, respectively, were observed in the chimeric constructs containing the entire mouse constant regions when the T/V370K mutation was introduced in the K409R parental antibody (mmIgG1-T370K-K409R, mmIgG2a-T370K-K409R and mmIgG2b-V370K-K409R), and mixed with parental antibodies containing the F405L mutation only (mmIgG1-F405L, mmIgG2a-F405L and mmIgG2b-F405L) or the combination of F405L with the N/R411T mutation (mmIgG1-F405L-N411T, mmIgG2a-F405L-R411T and mmIgG2b-F405L-N411T) (FIG. 4C). FIG. 5 shows exemplary HIC chromatograms.

Figure 6A:
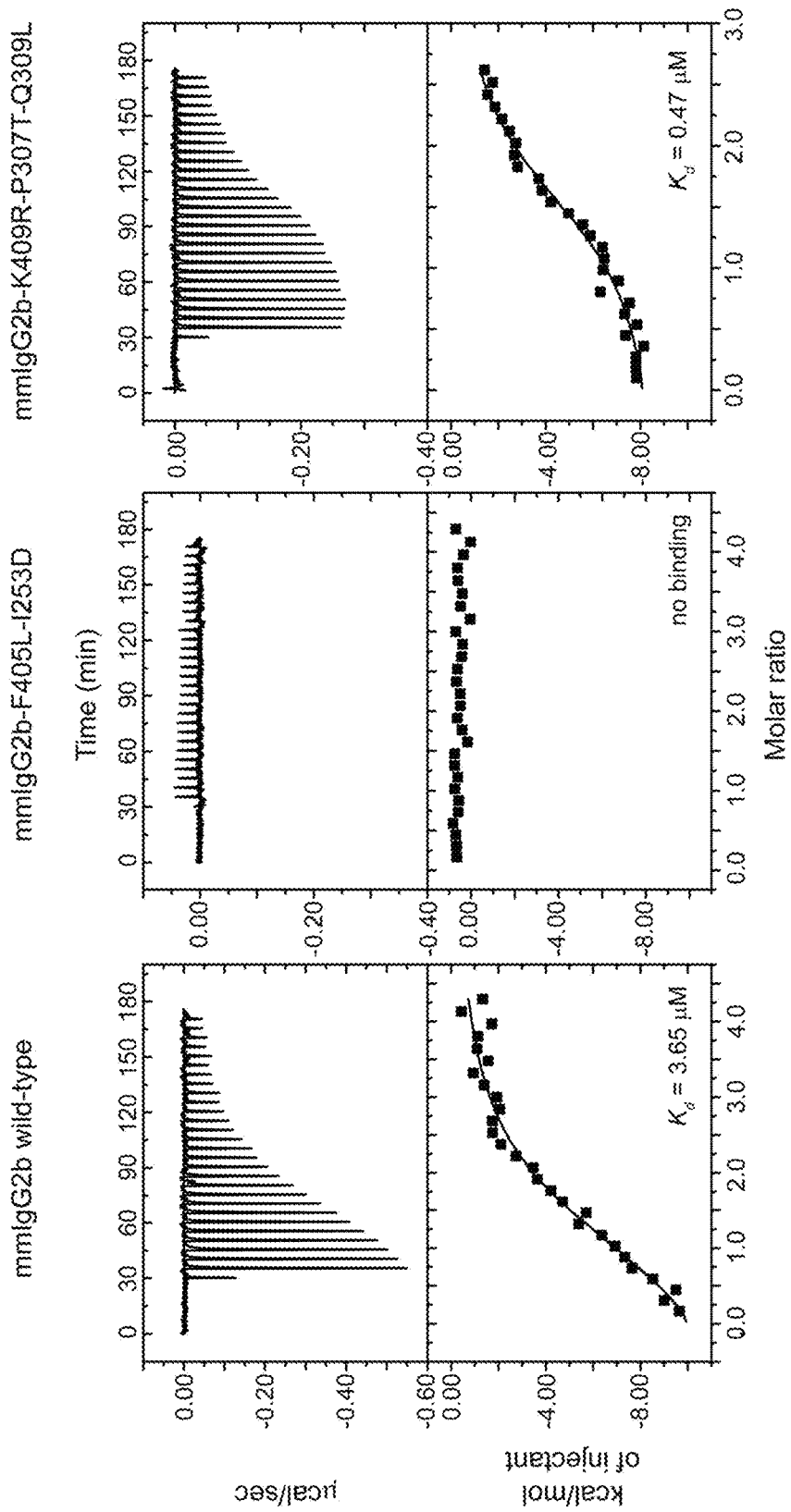
FIGS. 6A-6C.

Example 11: Differential Protein a Purification to Polish Bispecific Mouse Antibodies In order to facilitate differential protein A purification for cases were the presence of residual parental antibodies are undesired, a set of mutations in the CH2 domain were designed that disrupt (I253D) or enhance (P307T, Q309L) binding of mmIgG2b to protein A. These mutations were introduced into a set of parental mmIgG2b antibodies to yield mmIgG2b-I253D-F405L and mmIgG2b-P307T-Q309L-K409R and purified proteins were assessed for their ability to bind the Z-domain (an engineered analogue if the IgG-binding domain of protein A) by isothermal titration calorimetry. FIG. 6A shows that compared to mmIgG2b-F405L, the mmIgG2b-I253D-F405L construct does not bind the Z-domain and mmIgG2b-P307T-Q309L-K409R binds the Z-domain 5-fold tighter.

Figure 6B:
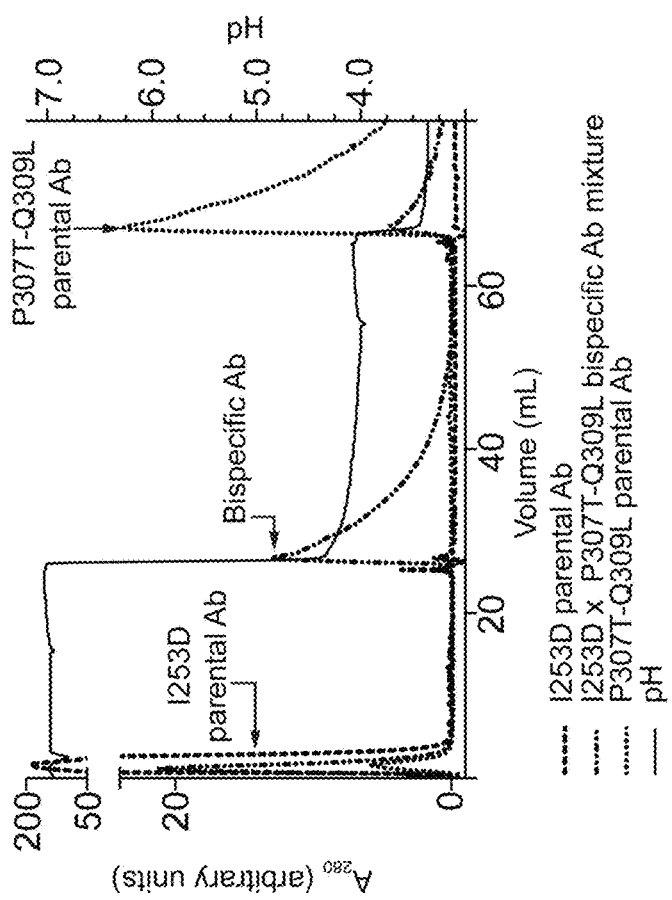
Figure 6C:
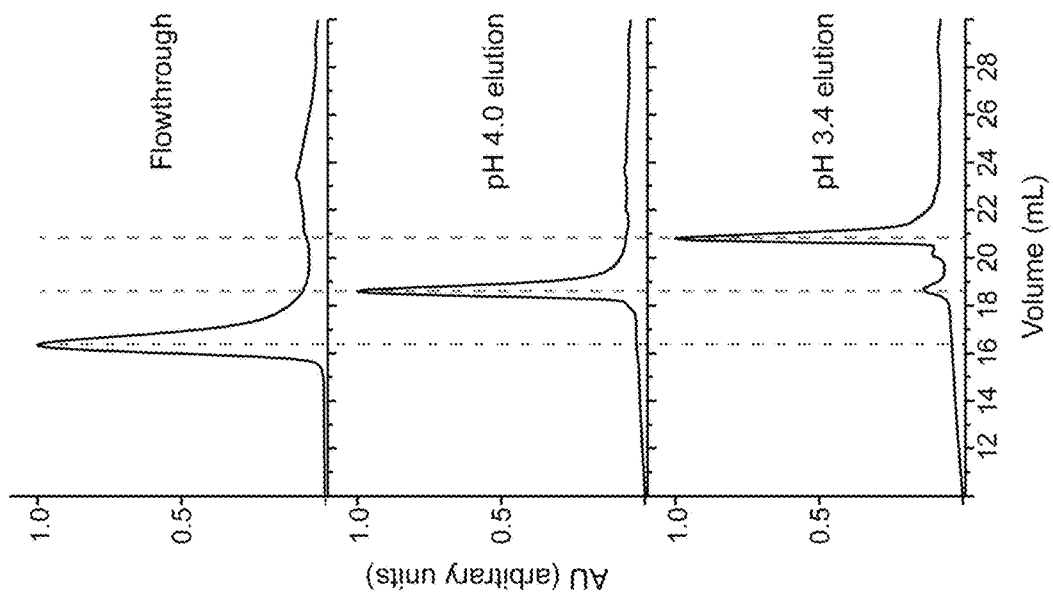

Mixtures of constructs were subjected to cFAE (as described in Example 9) and purified by protein A affinity chromatography, basically as described in Example 6, with the exception that a 3-step pH gradient was used for elution (pH 7.2, pH 4.0, pH 3.4). The flow-through and elution fractions were subsequently analyzed by HIC. FIG. 6B shows that the mmIgG2b-I253D-F405L parental antibody does not bind to protein A and can only be detected in the flow through. In contrast, mmIgG2b-P307T-Q309L-K409R parental antibody binds tightly to protein A and is mainly detected after the pH 3.4 elution. The bispecific mouse antibody mixture was resolved into three fractions (flowthrough, pH elution 4.0 and pH elution 3.4) which contained, respectively, the residual mmIgG2b-I253D-F405L parental antibody, the bs-mmIgG2b-I253D-F405L×P307T-Q309L-K409R and the residual mmIgG2b-P307T-Q309L-K409R parental antibody (with a trace of bispecific mouse antibody)(FIGS. 6B and C). Thus highly pure bispecific molecules could be obtained using differential protein A purification from a mixture of parental and bispecific mmIgG2b antibodies. Similar results are expected for mmIgG2a antibodies with corresponding mutations.

Figure 7A:
FIGS. 7A-7C.

Example 12: Generation of Bispecific Rat Antibodies, Containing Rat-Derived Constant Regions that Include Mutations F405L and K409R Alone or in Combination with Additional CH3 Mutations, N/S411T and 5/T370K, Respectively, by Controlled Fab-Arm Exchange To assess whether these identified combinations of mutations were also relevant for other rodent species, like rats (*Rattus norvegicus*), they were introduced in chimeric constructs containing rat-derived constant regions (FIG. 7A). This resulted in the following constructs:

TABLE 4

Chimeric constructs containing rat-derived constant regions

| | |
|---|---|
| rnIgG1-7D8 | rnIgG1-2F8 |
| rnIgG1-7D8-K409R | rnIgG1-2F8-F405L |
| rnIgG2a-7D8 | rnIgG1-2F8-F405L-N411T |
| rnIgG2a-7D8-K409R | rnIgG2a-2F8 |
| rnIgG2b-7D8 | rnIgG2a-2F8-F405L |
| rnIgG2b-7D8-K409R | rnIgG2a-2F8-F405L-N411T |
| rnIgG2b-7D8-S370K-K409R | rnIgG2b-2F8 |
| rnIgG2c-7D8 | rnIgG2b-2F8-F405L |
| rnIgG2c-7D8-K409R | rnIgG2b-2F8-F405L-N411T |
| rnIgG2c-7D8-T370K-K409R | rnIgG2c-2F8 |
| | rnIgG2c-2F8-F405L |
| | rnIgG2c-2F8-F405L-S411T |

Mixtures of constructs were subjected to cFAE (as described in Example 9) and dual-binding ELISA (as described in Example 7) and HIC analysis (as described in Example 8) was performed to determine the amount of bispecific product.

Figure 7B:
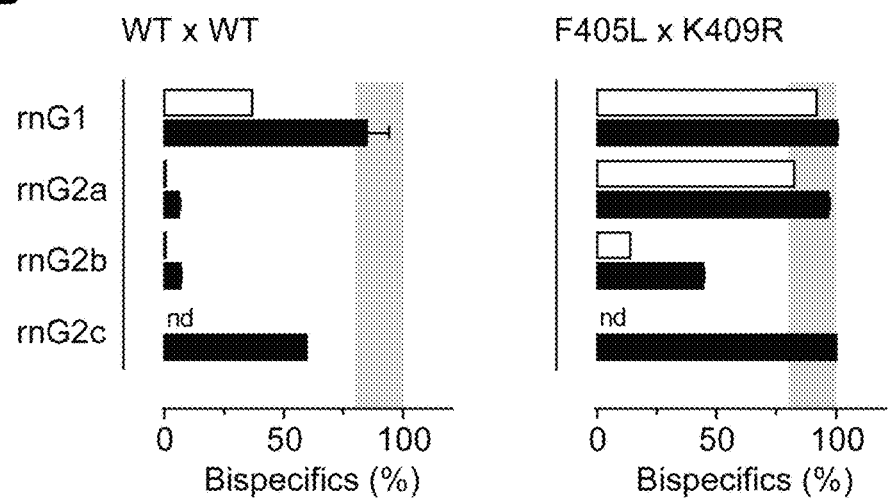
Figure 7C:
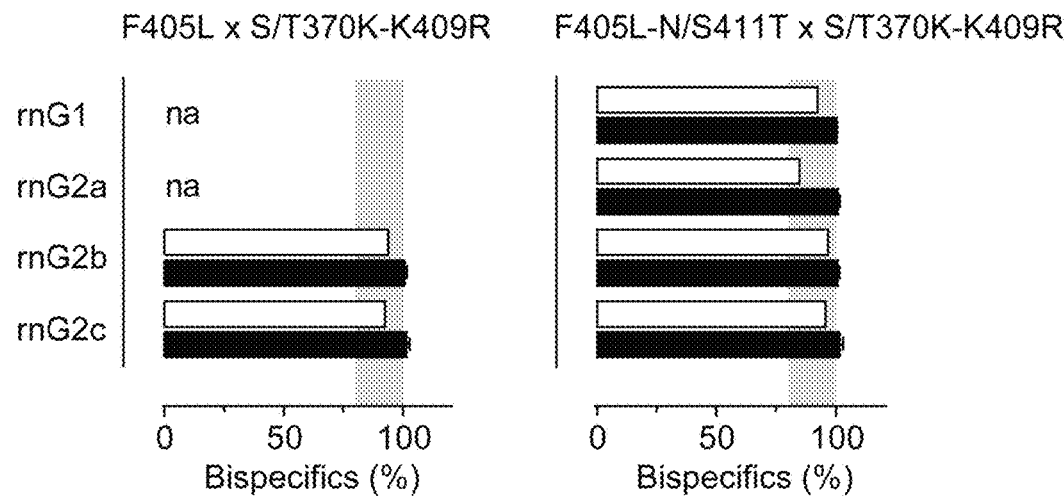

FIG. 7 shows that, introduction of the matching mutations F405L and K409R in the chimeric constructs containing the entire rat constant regions, resulted in highly efficient cFAE (such as 95-100% and 86-95%, as measured by both dual-binding ELISA and HIC, respectively) in the rnIgG1, rnIgG2a and rnIgG2c backbones (FIG. 7B) and almost no cFAE in rnIgG2b backbones. High cFAE efficiencies were observed in the chimeric constructs containing the entire rat constant regions when the K409R parental antibody naturally contained the K370 (rnIgG1-K409R and rnIgG2a-K409R) or when the S/T370K mutation was introduced in the K409R parental antibody (rnIgG2b-5370K-K409R and mmIgG2c-T370K-K409R), and mixed with parental antibodies containing the F405L mutation only (rnIgG1-F405L, rnIgG2a-F405L, rnIgG2b-F405L and rnIgG2c-F405L) or the combination of F405L with the N/R411T mutation (rnIgG1-F405L-N411T, rnIgG2a-F405L-N411T, rnIgG2b-F405L-N411T and rnIgG2c-F405L-5411T) (FIG. 7C).

Example 13: Culturing Bone Marrow-Derived Macrophages

Bone marrow was isolated from the hind legs of BALB/c mice (Charles Rivers Laboratories) by flushing the femoral and tibial bones using an insulin syringe filled with bone marrow medium (DMEM (Cambrex, product # BE12-709F) supplemented with 50 IU/mL penicillin, 50 µg/mL streptomycin (Cambrex, product # DE17-603E), 10% (v/v) heat-inactivated donor bovine serum (Gibco, product #10371-029) and 2 mM L-glutamine (Cambrex, product # US17-905C)) until the bones turned white. The cells were collected in a 50 ml tube and the volume was adjusted to 30 ml with bone marrow medium. After passing through a cell strainer, the cells were seeded in petri dishes at a cell concentration of $1.25 \times 10^5$ cells/mL in 10 mL. Cells were cultured for 7-8 days at 37° C./5% $CO_2$ in the presence of 50 U/mL M-CSF (PeproTech Inc., product #315-02). After 3-4 days of incubation, 5 ml/dish fresh bone marrow medium with M-CSF was added.

Example 14: Antibody-Dependent Cellular Phagocytosis (ADCP)

On day 7-8, bone-marrow derived macrophages were washed with PBS and harvested by incubating the cells for 10 min at 37° C. with 2 mL Versene (Gibco, product #15040-033). Detached cells were collected in a 50 ml tube and Versene was inactivated by adding bone marrow medium. Cells were washed twice and resuspended in 5 mL ADCP working medium (DMEM (Cambrex, product # BE12-917F) supplemented with 50 IU/mL penicillin, 50 µg/mL streptomycin, 10% (v/v) donor bovine serum, 2 mM L-glutamin) and 2.5% HEPES (Sigma Aldrich, product # H0887)). Cells were counted and the concentration was adjusted to $0.5 \times 10^6$ cells/mL with ADCP working medium. The bone-marrow derived macrophages were seeded into 96-well culture plates (200 µL/well) and allowed to adhere overnight at 37° C., 5% $CO_2$.

The following day, Daudi cells (ATCC; CCL-213) (cultured in RPMI 1640 (Lonza) supplemented with 10% (v/v) heat-inactivated donor bovine serum, 2 mM L-glutamine (Lonza), 1 mM sodium pyruvate (Lonza), 50 IU/mL penicillin, and 50 µg/mL streptomycin) were harvested and labeled for 25 min at 37° C. with 0.01 nM Calcein-AM (Molecular probes, product # C-3100), according to the manufacturer's instructions. Labeled Daudi cells were washed twice with ADCP working medium, counted and the concentration was adjusted to 1×10⁶ cells/mL. Supernatant from the bone-marrow derived macrophages culture plates was removed and Daudi target cells (T) were added to the macrophage effector cells (E) at an E:T ratio of 1:1 in the presence of a fixed antibody concentration of 1 µg/mL. After a 4 h incubation at 37° C./5% $CO_2$, target cells were washed away with PBS and macrophages were detached with Trypsin-EDTA (Gibco, product #15400-054) and stained with F4/80-PE (AbD Serotec) and CD19-APC (DAKO, Glostrup, Denmark). ADCP was evaluated on a FACSCanto II flow cytometer (BD Biosciences) and defined as percentage of macrophages that had phagocytized. Percentage of phagocytosis was calculated using the following gate settings: the percentage of calcein-AM-positive and CD19-negative cells within the F4/80-positive cells.

Figure 8A:
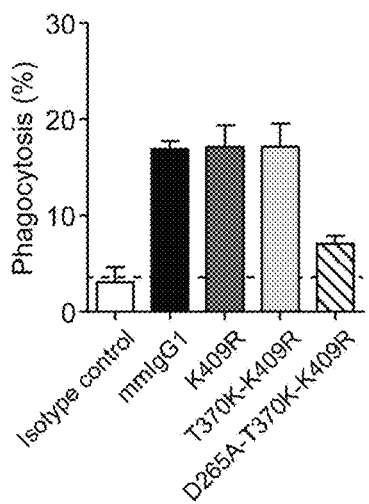
FIGS. 8A-8C: Antibody-Dependent Cellular Phagocytosis (ADCP) of Daudi cells (target cell; T) by bone marrow-derived mouse macrophages (effector cell; E) incubated with a fixed 1 μg/mL concentration of the indicated (FIG. 8A) mmIgG1-7D8, (FIG. 8B) mmIgG2a-7D8 and (FIG. 8C) mmIgG2b-7D8 variant, with an E:T ratio of 1:1. Data represent mean±SD of triple measurements of a representative experiment.
Figure 8B:
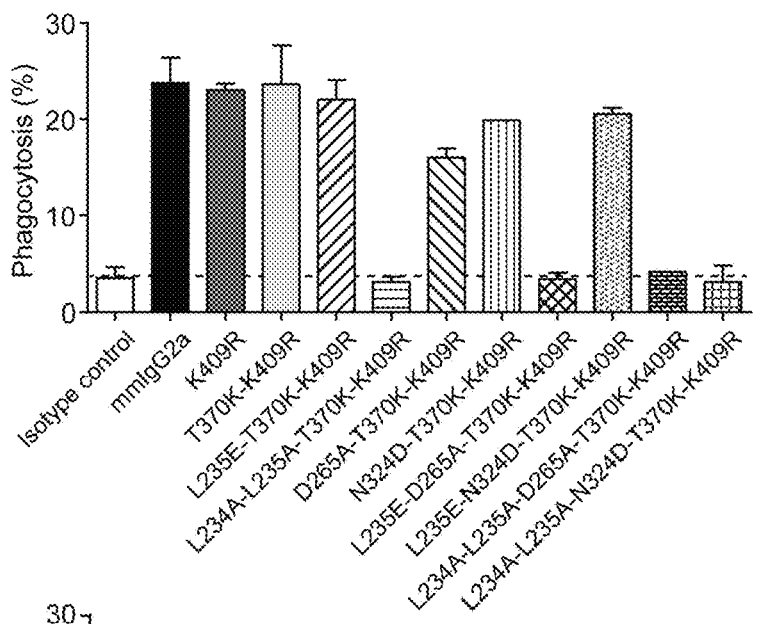
Figure 8C:
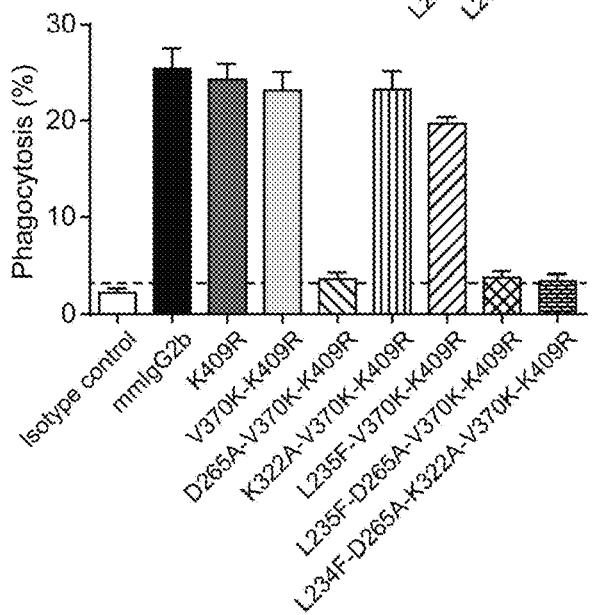

FIG. 8 shows that the K409R mutation alone or in combination with T370K (in mmIgG1 and mmIgG2a) or V370K (in mmIgG2b) had no effect on the phagocytic activity of the mouse antibody backbones. Introduction of point-mutation described in literature to affect effector functions did, in some cases, influence the phagocytic activity. For example, introducing D265A diminished the phagocytic activity in both mmIgG1-T370K-K409R and mmIgG2a-T370K-K409R backbones, and completely inactivated the phagocytic activity in a mmIgG2b-V370K-K409R backbone. Introduction of the L235E and N324D point-mutations, either alone or combined, had no effect on the phagocytic activity in mmIgG2a-T370K-K409R, whereas introducing L235E in combination with D265A completely inactivated the phagocytic activity. The mutation-combinations L234A-L235A, L234A-L235A-D265A or L234A-L235A-N324D also completely inactivated the phagocytic activity in mmIgG2a-T370K-K409R. Introduction of the L234F and K322A point-mutations alone had no effect on the phagocytic activity in mmIgG2b-V370K-K409R. The mutation-combinations L234F-D265A or L234F-D265A-K322A also completely inactivated the phagocytic activity in mmIgG2b-V370K-K409R.

Example 15: Isolation of Mouse Splenocytes

Splenocytes were extracted from freshly removed spleens of untreated BALB/cJ mice (Charles River Laboratories) by using the mouse spleen dissociation kit (Miltenyi Biotec, product #130-095-926) and the GentleMACS dissociator (Miltenyi Biotec, product #130-093-235) as per the manufacturer's instructions. In short, spleens were added to GentleMACS C tubes (Miltenyi Biotec, product #130-093-237) each containing 2.4 mL 1× Buffer S, 50 µL Enzyme D and 15 µL Enzyme A and placed on the GentleMACS dissociator. GentleMACS programs m_spleen_02 was run, followed by incubation for 15 minutes at 37° C. in a water bath. Subsequently GentleMACS programs m_spleen_03 was run, cells were collected and a single cell suspension was made by passing the cells through a cellstrainer. The cell strainer was washed with 2.5 ml 1× buffer S and cells were pelleted at 300 g for 10 min and resuspend in 10 ml PEB buffer (PBS, pH 7.2, 0.5% bovine serum albumin (BSA) and 2 mM EDTA). Splenocytes were counted using Burker turk solution and counting chamber.

Example 16 In Vitro Cytotoxicity Induced by HER2×mmCD3 Bispecific Mouse Antibodies Using Mouse Splenocytes as Effector Cells CD3 is a protein complex that is associated with the T cell receptor α and β chain expressed on mature T cells. Combination of a CD3 specific antibody Fab-arm with a tumor antigen specific antibody Fab-arm in a bispecific antibody would result in the specific retargeting of T cells to tumor cells, leading to T cell mediated tumor cell lysis. Likewise, CD3 positive T cells could be targeted to other derailed cells in the body, to infected cells or directly to pathogens. To assess whether mouse T-cells could be retargeted to tumor cell lines in vitro, various bispecific antibodies were generated using anti-human HER2 (HER2-169) and anti-mouse CD3E (145-2C11) antibody heavy and light chain variable region sequences.

HER2-169 (Labrijn et al. 2013. Proc Natl Acad Sci USA 110(13):5145-50, WO2012143524 (Genmab)) hereby incorporated by reference in its entirety, including sequence disclosures.

VH HER2-169, SEQ ID NO: 62:
QVQLVQSGAEVKKPGASVKVSCKASGYTFTNYGISWVRQAPGQGLEWMGW
LSAYSGNTIYAQKLOGRVTMTTDTSTTTAYMELRSLRSDDTAVYYCARDR
IVVRPDYFDYWGQGTLVTVSS

VL HER2-169, SEQ ID NO: 63:
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPRTFGQ
GTKVEIK 145-2C11 (Alegre et al. 1995. J Immunol. 155(3):
1544-55) hereby incorporated by reference in its
entirety, including sequence disclosures.

VH 145-2C11, SEQ ID NO: 64:
EVQLVESGGGLVQPGKSLKLSCEASGFTFSGYGMHWVRQAPGRGLESVAY
ITSSSINIKYADAVKGRFTVSRDNAKNLLFLQMNILKSEDTAMYYCARFD
WDKNYWGQGTMVTVSS

VL 145-2C11, SEQ ID NO: 65:
DIQMTQSPSSLPASLGDRVTINCQASQDISNYLNWYQQKPGKAPKLLIYY
TNKLADGVPSRFSGSGSGRDSSFTISSLESEDIGSYYCQQYYNYPWTFGP
GTKLEIK

The VH and VL sequences were introduced into chimeric constructs containing mouse-derived constant regions that contained F405L, T370K-K409R, D265A-F405L-N411T, or D265A-T370K-K409R mutations. This resulted in the following constructs:

TABLE 5

HER2 and mmCD3 chimeric constructs

| | |
|---|---|
| mmIgG1-HER2-169-T370K-K409R | mmIgG1-145-2C11-F405L |
| mmIgG1-HER2-169-D265A-T370K-K409R | mmIgG1-145-2C11-D265A-F405L-N411T |
| mmIgG2a-HER2-169-T370K-K409R | mmIgG2a-145-2C11-F405L |

Bispecific antibodies using these constructs (Table 5) and mmIgG1-7D8-T370K-K409R (Table 3) were generated (as described in Example 9) and HIC analysis (as described in Example 8) was performed to determine the amount of bispecific product.

The HER2×mmCD3 bispecific antibodies (and CD20× mmCD3 included as control) were then tested in an in vitro cytotoxicity assay using AU565 cells as target cells (T) and mouse splenocytes as effector cells (E). For this, AU565 cells (ATCC; CRL-2351) were cultured to near confluency. Cells were washed twice with PBS, and trypsinized for 5 minutes at 37° C. 12 mL culture medium was added to inactivate trypsin. After being collected and washed, the cells were resuspended in 10 mL culture medium and a single cell suspension was made by passing the cells through a cellstrainer. 100 µL of a 4×10⁵ cells/mL suspension was added to each well of a 96-well culture plate, and cells were incubated at least 3 hrs at 37° C., 5% CO₂ to allow adherence to the plate. Mouse splenocytes were isolated as described in Example 15. Isolated splenocytes were resuspended in culture medium to a final concentration of 8×10⁶ cells/mL. Culture medium was removed from the adhered AU565 cells, and replaced with 50 µL/well 2× concentrated antibody-dilution and 50 µL/well splenocyte suspension (final ratio E:T=10:1). Plates were incubated for 3 days at 37° C., 5% CO₂. Supernatants were removed and plates were washed twice with PBS. To each well 150 µL culture medium and 15 µL Alamar blue was added. Plates were incubate for 4 hours at 37° C., 5% CO₂, and absorbance (OD 590 nm) was measured (Envision, Perkin Elmer).

FIGS. 9A and B show that all bispecific HER2×mmCD3 antibodies induced dose-dependent T-cell mediated killing of AU565 cells in an in vitro cytoxicity assay with splenocytes. Killing was critically dependent on the presence of a tumor-targeting Fab-arm (bs-mmIgG1-145-2C11-F405L× HER2-169-T370K-K409R, bs-mmIgG1-145-2C11-D265A-F405L-N411T×HER2-169-D265A-T370K-K409R, bs-mmIgG2a-145-2C11-F405L×HER2-169-T370K-K409R), whereas control antibodies (CD3 monospecific (mmIgG1-145-2C11-F405L, mmIgG1-145-2C11-D265A-F405L-N411T, mmIgG2a-145-2C11-F4050, HER2 monospecific (mmIgG1-HER2-169-T370K-K409R, mmIgG1-HER2-169-D265A-T370K-K409R, mmIgG2a-HER2-169-T370K-K409R), irrelevant monospecific (mmIgG1-7D8-T370K-K409R) and irrelevant bispecific (bs-mmIgG1-145-2C11-F405L×7D8-T370K-K409R)) did not induce T cell cytotoxicity. As shown in FIG. 9A, the presence of the D265A mutation in the mmIgG1 backbone, and thus the inability to interact with Fc-receptors, did not impact the potential to induce dose-dependent cytotoxicity of AU565 cells using splenocytes.

Example 17: Pharmacokinetic (PK) Analysis of Bispecific Mouse Antibody Variants

The mice in this study were housed in a barrier unit of the Central Laboratory Animal Facility (Utrecht, The Netherlands) and kept in filter-top cages with water and food provided ad libitum. All experiments were approved by the Utrecht University animal ethics committee. 8-11 weeks old, female C57131/6J mice (Charles River Laboratories) were injected intravenously with 100 µg wild type antibody (mmIgG1-2F8 or mmIgG2a-b12), mmIgG1-based bispecific antibody (F405L-N411T×T370K-K409R), mmIgG2a-based bispecific antibody (F405L-R411T×T370K-K409R), mmIgG1-based bispecific antibody with additional D265A mutations or mmIgG2a-based bispecific antibody with additional L234A-L235A mutations, using 3 mice per group. 50 µL blood samples were collected from the saphenous vein at 10 minutes, 4 hours, 1 day, 2 days, 7 days, 14 days and 21 days after antibody administration. Blood was collected into heparin containing vials and centrifuged for 5 minutes at 10,000×g. Plasma was stored at −20° C. until determination of antibody concentrations.

Antibody concentrations were determined using an EGFR ELISA. For this assay, EGFR-ECDHis (Genmab), coated to 96-well Microlon ELISA plates (Greiner, Germany) at a concentration of 2 µg/mL was used as capturing antigen. Alternatively, antibody concentrations were determined using a gp120 ELISA, for which, gp120-JRFL (Progenics), coated to 96-well Microlon ELISA plates at a concentration of 0.5 µg/mL was used as capturing antigen. After blocking plates with PBS supplemented with 0.2% bovine serum albumin, the plates were washed and samples were added, serially diluted with ELISA buffer (PBS supplemented with 0.05% Tween 20 and 0.2% bovine serum albumin), and incubated on a plate shaker for 1 h at room temperature (RT). Plates were subsequently washed and incubated with HRP-labeled goat anti-mouse IgG immunoglobulin (#115-036-072, Jackson, West Grace, Pa.) and developed with 2,2'-azino-bis (3-ethylbenzthiazoline-6-sulfonic acid) (ABTS; Roche, Mannheim, Germany). The reaction was stopped after 30 min by adding 2% oxalic acid to the wells. Absorbance was measured in a microplate reader (Biotek, Winooski, Vt.) at 405 nm.

Plasma clearance rates (mL/day/kg) were calculated based on the area under the curve (AUC), according to the following equation:

Plasma clearance=Dose(µg/kg)/AUC(µg/mL/day)

Data analysis was performed using Graphpad prism software.

Figure 10A:
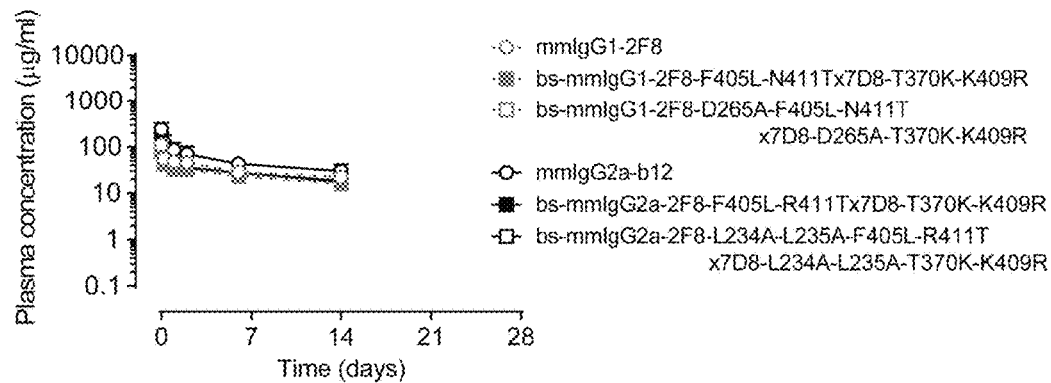
FIGS. 10A and 10B: Total antibody plasma concentration over time (FIG. 10A) and plasma clearance rate (FIG. 10B) of mmIgG1-derived or mmIgG2a-derived bispecific antibodies in C57131/6J mice. Six groups of mice (3 mice per group) were injected with the indicated antibodies (100 μg/mice). Blood samples were drawn at different times and plasma concentrations were determined by antigen-specific ELISA. Data represent mean±SD.
Figure 10B:
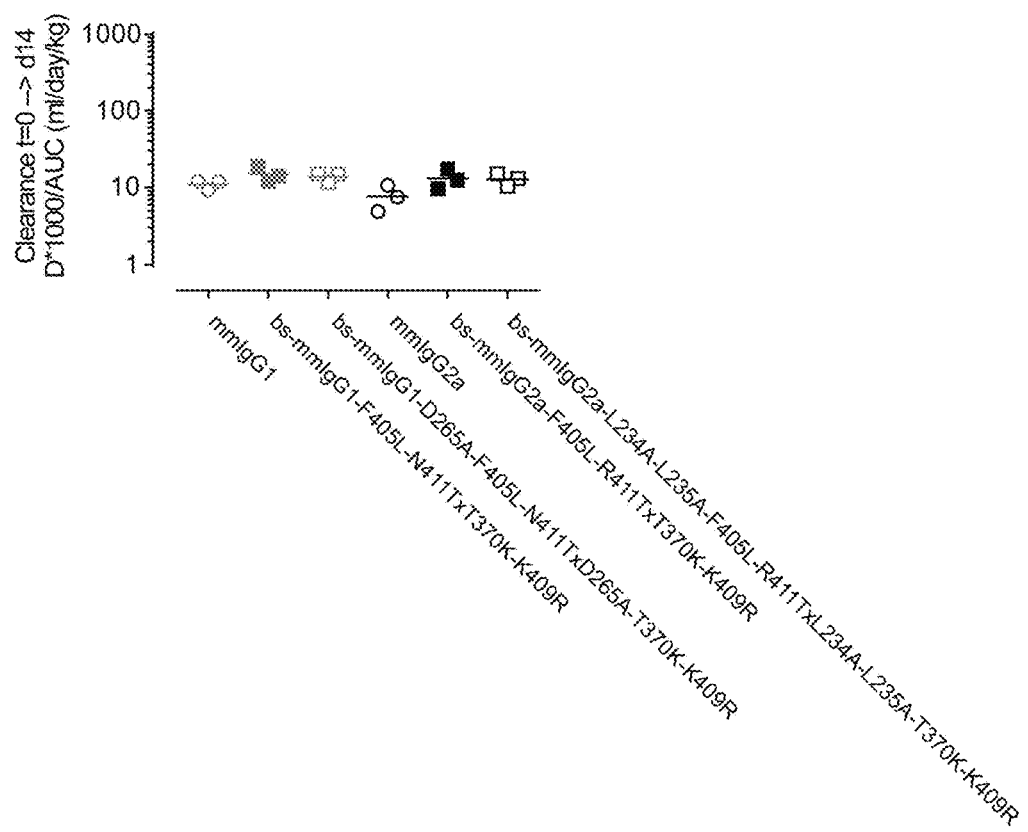

FIG. 10 A shows total antibody plasma concentrations over time. The shape of the PK profiles is identical in all groups. FIG. 10B shows plasma clearance rates. No statistically significant differences in the clearance rates were observed between all groups. These data indicate that introduction of the matching mutations F405L-N411T and T370K-K409R in mmIgG1 or F405L-R411T and T370K-K409R in mmIgG2a, nor the D265A mutation in mmIgG1 or the L234A-L235A mutations in mmIgG2a had any effect on the pharmacokinetic properties.

Example 18: In Vivo Anti-Tumor Efficacy of Bispecific Mouse Antibody Variants in T-Cell Redirection Model To assess whether mouse T-cells could be redirected to tumor cells in vivo, various bispecific antibodies were generated using anti-gp75 (CTA99; tumor-specific arm), anti-gp120 (b12; irrelevant arm) and anti-mouse CD3E (145-2C11) antibody heavy and light chain variable region sequences.

CTA99 (WO 2009114585 A1) hereby incorporated by reference in its entirety, including sequence disclosures.

VH CTA99, SEQ ID NO: 66:
EVQLQQSGAELVRPGALVKLSCKTSGFNIKDYFLHWVRORPDOGLEWIGW
INPDNGNTVYDPKFQGTASLTADTSSNTVYLQLSGLTSEDTAVYFCTRRD
YTYEKAALDYWGQGASVIVSS

VL CTA99, SEQ ID NO: 67:
AIQMSQSPASLSASVGETVTITCRASGNIYNYLAWYQQKQGKSPHLLVYD
AKTLADGVPSRFSGSGSGTQYSLKISSLOTEDSGNYYCQHFWSLPFTFGS
GTKLEIK b12 (Barbas, C F. J Mol Biol. 1993 Apr. 5; 230(3):812-23) hereby incorporated by reference in its entirety, including sequence disclosures.

VH b12, SEQ ID NO: 68:
QVQLVQSGAEVKKPGASVKVSCQASGYRFSNFVIHWVRQAPGQRFEWMGW
INPYNGNKEFSAKFQDRVTFTADTSANTAYMELRSLRSADTAVYYCARVG
PYSWDDSPODNYYMDVWGKGTTVIVSS

-continued

VL b12, SEQ ID NO: 69:
EIVLTQSPGTLSLSPGERATFSCRSSHSIRSRRVAWYQHKPGQAPRLVIH
GVSNRASGISDRFSGSGSGTDFTLTITRVEPEDFALYYCQVYGASSYTFG
QGTKLERK

The VH and VL sequences were introduced into chimeric constructs containing mouse IgG2a-derived constant regions that contained L234A-L235A-T370K-K409R or L234A-L235A-F405L-R411T mutations. This resulted in the following constructs:

TABLE 6

| gp75 and mmCD3 chimeric constructs | |
|---|---|
| mmIgG2a-CTA99-L234A-L235A-T370K-K409R | mmIgG2a-145-2C11-L234A-L235A-F405L-R411T |
| mmIgG2a-b12-L234A-L235A-T370K-K409R | mmIgG2a-b12-L234A-L235A-F405L-R411T |

Bispecific antibodies using these constructs (Table 6) and mmIgG1-7D8-T370K-K409R (Table 3) were generated (as described in Example 9) and HIC analysis (as described in Example 8) was performed to determine the amount of bispecific product.

The mice in this study were housed in a barrier unit of the Central Laboratory Animal Facility (Utrecht, The Netherlands) and kept in filter-top cages with water and food provided ad libitum. All experiments were approved by the Utrecht University animal ethics committee. 8-11 weeks old, female C57131/6J mice (Charles River Laboratories) were injected subcutaneously into the right flank with $1 \times 10^5$ B16/F10 cells (ATCC; CRL-6475) in PBS. The B16/F10 cells were previously cultured to 70% confluency in IMDM medium supplemented with HEPES, L-Glutamine (Lonza, cat #: BE12-722F), 10% Donor Bovine Serum with Iron (Life Technologies, 10371-029) and Pen/Strep (Lonza, cat DE17-603E).

The mice received intravenous injections of mmIgG2a-derived 145-2C11×CTA99 bispecific antibodies (bs-mmIgG2a-L234A-L235A-F405L-R411T×L234A-L235A-T370K-K409R) or their monovalent counterparts (145-2C11×b12 and b12×CTA99) at 6 and 8 (or 9) days after tumor cell injection. The antibodies were dosed at concentrations ranging from 0.005 mg/kg to 5 mg/kg. Tumor-size was subsequently followed over time.

Figure 11A:
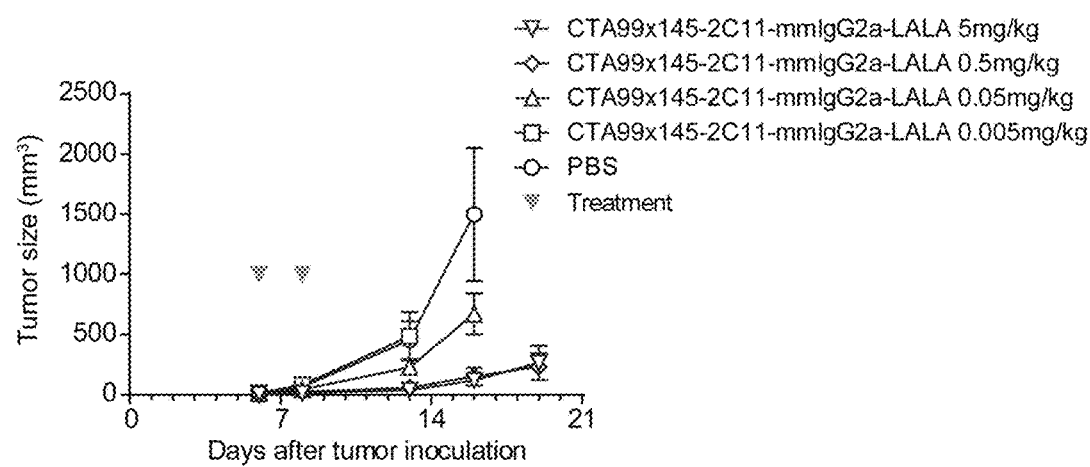
FIGS. 11A and 11B: Evaluation of the in vivo efficacy of mmIgG2a-derived 145-2C11×CTA99 bispecific antibodies in a syngeneic xenograft model with gp75-expressing B16/F10 tumor cells. On day 6, when average tumor size was ~200-400 mm3, mice were randomized (n=8 or 9 per group) and treated intravenously with the indicated doses, followed by a second dose at day 8 (FIG. 11A) or 9 (FIG. 11B) (arrowheads indicate treatment days). Data represent mean tumor volumes±SEM.
Figure 11B:
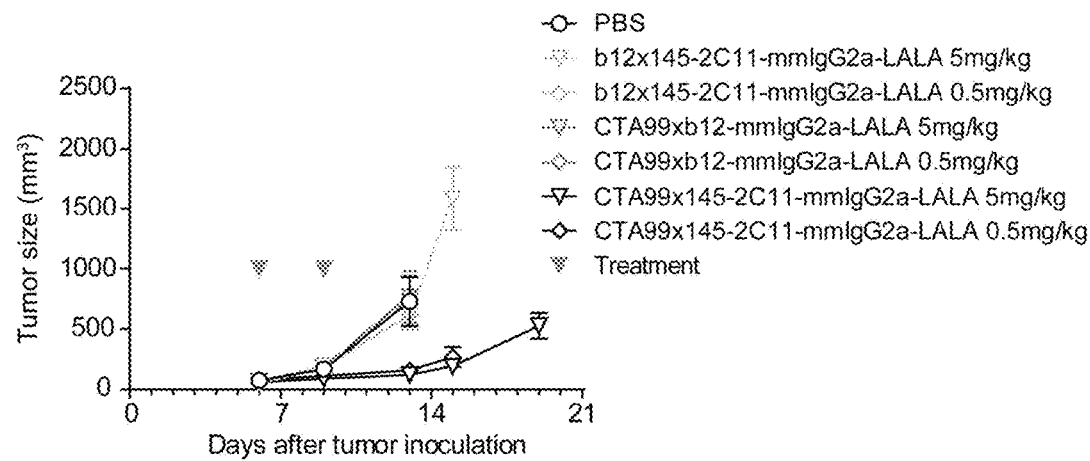

FIG. 11 shows that whereas doses of 0.005 mg/kg and 0.05 mg/kg mmIgG2a-derived 145-2C11×CTA99 bispecific antibody did not inhibit B16/F10 tumor growth, doses of 0.5 mg/kg or 5 mg/kg mmIgG2a-derived 145-2C11×CTA99 bispecific antibody could inhibit tumor growth, compared to equal doses of their monovalent counterparts (145-2C11×b12 and b12×CTA99).

The invention claimed is:

1. A bispecific antibody comprising first and second IgG heavy and light chain constant and variable domains (regions) wherein:
the first IgG heavy chain comprising a first Fc region, said first Fc region comprising a first CH3 domain; and
the second IgG heavy chain comprising a second Fc region, said second Fc region comprising a second CH3 domain,
wherein the first and second Fc regions originate from a rodent species, and wherein
(a) the first CH3 domain comprises at position 370 and Arg at position 409, and
(b) the second CH3 domain comprises Leu at position 405 when using EU numbering index.

2. The bispecific antibody according to claim 1, wherein the Fc regions are of mouse or rat origin.

3. The bispecific antibody according to claim 1, wherein the first and second IgG heavy chains comprise variable regions that are of human origin or that are humanized variable regions.

4. The bispecific antibody according to claim 1, wherein the first and second IgG heavy chains comprise human variable regions and rodent Fc regions.

5. The bispecific antibody according to claim 4, wherein the rodent Fc regions are *Mus musculus* (mm) or *Rattus norvegicus* (rn) Fc regions.

6. The bispecific antibody according to claim 1, wherein the second CH3 domain further comprises a Thr at position 411.

7. The bispecific antibody according to claim 1, wherein the first IgG heavy chain comprises Asp (D) at position 253.

8. A conjugated bispecific antibody comprising the bispecific antibody according to claim 1, wherein the second IgG heavy chain comprises Thr (T) and Leu (L) at positions 307 and/or 309, respectively.

9. The bispecific antibody according to claim 1, wherein said bispecific antibody is conjugated to a prodrug, peptide, drug, or a toxin.

10. The bispecific antibody according to claim 1, wherein the first and second IgG heavy chains both comprise a CH1 region, a hinge region, a CH2 region, and a CH3 region.

11. The bispecific antibody according to claim 1, wherein said bispecific antibody is a full-length antibody.

12. The bispecific antibody according to claim 1, wherein
(a) the Fc region of the first IgG heavy chain is a *Mus musculus* (mm) or *Rattus norvegicus* (rn) Fc region selected from the group consisting of mmIgG1, mmIgG2a, mmIgG2b, mmIgG2c, mmIgG3, rnIgG1, rnIgG2a, rnIgG2b, and rnIgG2c, and
(b) the Fc region of the second IgG heavy chain is a *Mus musculus* (mm) or *Rattus norvegicus* (rn) Fc region selected from the group consisting of mmIgG1, mmIgG2a, mmIgG2b, mmIgG2c, mmIgG3, rnIgG1, rnIgG2a, rnIgG2b, and rnIgG2c.

13. The bispecific antibody according to claim 1, wherein the Fc regions of both said first and said second IgG heavy chains are of the same isotype and species.

14. The bispecific antibody according to claim 1, wherein the Fc regions of both said first and said second IgG heavy chains are of *Mus musculus* (mm) origin and are both of the same isotype.

* * * * *

UNITED STATES PATENT AND TRADEMARK OFFICE
CERTIFICATE OF CORRECTION

PATENT NO. : 10,865,253 B2
APPLICATION NO. : 15/536143
DATED : December 15, 2020
INVENTOR(S) : Aran F. Labrijn et al.

Page 1 of 1

It is certified that error appears in the above-identified patent and that said Letters Patent is hereby corrected as shown below:

On the Title Page

At Column 1, in item (30), Line 1 of the "Foreign Application Priority Data" section, delete "2014 00744" and insert --PA 2014 00744--.

In the Claims

At Column 95, Claim number 1, Line number 25, delete "the first IgG heavy chain comprising a first Fc region, said" and insert --the first IgG heavy chain comprises a first Fc region, said--.

At Column 95, Claim number 1, Line number 27, delete "the second IgG heavy chain comprising a second Fc" and insert --the second IgG heavy chain comprises a second Fc--.

At Column 95, Claim number 1, Line number 32, delete "(a) the first CH3 domain comprises at position 370 and" and insert --(a) the first CH3 domain comprises Lys at position 370 and--.

At Column 96, Claim number 8, Line numbers 21 and 22, delete "A conjugated bispecific antibody comprising the bispecific antibody according to claim 1, wherein the second IgG" and insert --The bispecific antibody according to claim 1, wherein the second IgG--.

At Column 96, Claim number 9, Line number 25, delete "The bispecific antibody according to claim 1" and insert --A conjugated bispecific antibody comprising the bispecific antibody according to claim 1,--.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 69

<210> SEQ ID NO 1
<211> LENGTH: 98
<212> TYPE: PRT
<213> ORGANISM: homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 2
<211> LENGTH: 108
<212> TYPE: PRT
<213> ORGANISM: homo sapiens

<400> SEQUENCE: 2

Glu Leu Leu Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Lys Phe Asn Trp Tyr Val Asp
        35                  40                  45
```

Gly Val Glu Val His Asn Ala Lys Thr Lys Pro Arg Glu Glu Gln Tyr
          50                  55                  60

Asn Ser Thr Tyr Arg Val Val Ser Val Leu Thr Val Leu His Gln Asp
 65                  70                  75                  80

Trp Leu Asn Gly Lys Glu Tyr Lys Cys Lys Val Ser Asn Lys Ala Leu
                 85                  90                  95

Pro Ala Pro Ile Glu Lys Thr Ile Ser Lys Ala Lys
            100                 105

<210> SEQ ID NO 3
<211> LENGTH: 107
<212> TYPE: PRT
<213> ORGANISM: homo sapiens

<400> SEQUENCE: 3

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 4
<211> LENGTH: 97
<212> TYPE: PRT
<213> ORGANISM: Mus musculus

<400> SEQUENCE: 4

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
                 20                  25                  30

Phe Pro Glu Pro Val Thr Val Thr Trp Asn Ser Gly Ser Leu Ser Ser
             35                  40                  45

Gly Val His Thr Phe Pro Ala Val Leu Glu Ser Asp Leu Tyr Thr Leu
 50                  55                  60

Ser Ser Ser Val Thr Val Pro Ser Ser Pro Arg Pro Ser Glu Thr Val
 65                  70                  75                  80

Thr Cys Asn Val Ala His Pro Ala Ser Ser Thr Lys Val Asp Lys Lys
                 85                  90                  95

Ile

<210> SEQ ID NO 5
<211> LENGTH: 97
<212> TYPE: PRT
<213> ORGANISM: Mus musculus

<400> SEQUENCE: 5

Ala Lys Thr Thr Ala Pro Ser Val Tyr Pro Leu Ala Pro Val Cys Gly

```
            1               5                   10                  15
Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
                35                  40                  45

Gly Val His Thr Phe Pro Ala Val Leu Gln Ser Asp Leu Tyr Thr Leu
            50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                    85                  90                  95

Ile

<210> SEQ ID NO 6
<211> LENGTH: 97
<212> TYPE: PRT
<213> ORGANISM: Mus musculus

<400> SEQUENCE: 6

Ala Lys Thr Thr Pro Pro Ser Val Tyr Pro Leu Ala Pro Gly Cys Gly
1               5                   10                  15

Asp Thr Thr Gly Ser Ser Val Thr Ser Gly Cys Leu Val Lys Gly Tyr
                20                  25                  30

Phe Pro Glu Pro Val Thr Val Thr Trp Asn Ser Gly Ser Leu Ser Ser
                35                  40                  45

Ser Val His Thr Phe Pro Ala Leu Leu Gln Ser Gly Leu Tyr Thr Met
            50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                    85                  90                  95

Leu

<210> SEQ ID NO 7
<211> LENGTH: 97
<212> TYPE: PRT
<213> ORGANISM: Mus musculus

<400> SEQUENCE: 7

Ala Thr Thr Thr Ala Pro Ser Val Tyr Pro Leu Val Pro Gly Cys Ser
1               5                   10                  15

Asp Thr Ser Gly Ser Ser Val Thr Leu Gly Cys Leu Val Lys Gly Tyr
                20                  25                  30

Phe Pro Glu Pro Val Thr Val Lys Trp Asn Tyr Gly Ala Leu Ser Ser
                35                  40                  45

Gly Val Arg Thr Val Ser Ser Val Leu Gln Ser Gly Phe Tyr Ser Leu
            50                  55                  60

Ser Ser Leu Val Thr Val Pro Ser Ser Thr Trp Pro Ser Gln Thr Val
65                  70                  75                  80

Ile Cys Asn Val Ala His Pro Ala Ser Lys Thr Glu Leu Ile Lys Arg
                    85                  90                  95

Ile

<210> SEQ ID NO 8
<211> LENGTH: 107
<212> TYPE: PRT
```

<213> ORGANISM: Mus musculus

<400> SEQUENCE: 8

Val Pro Glu Val Ser Ser Val Phe Ile Phe Pro Lys Pro Lys Asp
1               5                   10                  15

Val Leu Thr Ile Thr Leu Thr Pro Lys Val Thr Cys Val Val Asp
            20                  25                  30

Ile Ser Lys Asp Asp Pro Glu Val Gln Phe Ser Trp Phe Val Asp
        35                  40                  45

Val Glu Val His Thr Ala Gln Thr Gln Pro Arg Glu Glu Gln Phe Asn
    50                  55                  60

Ser Thr Phe Arg Ser Val Ser Glu Leu Pro Ile Met His Gln Asp Trp
65                  70                  75                  80

Leu Asn Gly Lys Glu Phe Lys Cys Arg Val Asn Ser Ala Ala Phe Pro
                85                  90                  95

Ala Pro Ile Glu Lys Thr Ile Ser Lys Thr Lys
            100                 105

<210> SEQ ID NO 9
<211> LENGTH: 110
<212> TYPE: PRT
<213> ORGANISM: Mus musculus

<400> SEQUENCE: 9

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ala Pro Ile Glu Arg Thr Ile Ser Lys Pro Lys
            100                 105                 110

<210> SEQ ID NO 10
<211> LENGTH: 110
<212> TYPE: PRT
<213> ORGANISM: Mus musculus

<400> SEQUENCE: 10

Ala Pro Asn Leu Glu Gly Gly Pro Ser Val Phe Ile Phe Pro Pro Asn
1               5                   10                  15

Ile Lys Asp Val Leu Met Ile Ser Leu Thr Pro Lys Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Ile Arg Val Val Ser Thr Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ser Pro Ile Glu Arg Thr Ile Ser Lys Ile Lys
            100                 105                 110

<210> SEQ ID NO 11
<211> LENGTH: 110
<212> TYPE: PRT
<213> ORGANISM: Mus musculus

<400> SEQUENCE: 11

Pro Gly Asn Ile Leu Gly Gly Pro Ser Val Phe Ile Phe Pro Pro Lys
1               5                   10                  15

Pro Lys Asp Ala Leu Met Ile Ser Leu Thr Pro Lys Val Thr Cys Val
            20                  25                  30

Val Val Asp Val Ser Glu Asp Asp Pro Asp Val His Val Ser Trp Phe
        35                  40                  45

Val Asp Asn Lys Glu Val His Thr Ala Trp Thr Gln Pro Arg Glu Ala
    50                  55                  60

Gln Tyr Asn Ser Thr Phe Arg Val Val Ser Ala Leu Pro Ile Gln His
65                  70                  75                  80

Gln Asp Trp Met Arg Gly Lys Glu Phe Lys Cys Lys Val Asn Asn Lys
                85                  90                  95

Ala Leu Pro Ala Pro Ile Glu Arg Thr Ile Ser Lys Pro Lys
            100                 105                 110

<210> SEQ ID NO 12
<211> LENGTH: 107
<212> TYPE: PRT
<213> ORGANISM: Mus musculus

<400> SEQUENCE: 12

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 13
<211> LENGTH: 97
<212> TYPE: PRT
<213> ORGANISM: Rattus norvegicus

<400> SEQUENCE: 13

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Trp Asn Ser Gly Ala Leu Ser Ser
        35                  40                  45

Gly Val His Thr Phe Pro Ala Val Leu Gln Ser Gly Leu Tyr Thr Leu
            50                  55                  60

Thr Ser Ser Val Thr Val Pro Ser Ser Thr Trp Pro Ser Gln Thr Val
 65                  70                  75                  80

Thr Cys Asn Val Ala His Pro Ala Ser Ser Thr Lys Val Asp Lys Lys
                     85                  90                  95

Ile

<210> SEQ ID NO 14
<211> LENGTH: 97
<212> TYPE: PRT
<213> ORGANISM: Rattus norvegicus

<400> SEQUENCE: 14

Ala Glu Thr Thr Ala Pro Ser Val Tyr Pro Leu Ala Pro Gly Thr Ala
 1               5                  10                  15

Leu Lys Ser Asn Ser Met Val Thr Leu Gly Cys Leu Val Lys Gly Tyr
             20                  25                  30

Phe Pro Glu Pro Val Thr Val Thr Trp Asn Ser Gly Ala Leu Ser Ser
         35                  40                  45

Gly Val His Thr Phe Pro Ala Val Leu Gln Ser Gly Leu Tyr Thr Leu
            50                  55                  60

Thr Ser Ser Val Thr Val Pro Ser Ser Thr Trp Ser Ser Gln Ala Val
 65                  70                  75                  80

Thr Cys Asn Val Ala His Pro Ala Ser Ser Thr Lys Val Asp Lys Lys
                     85                  90                  95

Ile

<210> SEQ ID NO 15
<211> LENGTH: 95
<212> TYPE: PRT
<213> ORGANISM: Rattus norvegicus

<400> SEQUENCE: 15

Ala Gln Thr Thr Ala Pro Ser Val Tyr Pro Leu Ala Pro Gly Cys Gly
 1               5                  10                  15

Asp Thr Thr Ser Ser Thr Val Thr Leu Gly Cys Leu Val Lys Gly Tyr
             20                  25                  30

Phe Pro Glu Pro Val Thr Val Thr Trp Asn Ser Gly Ala Leu Ser Ser
         35                  40                  45

Asp Val His Thr Phe Pro Ala Val Leu Gln Ser Gly Leu Tyr Thr Leu
            50                  55                  60

Thr Ser Ser Val Thr Ser Ser Thr Trp Pro Ser Gln Thr Val Thr Cys
 65                  70                  75                  80

Asn Val Ala His Pro Ala Ser Ser Thr Lys Val Asp Lys Lys Val
                 85                  90                  95

<210> SEQ ID NO 16
<211> LENGTH: 97
<212> TYPE: PRT
<213> ORGANISM: Rattus norvegicus

<400> SEQUENCE: 16

Ala Arg Thr Thr Ala Pro Ser Val Tyr Pro Leu Val Pro Gly Cys Ser
 1               5                  10                  15

Gly Thr Ser Gly Ser Leu Val Thr Leu Gly Cys Leu Val Lys Gly Tyr
             20                  25                  30

```
Phe Pro Glu Pro Val Thr Val Lys Trp Asn Ser Gly Ala Leu Ser Ser
             35                  40                  45

Gly Val His Thr Phe Pro Ala Val Leu Gln Ser Gly Leu Tyr Thr Leu
 50                  55                  60

Ser Ser Val Thr Val Pro Ser Ser Thr Trp Ser Ser Gln Thr Val
 65                  70                  75                  80

Thr Cys Ser Val Ala His Pro Ala Thr Lys Ser Asn Leu Ile Lys Arg
                 85                  90                  95

Ile
```

<210> SEQ ID NO 17
<211> LENGTH: 107
<212> TYPE: PRT
<213> ORGANISM: Rattus norvegicus

<400> SEQUENCE: 17

```
Gly Ser Glu Val Ser Ser Val Phe Ile Phe Pro Pro Lys Pro Lys Asp
 1               5                  10                  15

Val Leu Thr Ile Thr Leu Thr Pro Lys Val Thr Cys Val Val Val Asp
                 20                  25                  30

Ile Ser Gln Asp Asp Pro Glu Val His Phe Ser Trp Phe Val Asp Asp
             35                  40                  45

Val Glu Val His Thr Ala Gln Thr Arg Pro Pro Glu Glu Gln Phe Asn
 50                  55                  60

Ser Thr Phe Arg Ser Val Ser Glu Leu Pro Ile Leu His Gln Asp Trp
 65                  70                  75                  80

Leu Asn Gly Arg Thr Phe Arg Cys Lys Val Thr Ser Ala Ala Phe Pro
                 85                  90                  95

Ser Pro Ile Glu Lys Thr Ile Ser Lys Pro Glu
            100                 105
```

<210> SEQ ID NO 18
<211> LENGTH: 107
<212> TYPE: PRT
<213> ORGANISM: Rattus norvegicus

<400> SEQUENCE: 18

```
Gly Ser Glu Val Ser Ser Val Phe Ile Phe Pro Pro Lys Thr Lys Asp
 1               5                  10                  15

Val Leu Thr Ile Thr Leu Thr Pro Lys Val Thr Cys Val Val Val Asp
                 20                  25                  30

Ile Ser Gln Asn Asp Pro Glu Val Arg Phe Ser Trp Phe Ile Asp Asp
             35                  40                  45

Val Glu Val His Thr Ala Gln Thr His Ala Pro Glu Lys Gln Ser Asn
 50                  55                  60

Ser Thr Leu Arg Ser Val Ser Glu Leu Pro Ile Val His Arg Asp Trp
 65                  70                  75                  80

Leu Asn Gly Lys Thr Phe Lys Cys Lys Val Asn Ser Gly Ala Phe Pro
                 85                  90                  95

Ala Pro Ile Glu Lys Ser Ile Ser Lys Pro Glu
            100                 105
```

<210> SEQ ID NO 19
<211> LENGTH: 110
<212> TYPE: PRT
<213> ORGANISM: Rattus norvegicus

<400> SEQUENCE: 19

```
Val Pro Glu Leu Leu Gly Gly Pro Ser Val Phe Ile Phe Pro Pro Lys
1               5                   10                  15

Pro Lys Asp Ile Leu Leu Ile Ser Gln Asn Ala Lys Val Thr Cys Val
            20                  25                  30

Val Val Asp Val Ser Glu Glu Glu Pro Asp Val Gln Phe Ser Trp Phe
            35                  40                  45

Val Asn Asn Val Glu Val His Thr Ala Gln Thr Gln Pro Arg Glu Glu
50                  55                  60

Gln Tyr Asn Ser Thr Phe Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Ala Leu Pro Ser Pro Ile Glu Lys Thr Ile Ser Lys Pro Lys
            100                 105                 110
```

<210> SEQ ID NO 20
<211> LENGTH: 108
<212> TYPE: PRT
<213> ORGANISM: Rattus norvegicus

<400> SEQUENCE: 20

```
Asp Asn Leu Gly Arg Pro Ser Val Phe Ile Phe Pro Pro Lys Pro Lys
1               5                   10                  15

Asp Ile Leu Met Ile Thr Leu Thr Pro Lys Val Thr Cys Val Val Val
            20                  25                  30

Asp Val Ser Glu Glu Glu Pro Asp Val Gln Phe Ser Trp Phe Val Asp
            35                  40                  45

Asn Val Arg Val Phe Thr Ala Gln Thr Gln Pro His Glu Glu Gln Leu
50                  55                  60

Asn Gly Thr Phe Arg Val Val Ser Thr Leu His Ile Gln His Gln Asp
65                  70                  75                  80

Trp Met Ser Gly Lys Glu Phe Lys Cys Lys Val Asn Asn Lys Asp Leu
                85                  90                  95

Pro Ser Pro Ile Glu Lys Thr Ile Ser Lys Pro Arg
            100                 105
```

<210> SEQ ID NO 21
<211> LENGTH: 107
<212> TYPE: PRT
<213> ORGANISM: Rattus norvegicus

<400> SEQUENCE: 21

```
Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
            20                  25                  30

Tyr Pro Arg Asp Ile Ser Val Lys Trp Lys Ile Asp Gly Thr Glu Arg
            35                  40                  45

Arg Asp Gly Val Leu Asp Ser Val Thr Asp Gln Asp Ser Lys Asp Ser
50                  55                  60

Thr Tyr Ser Met Ser Ser Thr Leu Ser Leu Thr Lys Ala Asp Tyr Glu
65                  70                  75                  80

Ser His Asn Leu Tyr Thr Cys Glu Val Val His Lys Thr Ser Ser Ser
                85                  90                  95

Pro Val Val Lys Ser Phe Asn Arg Asn Glu Cys
            100                 105
```

<210> SEQ ID NO 22
<211> LENGTH: 323
<212> TYPE: PRT
<213> ORGANISM: Mus musculus

<400> SEQUENCE: 22

Lys Thr Thr Pro Pro Ser Val Tyr Pro Leu Ala Pro Gly Ser Ala Ala
1               5                   10                  15

Gln Thr Asn Ser Met Val Thr Leu Gly Cys Leu Val Lys Gly Tyr Phe
            20                  25                  30

Pro Glu Pro Val Thr Val Thr Trp Asn Ser Gly Ser Leu Ser Ser Gly
        35                  40                  45

Val His Thr Phe Pro Ala Val Leu Glu Ser Asp Leu Tyr Thr Leu Ser
    50                  55                  60

Ser Ser Val Thr Val Pro Ser Ser Pro Arg Pro Ser Glu Thr Val Thr
65                  70                  75                  80

Cys Asn Val Ala His Pro Ala Ser Ser Thr Lys Val Asp Lys Lys Ile
                85                  90                  95

Val Pro Arg Asp Cys Gly Cys Lys Pro Cys Ile Cys Thr Val Pro Glu
            100                 105                 110

Val Ser Ser Val Phe Ile Phe Pro Pro Lys Pro Lys Asp Val Leu Thr
        115                 120                 125

Ile Thr Leu Thr Pro Lys Val Thr Cys Val Val Val Asp Ile Ser Lys
    130                 135                 140

Asp Asp Pro Glu Val Gln Phe Ser Trp Phe Val Asp Asp Val Glu Val
145                 150                 155                 160

His Thr Ala Gln Thr Gln Pro Arg Glu Glu Gln Phe Asn Ser Thr Phe
                165                 170                 175

Arg Ser Val Ser Glu Leu Pro Ile Met His Gln Asp Trp Leu Asn Gly
            180                 185                 190

Lys Glu Phe Lys Cys Arg Val Asn Ser Ala Ala Phe Pro Ala Pro Ile
        195                 200                 205

Glu Lys Thr Ile Ser Lys Thr Lys Gly Arg Pro Lys Ala Pro Gln Val
    210                 215                 220

Tyr Thr Ile Pro Pro Pro Lys Glu Gln Met Ala Lys Asp Lys Val Ser
225                 230                 235                 240

Leu Thr Cys Met Ile Thr Asp Phe Phe Pro Glu Asp Ile Thr Val Glu
                245                 250                 255

Trp Gln Trp Asn Gly Gln Pro Ala Glu Asn Tyr Lys Asn Thr Gln Pro
            260                 265                 270

Ile Met Asn Thr Asn Gly Ser Tyr Phe Val Tyr Ser Lys Leu Asn Val
        275                 280                 285

Gln Lys Ser Asn Trp Glu Ala Gly Asn Thr Phe Thr Cys Ser Val Leu
    290                 295                 300

His Glu Gly Leu His Asn His Thr Glu Lys Ser Leu Ser His Ser
305                 310                 315                 320

Pro Gly Lys

<210> SEQ ID NO 23
<211> LENGTH: 330
<212> TYPE: PRT
<213> ORGANISM: Mus musculus

<400> SEQUENCE: 23

-continued

```
Ala Lys Thr Thr Ala Pro Ser Val Tyr Pro Leu Ala Pro Val Cys Gly
  1               5                  10                  15

Asp Thr Thr Gly Ser Ser Val Thr Leu Gly Cys Leu Val Lys Gly Tyr
             20                  25                  30

Phe Pro Glu Pro Val Thr Leu Thr Trp Asn Ser Gly Ser Leu Ser Ser
         35                  40                  45

Gly Val His Thr Phe Pro Ala Val Leu Gln Ser Asp Leu Tyr Thr Leu
 50                  55                  60

Ser Ser Ser Val Thr Val Thr Ser Ser Thr Trp Pro Ser Gln Ser Ile
 65                  70                  75                  80

Thr Cys Asn Val Ala His Pro Ala Ser Ser Thr Lys Val Asp Lys Lys
                 85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 24
<211> LENGTH: 336
<212> TYPE: PRT
<213> ORGANISM: Mus musculus

<400> SEQUENCE: 24

```
Ala Lys Thr Thr Pro Pro Ser Val Tyr Pro Leu Ala Pro Gly Cys Gly
  1               5                  10                  15

Asp Thr Thr Gly Ser Ser Val Thr Ser Gly Cys Leu Val Lys Gly Tyr
             20                  25                  30

Phe Pro Glu Pro Val Thr Val Thr Trp Asn Ser Gly Ser Leu Ser Ser
         35                  40                  45
```

```
Ser Val His Thr Phe Pro Ala Leu Leu Gln Ser Gly Leu Tyr Thr Met
 50                  55                  60

Ser Ser Ser Val Thr Val Pro Ser Ser Thr Trp Pro Ser Gln Thr Val
 65                  70                  75                  80

Thr Cys Ser Val Ala His Pro Ala Ser Ser Thr Thr Val Asp Lys Lys
                 85                  90                  95

Leu Glu Pro Ser Gly Pro Ile Ser Thr Ile Asn Pro Cys Pro Pro Cys
             100                 105                 110

Lys Glu Cys His Lys Cys Pro Ala Pro Asn Leu Glu Gly Gly Pro Ser
         115                 120                 125

Val Phe Ile Phe Pro Pro Asn Ile Lys Asp Val Leu Met Ile Ser Leu
130                 135                 140

Thr Pro Lys Val Thr Cys Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Thr Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335

<210> SEQ ID NO 25
<211> LENGTH: 334
<212> TYPE: PRT
<213> ORGANISM: Mus musculus

<400> SEQUENCE: 25

Lys Thr Thr Ala Pro Ser Val Tyr Pro Leu Ala Pro Val Cys Gly Gly
1               5                  10                  15

Thr Thr Gly Ser Ser Val Thr Leu Gly Cys Leu Val Lys Gly Tyr Phe
            20                  25                  30

Pro Glu Pro Val Thr Leu Thr Trp Asn Ser Gly Ser Leu Ser Ser Gly
        35                  40                  45

Val His Thr Phe Pro Ala Leu Leu Gln Ser Gly Leu Tyr Thr Leu Ser
    50                  55                  60

Ser Ser Val Thr Val Thr Ser Asn Thr Trp Pro Ser Gln Thr Ile Thr
65                  70                  75                  80

Cys Asn Val Ala His Pro Ala Ser Ser Thr Lys Val Asp Lys Lys Ile
```

```
            85                  90                  95
Glu Pro Arg Val Pro Ile Thr Gln Asn Pro Cys Pro Leu Lys Glu
            100                 105                 110

Cys Pro Cys Ala Ala Pro Asp Leu Leu Gly Gly Pro Ser Val Phe
            115                 120                 125

Ile Phe Pro Pro Lys Ile Lys Asp Val Leu Met Ile Ser Leu Ser Pro
130                 135                 140

Met Val Thr Cys Val Val Val Asp Val Ser Glu Asp Pro Asp Val
145                 150                 155                 160

Gln Ile Ser Trp Phe Val Asn Asn Val Glu Val His Thr Ala Gln Thr
                165                 170                 175

Gln Thr His Arg Glu Asp Tyr Asn Ser Thr Leu Arg Val Val Ser Ala
            180                 185                 190

Leu Pro Ile Gln His Gln Asp Trp Met Ser Gly Lys Glu Phe Lys Cys
            195                 200                 205

Lys Val Asn Asn Arg Ala Leu Pro Ser Pro Ile Glu Lys Thr Ile Ser
            210                 215                 220

Lys Pro Arg Gly Pro Val Arg Ala Pro Gln Val Tyr Val Leu Pro Pro
225                 230                 235                 240

Pro Ala Glu Glu Met Thr Lys Lys Glu Phe Ser Leu Thr Cys Met Ile
                245                 250                 255

Thr Gly Phe Leu Pro Ala Glu Ile Ala Val Asp Trp Thr Ser Asn Gly
            260                 265                 270

Arg Thr Glu Gln Asn Tyr Lys Asn Thr Ala Thr Val Leu Asp Ser Asp
            275                 280                 285

Gly Ser Tyr Phe Met Tyr Ser Lys Leu Arg Val Gln Lys Ser Thr Trp
            290                 295                 300

Glu Arg Gly Ser Leu Phe Ala Cys Ser Val Val His Glu Val Leu His
305                 310                 315                 320

Asn His Leu Thr Thr Lys Thr Ile Ser Arg Ser Leu Gly Lys
                325                 330

<210> SEQ ID NO 26
<211> LENGTH: 330
<212> TYPE: PRT
<213> ORGANISM: Mus musculus

<400> SEQUENCE: 26

Ala Thr Thr Thr Ala Pro Ser Val Tyr Pro Leu Val Pro Gly Cys Ser
1               5                   10                  15

Asp Thr Ser Gly Ser Ser Val Thr Leu Gly Cys Leu Val Lys Gly Tyr
                20                  25                  30

Phe Pro Glu Pro Val Thr Val Lys Trp Asn Tyr Gly Ala Leu Ser Ser
            35                  40                  45

Gly Val Arg Thr Val Ser Ser Val Leu Gln Ser Gly Phe Tyr Ser Leu
        50                  55                  60

Ser Ser Leu Val Thr Val Pro Ser Ser Thr Trp Pro Ser Gln Thr Val
65                  70                  75                  80

Ile Cys Asn Val Ala His Pro Ala Ser Lys Thr Glu Leu Ile Lys Arg
                85                  90                  95

Ile Glu Pro Arg Ile Pro Lys Pro Ser Thr Pro Pro Gly Ser Ser Cys
            100                 105                 110

Pro Pro Gly Asn Ile Leu Gly Gly Pro Ser Val Phe Ile Phe Pro Pro
            115                 120                 125
```

Lys Pro Lys Asp Ala Leu Met Ile Ser Leu Thr Pro Lys Val Thr Cys
            130                 135                 140

Val Val Val Asp Val Ser Glu Asp Asp Pro Asp Val His Val Ser Trp
145                 150                 155                 160

Phe Val Asp Asn Lys Glu Val His Thr Ala Trp Thr Gln Pro Arg Glu
                165                 170                 175

Ala Gln Tyr Asn Ser Thr Phe Arg Val Val Ser Ala Leu Pro Ile Gln
                180                 185                 190

His Gln Asp Trp Met Arg Gly Lys Glu Phe Lys Cys Lys Val Asn Asn
            195                 200                 205

Lys Ala Leu Pro Ala Pro Ile Glu Arg Thr Ile Ser Lys Pro Lys Gly
210                 215                 220

Arg Ala Gln Thr Pro Gln Val Tyr Thr Ile Pro Pro Arg Glu Gln
225                 230                 235                 240

Met Ser Lys Lys Lys Val Ser Leu Thr Cys Leu Val Thr Asn Phe Phe
                245                 250                 255

Ser Glu Ala Ile Ser Val Glu Trp Glu Arg Asn Gly Glu Leu Glu Gln
            260                 265                 270

Asp Tyr Lys Asn Thr Pro Pro Ile Leu Asp Ser Asp Gly Thr Tyr Phe
            275                 280                 285

Leu Tyr Ser Lys Leu Thr Val Asp Thr Asp Ser Trp Leu Gln Gly Glu
            290                 295                 300

Ile Phe Thr Cys Ser Val Val His Glu Ala Leu His Asn His His Thr
305                 310                 315                 320

Gln Lys Asn Leu Ser Arg Ser Pro Gly Lys
            325                 330

<210> SEQ ID NO 27
<211> LENGTH: 106
<212> TYPE: PRT
<213> ORGANISM: Mus musculus

<400> SEQUENCE: 27

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
50              55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 28
<211> LENGTH: 326
<212> TYPE: PRT
<213> ORGANISM: Rattus Norvegicus

<400> SEQUENCE: 28

Ala Glu Thr Thr Ala Pro Ser Val Tyr Pro Leu Ala Pro Gly Thr Ala
1               5                   10                  15

```
Leu Lys Ser Asn Ser Met Val Thr Leu Gly Cys Leu Val Lys Gly Tyr
             20                  25                  30
Phe Pro Glu Pro Val Thr Val Thr Trp Asn Ser Gly Ala Leu Ser Ser
         35                  40                  45
Gly Val His Thr Phe Pro Ala Val Leu Gln Ser Gly Leu Tyr Thr Leu
     50                  55                  60
Thr Ser Ser Val Thr Val Pro Ser Ser Thr Trp Pro Ser Gln Thr Val
 65                  70                  75                  80
Thr Cys Asn Val Ala His Pro Ala Ser Ser Thr Lys Val Asp Lys Lys
                 85                  90                  95
Ile Val Pro Arg Asn Cys Gly Gly Asp Cys Lys Pro Cys Ile Cys Thr
            100                 105                 110
Gly Ser Glu Val Ser Ser Val Phe Ile Phe Pro Pro Lys Pro Lys Asp
        115                 120                 125
Val Leu Thr Ile Thr Leu Thr Pro Lys Val Thr Cys Val Val Val Asp
    130                 135                 140
Ile Ser Gln Asp Asp Pro Glu Val His Phe Ser Trp Phe Val Asp Asp
145                 150                 155                 160
Val Glu Val His Thr Ala Gln Thr Arg Pro Pro Glu Glu Gln Phe Asn
                165                 170                 175
Ser Thr Phe Arg Ser Val Ser Glu Leu Pro Ile Leu His Gln Asp Trp
            180                 185                 190
Leu Asn Gly Arg Thr Phe Arg Cys Lys Val Thr Ser Ala Ala Phe Pro
        195                 200                 205
Ser Pro Ile Glu Lys Thr Ile Ser Lys Pro Glu Gly Arg Thr Gln Val
    210                 215                 220
Pro His Val Tyr Thr Met Ser Pro Thr Lys Glu Glu Met Thr Gln Asn
225                 230                 235                 240
Glu Val Ser Ile Thr Cys Met Val Lys Gly Phe Tyr Pro Pro Asp Ile
                245                 250                 255
Tyr Val Glu Trp Gln Met Asn Gly Gln Pro Gln Glu Asn Tyr Lys Asn
            260                 265                 270
Thr Pro Pro Thr Met Asp Thr Asp Gly Ser Tyr Phe Leu Tyr Ser Lys
        275                 280                 285
Leu Asn Val Lys Lys Glu Lys Trp Gln Gln Gly Asn Thr Phe Thr Cys
    290                 295                 300
Ser Val Leu His Glu Gly Leu His Asn His His Thr Glu Lys Ser Leu
305                 310                 315                 320
Ser His Ser Pro Gly Lys
                325

<210> SEQ ID NO 29
<211> LENGTH: 322
<212> TYPE: PRT
<213> ORGANISM: Rattus Norvegicus

<400> SEQUENCE: 29

Ala Glu Thr Thr Ala Pro Ser Val Tyr Pro Leu Ala Pro Gly Thr Ala
 1               5                  10                  15
Leu Lys Ser Asn Ser Met Val Thr Leu Gly Cys Leu Val Lys Gly Tyr
             20                  25                  30
Phe Pro Glu Pro Val Thr Val Thr Trp Asn Ser Gly Ala Leu Ser Ser
         35                  40                  45
Gly Val His Thr Phe Pro Ala Val Leu Gln Ser Gly Leu Tyr Thr Leu
     50                  55                  60
```

```
Thr Ser Ser Val Thr Val Pro Ser Ser Thr Trp Ser Ser Gln Ala Val
 65                  70                  75                  80

Thr Cys Asn Val Ala His Pro Ala Ser Ser Thr Lys Val Asp Lys Lys
             85                  90                  95

Ile Val Pro Arg Glu Cys Asn Pro Cys Gly Cys Thr Gly Ser Glu Val
            100                 105                 110

Ser Ser Val Phe Ile Phe Pro Pro Lys Thr Lys Asp Val Leu Thr Ile
            115                 120                 125

Thr Leu Thr Pro Lys Val Thr Cys Val Val Val Asp Ile Ser Gln Asn
130                 135                 140

Asp Pro Glu Val Arg Phe Ser Trp Phe Ile Asp Asp Val Glu Val His
145                 150                 155                 160

Thr Ala Gln Thr His Ala Pro Glu Lys Gln Ser Asn Ser Thr Leu Arg
                165                 170                 175

Ser Val Ser Glu Leu Pro Ile Val His Arg Asp Trp Leu Asn Gly Lys
            180                 185                 190

Thr Phe Lys Cys Lys Val Asn Ser Gly Ala Phe Pro Ala Pro Ile Glu
        195                 200                 205

Lys Ser Ile Ser Lys Pro Glu Gly Thr Pro Arg Gly Pro Gln Val Tyr
210                 215                 220

Thr Met Ala Pro Pro Lys Glu Glu Met Thr Gln Ser Gln Val Ser Ile
225                 230                 235                 240

Thr Cys Met Val Lys Gly Phe Tyr Pro Pro Asp Ile Tyr Thr Glu Trp
                245                 250                 255

Lys Met Asn Gly Gln Pro Gln Glu Asn Tyr Lys Asn Thr Pro Pro Thr
            260                 265                 270

Met Asp Thr Asp Gly Ser Tyr Phe Leu Tyr Ser Lys Leu Asn Val Lys
        275                 280                 285

Lys Glu Thr Trp Gln Gln Gly Asn Thr Phe Thr Cys Ser Val Leu His
    290                 295                 300

Glu Gly Leu His Asn His His Thr Glu Lys Ser Leu Ser His Ser Pro
305                 310                 315                 320

Gly Lys

<210> SEQ ID NO 30
<211> LENGTH: 333
<212> TYPE: PRT
<213> ORGANISM: Rattus Norvegicus

<400> SEQUENCE: 30

Ala Gln Thr Thr Ala Pro Ser Val Tyr Pro Leu Ala Pro Gly Cys Gly
1               5                   10                  15

Asp Thr Thr Ser Ser Thr Val Thr Leu Gly Cys Leu Val Lys Gly Tyr
                20                  25                  30

Phe Pro Glu Pro Val Thr Val Thr Trp Asn Ser Gly Ala Leu Ser Ser
            35                  40                  45

Asp Val His Thr Phe Pro Ala Val Leu Gln Ser Gly Leu Tyr Thr Leu
        50                  55                  60

Thr Ser Ser Val Thr Ser Ser Trp Pro Ser Gln Thr Val Thr Cys
65                  70                  75                  80

Asn Val Ala His Pro Ala Ser Ser Thr Lys Val Asp Lys Lys Val Glu
            85                  90                  95

Arg Arg Asn Gly Gly Ile Gly His Lys Cys Pro Thr Cys Pro Thr Cys
            100                 105                 110
```

His Lys Cys Pro Val Pro Glu Leu Leu Gly Gly Pro Ser Val Phe Ile
            115                 120                 125

Phe Pro Pro Lys Pro Lys Asp Ile Leu Leu Ile Ser Gln Asn Ala Lys
130                 135                 140

Val Thr Cys Val Val Asp Val Ser Glu Glu Pro Asp Val Gln
145                 150                 155                 160

Phe Ser Trp Phe Val Asn Asn Val Glu Val His Thr Ala Gln Thr Gln
                165                 170                 175

Pro Arg Glu Glu Gln Tyr Asn Ser Thr Phe Arg Val Val Ser Ala Leu
            180                 185                 190

Pro Ile Gln His Gln Asp Trp Met Ser Gly Lys Glu Phe Lys Cys Lys
            195                 200                 205

Val Asn Asn Lys Ala Leu Pro Ser Pro Ile Glu Lys Thr Ile Ser Lys
            210                 215                 220

Pro Lys Gly Leu Val Arg Lys Pro Gln Val Tyr Val Met Gly Pro Pro
225                 230                 235                 240

Thr Glu Gln Leu Thr Glu Gln Thr Val Ser Leu Thr Cys Leu Thr Ser
                245                 250                 255

Gly Phe Leu Pro Asn Asp Ile Gly Val Glu Trp Thr Ser Asn Gly His
            260                 265                 270

Ile Glu Lys Asn Tyr Lys Asn Thr Glu Pro Val Met Asp Ser Asp Gly
            275                 280                 285

Ser Phe Phe Met Tyr Ser Lys Leu Asn Val Glu Arg Ser Arg Trp Asp
            290                 295                 300

Ser Arg Ala Pro Phe Val Cys Ser Val Val His Glu Gly Leu His Asn
305                 310                 315                 320

His His Val Glu Lys Ser Ile Ser Arg Pro Pro Gly Lys
            325                 330

<210> SEQ ID NO 31
<211> LENGTH: 329
<212> TYPE: PRT
<213> ORGANISM: Rattus Norvegicus

<400> SEQUENCE: 31

Ala Arg Thr Thr Ala Pro Ser Val Tyr Pro Leu Val Pro Gly Cys Ser
1               5                   10                  15

Gly Thr Ser Gly Ser Leu Val Thr Leu Gly Cys Leu Val Lys Gly Tyr
            20                  25                  30

Phe Pro Glu Pro Val Thr Val Lys Trp Asn Ser Gly Ala Leu Ser Ser
            35                  40                  45

Gly Val His Thr Phe Pro Ala Val Leu Gln Ser Gly Leu Tyr Thr Leu
        50                  55                  60

Ser Ser Ser Val Thr Val Pro Ser Ser Thr Trp Ser Ser Gln Thr Val
65                  70                  75                  80

Thr Cys Ser Val Ala His Pro Ala Thr Lys Ser Asn Leu Ile Lys Arg
                85                  90                  95

Ile Glu Pro Arg Arg Pro Lys Pro Arg Pro Thr Asp Ile Cys Ser
            100                 105                 110

Cys Asp Asp Asn Leu Gly Arg Pro Ser Val Phe Ile Phe Pro Pro Lys
            115                 120                 125

Pro Lys Asp Ile Leu Met Ile Thr Leu Thr Pro Lys Val Thr Cys Val
        130                 135                 140

Val Val Asp Val Ser Glu Glu Glu Pro Asp Val Gln Phe Ser Trp Phe

```
                145                 150                 155                 160
Val Asp Asn Val Arg Val Phe Thr Ala Gln Thr Gln Pro His Glu Glu
                    165                 170                 175

Gln Leu Asn Gly Thr Phe Arg Val Val Ser Thr Leu His Ile Gln His
                    180                 185                 190

Gln Asp Trp Met Ser Gly Lys Glu Phe Lys Cys Lys Val Asn Asn Lys
                    195                 200                 205

Asp Leu Pro Ser Pro Ile Glu Lys Thr Ile Ser Lys Pro Arg Gly Lys
                    210                 215                 220

Ala Arg Thr Pro Gln Val Tyr Thr Ile Pro Pro Arg Glu Gln Met
225                 230                 235                 240

Ser Lys Asn Lys Val Ser Leu Thr Cys Met Val Thr Ser Phe Tyr Pro
                    245                 250                 255

Ala Ser Ile Ser Val Glu Trp Glu Arg Asn Gly Glu Leu Glu Gln Asp
                    260                 265                 270

Tyr Lys Asn Thr Leu Pro Val Leu Asp Ser Asp Glu Ser Tyr Phe Leu
                    275                 280                 285

Tyr Ser Lys Leu Ser Val Asp Thr Asp Ser Trp Met Arg Gly Asp Ile
                    290                 295                 300

Tyr Thr Cys Ser Val Val His Glu Ala Leu His Asn His Thr Gln
305                 310                 315                 320

Lys Asn Leu Ser Arg Ser Pro Gly Lys
                    325

<210> SEQ ID NO 32
<211> LENGTH: 107
<212> TYPE: PRT
<213> ORGANISM: Rattus Norvegicus

<400> SEQUENCE: 32

Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
                    20                  25                  30

Tyr Pro Arg Asp Ile Ser Val Lys Trp Lys Ile Asp Gly Thr Glu Arg
                    35                  40                  45

Arg Asp Gly Val Leu Asp Ser Val Thr Asp Gln Asp Ser Lys Asp Ser
                50                  55                  60

Thr Tyr Ser Met Ser Ser Thr Leu Ser Leu Thr Lys Ala Asp Tyr Glu
65                  70                  75                  80

Ser His Asn Leu Tyr Thr Cys Glu Val Val His Lys Thr Ser Ser Ser
                    85                  90                  95

Pro Val Val Lys Ser Phe Asn Arg Asn Glu Cys
                    100                 105

<210> SEQ ID NO 33
<211> LENGTH: 97
<212> TYPE: PRT
<213> ORGANISM: Mus musculus

<400> SEQUENCE: 33

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                    20                  25                  30

Phe Pro Glu Pro Val Thr Val Thr Trp Asn Ser Gly Ser Leu Ser Ser
```

```
                35                  40                  45
Gly Val His Thr Phe Pro Ala Val Leu Glu Ser Asp Leu Tyr Thr Leu
         50                  55                  60
Ser Ser Ser Val Thr Val Pro Ser Ser Arg Pro Ser Glu Thr Val
 65                  70                  75                  80
Thr Cys Asn Val Ala His Pro Ala Ser Ser Thr Lys Val Asp Lys Lys
                 85                  90                  95
Ile

<210> SEQ ID NO 34
<211> LENGTH: 97
<212> TYPE: PRT
<213> ORGANISM: Mus musculus

<400> SEQUENCE: 34

Ala Lys Thr Thr Ala Pro Ser Val Tyr Pro Leu Ala Pro Val Cys Gly
 1               5                  10                  15
Asp Thr Thr Gly Ser Ser Val Thr Leu Gly Cys Leu Val Lys Gly Tyr
                20                  25                  30
Phe Pro Glu Pro Val Thr Leu Thr Trp Asn Ser Gly Ser Leu Ser Ser
                35                  40                  45
Gly Val His Thr Phe Pro Ala Val Leu Gln Ser Asp Leu Tyr Thr Leu
         50                  55                  60
Ser Ser Ser Val Thr Val Thr Ser Ser Thr Trp Pro Ser Gln Ser Ile
 65                  70                  75                  80
Thr Cys Asn Val Ala His Pro Ala Ser Ser Thr Lys Val Asp Lys Lys
                 85                  90                  95
Ile

<210> SEQ ID NO 35
<211> LENGTH: 97
<212> TYPE: PRT
<213> ORGANISM: Mus musculus

<400> SEQUENCE: 35

Ala Lys Thr Thr Pro Pro Ser Val Tyr Pro Leu Ala Pro Gly Cys Gly
 1               5                  10                  15
Asp Thr Thr Gly Ser Ser Val Thr Ser Gly Cys Leu Val Lys Gly Tyr
                20                  25                  30
Phe Pro Glu Pro Val Thr Val Thr Trp Asn Ser Gly Ser Leu Ser Ser
                35                  40                  45
Ser Val His Thr Phe Pro Ala Leu Leu Gln Ser Gly Leu Tyr Thr Met
         50                  55                  60
Ser Ser Ser Val Thr Val Pro Ser Ser Thr Trp Pro Ser Gln Thr Val
 65                  70                  75                  80
Thr Cys Ser Val Ala His Pro Ala Ser Ser Thr Thr Val Asp Lys Lys
                 85                  90                  95
Leu

<210> SEQ ID NO 36
<211> LENGTH: 97
<212> TYPE: PRT
<213> ORGANISM: Mus musculus

<400> SEQUENCE: 36

Ala Lys Thr Thr Ala Pro Ser Val Tyr Pro Leu Ala Pro Val Cys Gly
 1               5                  10                  15
```

```
Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
            35                  40                  45

Gly Val His Thr Phe Pro Ala Leu Leu Gln Ser Gly Leu Tyr Thr Leu
        50                  55                  60

Ser Ser Ser Val Thr Val Thr Ser Asn Thr Trp Pro Ser Gln Thr Ile
 65                  70                  75                  80

Thr Cys Asn Val Ala His Pro Ala Ser Ser Thr Lys Val Asp Lys Lys
                85                  90                  95

Ile
```

<210> SEQ ID NO 37
<211> LENGTH: 97
<212> TYPE: PRT
<213> ORGANISM: Mus musculus

<400> SEQUENCE: 37

```
Ala Thr Thr Thr Ala Pro Ser Val Tyr Pro Leu Val Pro Gly Cys Ser
 1               5                  10                  15

Asp Thr Ser Gly Ser Ser Val Thr Leu Gly Cys Leu Val Lys Gly Tyr
            20                  25                  30

Phe Pro Glu Pro Val Thr Val Lys Trp Asn Tyr Gly Ala Leu Ser Ser
            35                  40                  45

Gly Val Arg Thr Val Ser Ser Val Leu Gln Ser Gly Phe Tyr Ser Leu
        50                  55                  60

Ser Ser Leu Val Thr Val Pro Ser Ser Thr Trp Pro Ser Gln Thr Val
 65                  70                  75                  80

Ile Cys Asn Val Ala His Pro Ala Ser Lys Thr Glu Leu Ile Lys Arg
                85                  90                  95

Ile
```

<210> SEQ ID NO 38
<211> LENGTH: 13
<212> TYPE: PRT
<213> ORGANISM: Mus musculus

<400> SEQUENCE: 38

```
Val Pro Arg Asp Cys Gly Cys Lys Pro Cys Ile Cys Thr
 1               5                  10
```

<210> SEQ ID NO 39
<211> LENGTH: 16
<212> TYPE: PRT
<213> ORGANISM: Mus musculus

<400> SEQUENCE: 39

```
Glu Pro Arg Gly Pro Thr Ile Lys Pro Cys Pro Pro Cys Lys Cys Pro
 1               5                  10                  15
```

<210> SEQ ID NO 40
<211> LENGTH: 22
<212> TYPE: PRT
<213> ORGANISM: Mus musculus

<400> SEQUENCE: 40

```
Glu Pro Ser Gly Pro Ile Ser Thr Ile Asn Pro Cys Pro Pro Cys Lys
 1               5                  10                  15
```

Glu Cys His Lys Cys Pro
            20

<210> SEQ ID NO 41
<211> LENGTH: 21
<212> TYPE: PRT
<213> ORGANISM: Mus musculus

<400> SEQUENCE: 41

Glu Pro Arg Val Pro Ile Thr Gln Asn Pro Cys Pro Pro Leu Lys Glu
1               5                   10                  15

Cys Pro Pro Cys Ala
            20

<210> SEQ ID NO 42
<211> LENGTH: 16
<212> TYPE: PRT
<213> ORGANISM: Mus musculus

<400> SEQUENCE: 42

Glu Pro Arg Ile Pro Lys Pro Ser Thr Pro Pro Gly Ser Ser Cys Pro
1               5                   10                  15

<210> SEQ ID NO 43
<211> LENGTH: 110
<212> TYPE: PRT
<213> ORGANISM: Mus musculus

<400> SEQUENCE: 43

Ala Pro Asp Leu Leu Gly Gly Pro Ser Val Phe Ile Phe Pro Pro Lys
1               5                   10                  15

Ile Lys Asp Val Leu Met Ile Ser Leu Ser Pro Met Val Thr Cys Val
                20                  25                  30

Val Val Asp Val Ser Glu Asp Asp Pro Asp Val Gln Ile Ser Trp Phe
            35                  40                  45

Val Asn Asn Val Glu Val His Thr Ala Gln Thr Gln Thr His Arg Glu
        50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Arg
                85                  90                  95

Ala Leu Pro Ser Pro Ile Glu Lys Thr Ile Ser Lys Pro Arg
            100                 105                 110

<210> SEQ ID NO 44
<211> LENGTH: 107
<212> TYPE: PRT
<213> ORGANISM: Mus musculus

<400> SEQUENCE: 44

Gly Arg Pro Lys Ala Pro Gln Val Tyr Thr Ile Pro Pro Pro Lys Glu
1               5                   10                  15

Gln Met Ala Lys Asp Lys Val Ser Leu Thr Cys Met Ile Thr Asp Phe
                20                  25                  30

Phe Pro Glu Asp Ile Thr Val Glu Trp Gln Trp Asn Gly Gln Pro Ala
            35                  40                  45

Glu Asn Tyr Lys Asn Thr Gln Pro Ile Met Asp Thr Asn Gly Ser Tyr
        50                  55                  60

Phe Val Tyr Ser Lys Leu Asn Val Gln Lys Ser Asn Trp Glu Ala Gly
65                  70                  75                  80

-continued

```
Asn Thr Phe Thr Cys Ser Val Leu His Glu Gly Leu His Asn His His
                85                  90                  95

Thr Glu Lys Ser Leu Ser His Ser Pro Gly Lys
            100                 105

<210> SEQ ID NO 45
<211> LENGTH: 107
<212> TYPE: PRT
<213> ORGANISM: Mus musculus

<400> SEQUENCE: 45

Gly Ser Val Arg Ala Pro Gln Val Tyr Val Leu Pro Pro Glu Glu
1               5                   10                  15

Glu Met Thr Lys Lys Gln Val Thr Leu Thr Cys Met Val Thr Asp Phe
                20                  25                  30

Met Pro Glu Asp Ile Tyr Val Glu Trp Thr Asn Asn Gly Lys Thr Glu
            35                  40                  45

Leu Asn Tyr Lys Asn Thr Glu Pro Val Leu Asp Ser Asp Gly Ser Tyr
        50                  55                  60

Phe Met Tyr Ser Lys Leu Arg Val Glu Lys Lys Asn Trp Val Glu Arg
65                  70                  75                  80

Asn Ser Tyr Ser Cys Ser Val Val His Glu Gly Leu His Asn His His
                85                  90                  95

Thr Thr Lys Ser Phe Ser Arg Thr Pro Gly Lys
            100                 105

<210> SEQ ID NO 46
<211> LENGTH: 107
<212> TYPE: PRT
<213> ORGANISM: Mus musculus

<400> SEQUENCE: 46

Gly Leu Val Arg Ala Pro Gln Val Tyr Thr Leu Pro Pro Ala Glu
1               5                   10                  15

Gln Leu Ser Arg Lys Asp Val Ser Leu Thr Cys Leu Val Val Gly Phe
                20                  25                  30

Asn Pro Gly Asp Ile Ser Val Glu Trp Thr Ser Asn Gly His Thr Glu
            35                  40                  45

Glu Asn Tyr Lys Asp Thr Ala Pro Val Leu Asp Ser Asp Gly Ser Tyr
        50                  55                  60

Phe Ile Tyr Ser Lys Leu Asn Met Lys Thr Ser Lys Trp Glu Lys Thr
65                  70                  75                  80

Asp Ser Phe Ser Cys Asn Val Arg His Glu Gly Leu Lys Asn Tyr Tyr
                85                  90                  95

Leu Lys Lys Thr Ile Ser Arg Ser Pro Gly Lys
            100                 105

<210> SEQ ID NO 47
<211> LENGTH: 107
<212> TYPE: PRT
<213> ORGANISM: Mus musculus

<400> SEQUENCE: 47

Gly Pro Val Arg Ala Pro Gln Val Tyr Val Leu Pro Pro Ala Glu
1               5                   10                  15

Glu Met Thr Lys Lys Glu Phe Ser Leu Thr Cys Met Ile Thr Gly Phe
                20                  25                  30
```

```
Leu Pro Ala Glu Ile Ala Val Asp Trp Thr Ser Asn Gly Arg Thr Glu
             35                  40                  45

Gln Asn Tyr Lys Asn Thr Ala Thr Val Leu Asp Ser Asp Gly Ser Tyr
 50                  55                  60

Phe Met Tyr Ser Lys Leu Arg Val Gln Lys Ser Thr Trp Glu Arg Gly
65                  70                  75                  80

Ser Leu Phe Ala Cys Ser Val Val His Glu Val Leu His Asn His Leu
                 85                  90                  95

Thr Thr Lys Thr Ile Ser Arg Ser Leu Gly Lys
            100                 105

<210> SEQ ID NO 48
<211> LENGTH: 107
<212> TYPE: PRT
<213> ORGANISM: Mus musculus

<400> SEQUENCE: 48

Gly Arg Ala Gln Thr Pro Gln Val Tyr Thr Ile Pro Pro Arg Glu
1               5                  10                  15

Gln Met Ser Lys Lys Val Ser Leu Thr Cys Leu Val Thr Asn Phe
             20                  25                  30

Phe Ser Glu Ala Ile Ser Val Glu Trp Glu Arg Asn Gly Glu Leu Glu
             35                  40                  45

Gln Asp Tyr Lys Asn Thr Pro Pro Ile Leu Asp Ser Asp Gly Thr Tyr
 50                  55                  60

Phe Leu Tyr Ser Lys Leu Thr Val Asp Thr Ser Trp Leu Gln Gly
65                  70                  75                  80

Glu Ile Phe Thr Cys Ser Val Val His Glu Ala Leu His Asn His His
                 85                  90                  95

Thr Gln Lys Asn Leu Ser Arg Ser Pro Gly Lys
            100                 105

<210> SEQ ID NO 49
<211> LENGTH: 97
<212> TYPE: PRT
<213> ORGANISM: Rattus Norvegicus

<400> SEQUENCE: 49

Ala Glu Thr Thr Ala Pro Ser Val Tyr Pro Leu Ala Pro Gly Thr Ala
1               5                  10                  15

Leu Lys Ser Asn Ser Met Val Thr Leu Gly Cys Leu Val Lys Gly Tyr
             20                  25                  30

Phe Pro Glu Pro Val Thr Val Thr Trp Asn Ser Gly Ala Leu Ser Ser
             35                  40                  45

Gly Val His Thr Phe Pro Ala Val Leu Gln Ser Gly Leu Tyr Thr Leu
 50                  55                  60

Thr Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                 85                  90                  95

Ile

<210> SEQ ID NO 50
<211> LENGTH: 97
<212> TYPE: PRT
<213> ORGANISM: Rattus Norvegicus

<400> SEQUENCE: 50
```

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
            35                  40                  45

Gly Val His Thr Phe Pro Ala Val Leu Gln Ser Gly Leu Tyr Thr Leu
        50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
                85                  90                  95

Ile

<210> SEQ ID NO 51
<211> LENGTH: 95
<212> TYPE: PRT
<213> ORGANISM: Rattus Norvegicus

<400> SEQUENCE: 51

Ala Gln Thr Thr Ala Pro Ser Val Tyr Pro Leu Ala Pro Gly Cys Gly
1               5                   10                  15

Asp Thr Thr Ser Ser Thr Val Thr Leu Gly Cys Leu Val Lys Gly Tyr
            20                  25                  30

Phe Pro Glu Pro Val Thr Val Thr Trp Asn Ser Gly Ala Leu Ser Ser
            35                  40                  45

Asp Val His Thr Phe Pro Ala Val Leu Gln Ser Gly Leu Tyr Thr Leu
        50                  55                  60

Thr Ser Ser Val Thr Ser Ser Trp Pro Ser Gln Thr Val Thr Cys
65                  70                  75                  80

Asn Val Ala His Pro Ala Ser Ser Thr Lys Val Asp Lys Lys Val
                85                  90                  95

<210> SEQ ID NO 52
<211> LENGTH: 97
<212> TYPE: PRT
<213> ORGANISM: Rattus Norvegicus

<400> SEQUENCE: 52

Ala Arg Thr Thr Ala Pro Ser Val Tyr Pro Leu Val Pro Gly Cys Ser
1               5                   10                  15

Gly Thr Ser Gly Ser Leu Val Thr Leu Gly Cys Leu Val Lys Gly Tyr
            20                  25                  30

Phe Pro Glu Pro Val Thr Val Lys Trp Asn Ser Gly Ala Leu Ser Ser
            35                  40                  45

Gly Val His Thr Phe Pro Ala Val Leu Gln Ser Gly Leu Tyr Thr Leu
        50                  55                  60

Ser Ser Ser Val Thr Val Pro Ser Ser Thr Trp Ser Ser Gln Thr Val
65                  70                  75                  80

Thr Cys Ser Val Ala His Pro Ala Thr Lys Ser Asn Leu Ile Lys Arg
                85                  90                  95

Ile

<210> SEQ ID NO 53
<211> LENGTH: 15
<212> TYPE: PRT

```
<213> ORGANISM: Rattus Norvegicus

<400> SEQUENCE: 53

Val Pro Arg Asn Cys Gly Gly Asp Cys Lys Pro Cys Ile Cys Thr
1               5                   10                  15

<210> SEQ ID NO 54
<211> LENGTH: 11
<212> TYPE: PRT
<213> ORGANISM: Rattus Norvegicus

<400> SEQUENCE: 54

Val Pro Arg Glu Cys Asn Pro Cys Gly Cys Thr
1               5                   10

<210> SEQ ID NO 55
<211> LENGTH: 21
<212> TYPE: PRT
<213> ORGANISM: Rattus Norvegicus

<400> SEQUENCE: 55

Glu Arg Arg Asn Gly Gly Ile Gly His Lys Cys Pro Thr Cys Pro Thr
1               5                   10                  15

Cys His Lys Cys Pro
            20

<210> SEQ ID NO 56
<211> LENGTH: 17
<212> TYPE: PRT
<213> ORGANISM: Rattus Norvegicus

<400> SEQUENCE: 56

Glu Pro Arg Arg Pro Lys Pro Arg Pro Pro Thr Asp Ile Cys Ser Cys
1               5                   10                  15

Asp

<210> SEQ ID NO 57
<211> LENGTH: 107
<212> TYPE: PRT
<213> ORGANISM: Rattus Norvegicus

<400> SEQUENCE: 57

Gly Arg Thr Gln Val Pro His Val Tyr Thr Met Ser Pro Thr Lys Glu
1               5                   10                  15

Glu Met Thr Gln Asn Glu Val Ser Ile Thr Cys Met Val Lys Gly Phe
                20                  25                  30

Tyr Pro Pro Asp Ile Tyr Val Glu Trp Gln Met Asn Gly Gln Pro Gln
            35                  40                  45

Glu Asn Tyr Lys Asn Thr Pro Pro Thr Met Asp Thr Asp Gly Ser Tyr
        50                  55                  60

Phe Leu Tyr Ser Lys Leu Asn Val Lys Lys Glu Lys Trp Gln Gln Gly
65                  70                  75                  80

Asn Thr Phe Thr Cys Ser Val Leu His Glu Gly Leu His Asn His His
                85                  90                  95

Thr Glu Lys Ser Leu Ser His Ser Pro Gly Lys
            100                 105

<210> SEQ ID NO 58
<211> LENGTH: 107
<212> TYPE: PRT
<213> ORGANISM: Rattus Norvegicus
```

<400> SEQUENCE: 58

```
Gly Thr Pro Arg Gly Pro Gln Val Tyr Thr Met Ala Pro Pro Lys Glu
1               5                   10                  15

Glu Met Thr Gln Ser Gln Val Ser Ile Thr Cys Met Val Lys Gly Phe
            20                  25                  30

Tyr Pro Pro Asp Ile Tyr Thr Glu Trp Lys Met Asn Gly Gln Pro Gln
                35                  40                  45

Glu Asn Tyr Lys Asn Thr Pro Pro Thr Met Asp Thr Asp Gly Ser Tyr
    50                  55                  60

Phe Leu Tyr Ser Lys Leu Asn Val Lys Lys Glu Thr Trp Gln Gln Gly
65                  70                  75                  80

Asn Thr Phe Thr Cys Ser Val Leu His Glu Gly Leu His Asn His His
                85                  90                  95

Thr Glu Lys Ser Leu Ser His Ser Pro Gly Lys
            100                 105
```

<210> SEQ ID NO 59
<211> LENGTH: 105
<212> TYPE: PRT
<213> ORGANISM: Rattus Norvegicus

<400> SEQUENCE: 59

```
Gly Leu Val Arg Lys Pro Gln Val Tyr Val Met Gly Pro Pro Thr Glu
1               5                   10                  15

Gln Leu Thr Glu Gln Thr Val Ser Leu Thr Cys Leu Thr Ser Gly Phe
            20                  25                  30

Leu Pro Asn Asp Ile Gly Val Glu Trp Thr Ser Asn Gly His Ile Glu
                35                  40                  45

Lys Asn Tyr Lys Asn Thr Glu Pro Val Met Asp Ser Asp Gly Ser Phe
    50                  55                  60

Phe Met Tyr Ser Lys Leu Asn Val Glu Arg Ser Arg Trp Asp Ser Arg
65                  70                  75                  80

Ala Pro Phe Val Cys Ser Val Val His Glu Gly Leu His Asn His His
                85                  90                  95

Val Glu Lys Ser Ile Ser Arg Pro Pro
            100                 105
```

<210> SEQ ID NO 60
<211> LENGTH: 107
<212> TYPE: PRT
<213> ORGANISM: Rattus Norvegicus

<400> SEQUENCE: 60

```
Gly Lys Ala Arg Thr Pro Gln Val Tyr Thr Ile Pro Pro Pro Arg Glu
1               5                   10                  15

Gln Met Ser Lys Asn Lys Val Ser Leu Thr Cys Met Val Thr Ser Phe
            20                  25                  30

Tyr Pro Ala Ser Ile Ser Val Glu Trp Glu Arg Asn Gly Glu Leu Glu
                35                  40                  45

Gln Asp Tyr Lys Asn Thr Leu Pro Val Leu Asp Ser Asp Glu Ser Tyr
    50                  55                  60

Phe Leu Tyr Ser Lys Leu Ser Val Asp Thr Asp Ser Trp Met Arg Gly
65                  70                  75                  80

Asp Ile Tyr Thr Cys Ser Val His Glu Ala Leu His Asn His His
                85                  90                  95
```

-continued

Thr Gln Lys Asn Leu Ser Arg Ser Pro Gly Lys
            100                 105

<210> SEQ ID NO 61
<211> LENGTH: 15
<212> TYPE: PRT
<213> ORGANISM: Homo Sapiens

<400> SEQUENCE: 61

Glu Pro Lys Ser Cys Asp Lys Thr His Thr Cys Pro Pro Cys Pro
1               5                   10                  15

<210> SEQ ID NO 62
<211> LENGTH: 121
<212> TYPE: PRT
<213> ORGANISM: Homo Sapiens

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Leu Ser Ala Tyr Ser Gly Asn Thr Ile Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Asp Tyr Trp Gly
            100                 105                 110

Gln Gly Thr Leu Val Thr Val Ser Ser
        115                 120

<210> SEQ ID NO 63
<211> LENGTH: 107
<212> TYPE: PRT
<213> ORGANISM: Homo Sapiens

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 64
<211> LENGTH: 116
<212> TYPE: PRT

```
<213> ORGANISM: Cricetulus migratorius

<400> SEQUENCE: 64

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser
        115

<210> SEQ ID NO 65
<211> LENGTH: 107
<212> TYPE: PRT
<213> ORGANISM: Cricetulus migratorius

<400> SEQUENCE: 65

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Asn Lys Leu Ala Asp Gly Val Pro Ser Arg Phe Ser Gly
    50                  55                  60

Ser Gly Ser Gly Arg Asp Ser Ser Phe Thr Ile Ser Ser Leu Glu Ser
65                  70                  75                  80

Glu Asp Ile Gly Ser Tyr Tyr Cys Gln Gln Tyr Tyr Asn Tyr Pro Trp
                85                  90                  95

Thr Phe Gly Pro Gly Thr Lys Leu Glu Ile Lys
            100                 105

<210> SEQ ID NO 66
<211> LENGTH: 121
<212> TYPE: PRT
<213> ORGANISM: Mus musculus

<400> SEQUENCE: 66

Glu Val Gln Leu Gln Gln Ser Gly Ala Glu Leu Val Arg Pro Gly Ala
1               5                   10                  15

Leu Val Lys Leu Ser Cys Lys Thr Ser Gly Phe Asn Ile Lys Asp Tyr
            20                  25                  30

Phe Leu His Trp Val Arg Gln Arg Pro Asp Gln Gly Leu Glu Trp Ile
        35                  40                  45

Gly Trp Ile Asn Pro Asp Asn Gly Asn Thr Val Tyr Asp Pro Lys Phe
    50                  55                  60

Gln Gly Thr Ala Ser Leu Thr Ala Asp Thr Ser Ser Asn Thr Val Tyr
65                  70                  75                  80
```

```
Leu Gln Leu Ser Gly Leu Thr Ser Glu Asp Thr Ala Val Tyr Phe Cys
                85                  90                  95

Thr Arg Arg Asp Tyr Thr Tyr Glu Lys Ala Ala Leu Asp Tyr Trp Gly
            100                 105                 110

Gln Gly Ala Ser Val Ile Val Ser Ser
        115                 120
```

<210> SEQ ID NO 67
<211> LENGTH: 107
<212> TYPE: PRT
<213> ORGANISM: Mus musculus

<400> SEQUENCE: 67

```
Ala Ile Gln Met Ser Gln Ser Pro Ala Ser Leu Ser Ala Ser Val Gly
1               5                   10                  15

Glu Thr Val Thr Ile Thr Cys Arg Ala Ser Gly Asn Ile Tyr Asn Tyr
            20                  25                  30

Leu Ala Trp Tyr Gln Gln Lys Gln Gly Lys Ser Pro His Leu Leu Val
        35                  40                  45

Tyr Asp Ala Lys Thr Leu Ala Asp Gly Val Pro Ser Arg Phe Ser Gly
50                  55                  60

Ser Gly Ser Gly Thr Gln Tyr Ser Leu Lys Ile Ser Ser Leu Gln Thr
65                  70                  75                  80

Glu Asp Ser Gly Asn Tyr Tyr Cys Gln His Phe Trp Ser Leu Pro Phe
                85                  90                  95

Thr Phe Gly Ser Gly Thr Lys Leu Glu Ile Lys
            100                 105
```

<210> SEQ ID NO 68
<211> LENGTH: 127
<212> TYPE: PRT
<213> ORGANISM: Homo Sapiens

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125
```

<210> SEQ ID NO 69
<211> LENGTH: 108
<212> TYPE: PRT
<213> ORGANISM: Homo Sapiens

<400> SEQUENCE: 69

-continued

```
Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20              25              30

Arg Val Ala Trp Tyr Gln His Lys Pro Gly Gln Ala Pro Arg Leu Val
            35              40              45

Ile His Gly Val Ser Asn Arg Ala Ser Gly Ile Ser Asp Arg Phe Ser
        50              55              60

Gly Ser Gly Ser Gly Thr Asp Phe Thr Leu Thr Ile Thr Arg Val Glu
65              70              75              80

Pro Glu Asp Phe Ala Leu Tyr Tyr Cys Gln Val Tyr Gly Ala Ser Ser
                85              90              95

Tyr Thr Phe Gly Gln Gly Thr Lys Leu Glu Arg Lys
                100             105
```